(12) United States Patent
Appleyard et al.

(10) Patent No.: US 11,796,449 B2
(45) Date of Patent: Oct. 24, 2023

(54) MICROFLUIDIC SYSTEM AND METHOD WITH FOCUSED ENERGY APPARATUS

(71) Applicant: ABS Global, Inc., DeForest, WI (US)

(72) Inventors: David Appleyard, DeForest, WI (US); Jeff Betthauser, DeForest, WI (US); Marjorie Faust, DeForest, WI (US); John Larsen, DeForest, WI (US); Guocheng Shao, DeForest, WI (US); Zheng Xia, DeForest, WI (US); Yu Zhou, DeForest, WI (US)

(73) Assignee: ABS Global, Inc., DeForest, WI (US)

( * ) Notice: Subject to any disclaimer, the term of this patent is extended or adjusted under 35 U.S.C. 154(b) by 1108 days.

(21) Appl. No.: 16/279,430

(22) Filed: Feb. 19, 2019

(65) Prior Publication Data

US 2019/0187044 A1     Jun. 20, 2019

Related U.S. Application Data

(63) Continuation-in-part of application No. 15/387,034, filed on Dec. 21, 2016, now abandoned, which is a
(Continued)

(51) Int. Cl.
*G01N 15/14* (2006.01)
*G01N 33/483* (2006.01)
(Continued)

(52) U.S. Cl.
CPC .... *G01N 15/1484* (2013.01); *B01L 3/502761* (2013.01); *C12N 13/00* (2013.01);
(Continued)

(58) Field of Classification Search
CPC .. G01N 15/1484; G01N 1/44; G01N 15/1404; G01N 21/01; G01N 21/6486;
(Continued)

(56) References Cited

U.S. PATENT DOCUMENTS 3,390,449 A    7/1968   Fox
3,649,829 A    3/1972   Randolph
(Continued)

FOREIGN PATENT DOCUMENTS

CA     1341328 C    12/2001
CN     2125369 U    12/1992
(Continued)

OTHER PUBLICATIONS

Trial Transcript, Sep. 5, 2019 (a.m.); *ABS Global, Inc. v. Inguran, LLC d/b/a Sexing Technologies*, Case Nos. 17-cv-446 and 14-cv-503, United States District Court for the Western District of Wisconsin.
(Continued)

*Primary Examiner* — Samuel P Siefke
(74) *Attorney, Agent, or Firm* — NGUYEN TARBET LLC

(57) ABSTRACT

A method of inseminating an animal including flowing a stream of a population of sperm cells through a channel, differentiating the sperm cells into two subpopulations of X-chromosome containing sperm cells and Y-chromosome containing sperm cells, selecting a desired subpopulation, ablating an undesired subpopulation, and collecting both the subpopulations of sperm cells including the desired subpopulation and the ablated undesired subpopulation together, wherein the collected population of sperm cells is used to fertilize an egg.

43 Claims, 40 Drawing Sheets

Related U.S. Application Data continuation of application No. 15/033,001, filed as application No. PCT/IB2014/001425 on Jun. 18, 2014, now Pat. No. 10,928,298.

(60) Provisional application No. 61/897,743, filed on Oct. 30, 2013.

(51) Int. Cl.
| | | |
|---|---|---|
| *G01N 21/01* | (2006.01) | |
| *B01L 3/00* | (2006.01) | |
| *C12N 13/00* | (2006.01) | |
| *G01N 1/44* | (2006.01) | |
| *G01N 21/64* | (2006.01) | |
| *G01N 15/10* | (2006.01) | |

(52) U.S. Cl.
CPC ............ *G01N 1/44* (2013.01); *G01N 15/1404* (2013.01); *G01N 21/01* (2013.01); *G01N 21/6486* (2013.01); *G01N 33/4833* (2013.01); *B01L 2200/0636* (2013.01); *B01L 2200/0652* (2013.01); *B01L 2300/0627* (2013.01); *B01L 2300/0887* (2013.01); *G01N 2015/1006* (2013.01); *G01N 2015/1409* (2013.01); *G01N 2015/1413* (2013.01)

(58) Field of Classification Search
CPC ....... G01N 33/4833; G01N 2015/1006; G01N 2015/1409; G01N 2015/1413; G01N 15/1459; G01N 2015/149; B01L 3/502761; B01L 2200/0636; B01L 2200/0652; B01L 2300/0627; B01L 2300/0887; C12N 13/00
See application file for complete search history.

(56) References Cited

U.S. PATENT DOCUMENTS

| | | |
|---|---|---|
| 3,661,460 A | 5/1972 | Elking et al. |
| 3,710,933 A | 1/1973 | Fulwyler et al. |
| 3,764,901 A | 10/1973 | Kachel |
| 3,791,517 A | 2/1974 | Friedman |
| 4,175,662 A | 11/1979 | Zold |
| 4,325,706 A | 4/1982 | Gershman et al. |
| 4,395,397 A | 7/1983 | Shapiro |
| 4,409,106 A | 10/1983 | Furuta et al. |
| 4,424,132 A | 1/1984 | Iriguchi |
| 4,660,971 A | 4/1987 | Sage et al. |
| 4,667,830 A | 5/1987 | Nozaki, Jr. et al. |
| 4,765,737 A | 8/1988 | Harris et al. |
| 4,885,473 A | 12/1989 | Shofner et al. |
| 4,919,817 A | 4/1990 | Schoendorfer et al. |
| 4,983,038 A | 1/1991 | Ohki et al. |
| 5,007,732 A | 4/1991 | Ohki et al. |
| 5,030,002 A | 7/1991 | North, Jr. |
| 5,100,627 A | 3/1992 | Buican et al. |
| 5,125,749 A | 6/1992 | Leugers et al. |
| 5,135,759 A | 8/1992 | Johnson |
| 5,180,065 A | 1/1993 | Touge et al. |
| 5,194,909 A | 3/1993 | Tycko |
| 5,229,297 A | 7/1993 | Schnipelsky et al. |
| 5,483,469 A | 1/1996 | Van den engh et al. |
| 5,491,550 A | 2/1996 | Dabbs |
| 5,620,857 A | 4/1997 | Weetail et al. |
| 5,674,743 A | 10/1997 | Ulmer |
| 5,689,109 A | 11/1997 | Schultze |
| 5,752,606 A | 5/1998 | Wilson et al. |
| 5,800,690 A | 9/1998 | Chow et al. |
| 5,837,115 A | 11/1998 | Austin et al. |
| 5,849,178 A | 12/1998 | Holm et al. |
| 5,858,187 A | 1/1999 | Ramsey et al. |
| 5,879,625 A | 3/1999 | Rosianiec et al. |
| 5,966,457 A | 10/1999 | Lemelson |
| 5,985,216 A | 11/1999 | Rens et al. |
| 6,008,010 A | 12/1999 | Greenberger et al. |
| 6,053,856 A | 4/2000 | Hlavinka |
| 6,071,442 A | 6/2000 | Dean et al. |
| 6,146,897 A | 11/2000 | Cohenford et al. |
| 6,159,739 A | 12/2000 | Weigl et al. |
| 6,159,749 A | 12/2000 | Yagang et al. |
| 6,171,865 B1 | 1/2001 | Weigl et al. |
| 6,185,664 B1 | 2/2001 | Jeddeloh |
| 6,213,151 B1 | 4/2001 | Jacobson et al. |
| H1960 H | 6/2001 | Conrad et al. |
| 6,368,871 B1 | 4/2002 | Christel et al. |
| 6,416,190 B1 | 7/2002 | Grier et al. |
| 6,416,959 B1 | 7/2002 | Giuliano et al. |
| 6,432,630 B1 | 8/2002 | Blankenstein |
| 6,451,264 B1 | 9/2002 | Bhullar et al. |
| 6,473,171 B1 | 10/2002 | Buttry et al. |
| 6,494,230 B2 | 12/2002 | Chow |
| 6,506,609 B1 | 1/2003 | Wada et al. |
| 6,519,032 B1 | 2/2003 | Kuebler et al. |
| 6,519,954 B1 | 2/2003 | Prien et al. |
| 6,524,860 B1 | 2/2003 | Seidel et al. |
| 6,540,895 B1 | 4/2003 | Spence et al. |
| 6,549,275 B1 | 4/2003 | Cabuz et al. |
| 6,592,821 B1 | 7/2003 | Wada et al. |
| 6,637,463 B1 | 10/2003 | Lei et al. |
| 6,674,525 B2 | 1/2004 | Bardell et al. |
| 6,727,451 B1 | 4/2004 | Fuhr et al. |
| 6,808,075 B2 | 10/2004 | Böhm et al. |
| 6,833,542 B2 | 12/2004 | Wang et al. |
| 6,838,056 B2 | 1/2005 | Foster |
| 6,841,388 B2 | 1/2005 | Dukor et al. |
| 6,853,654 B2 | 2/2005 | Mcdonald et al. |
| 6,877,528 B2 | 4/2005 | Gilbert et al. |
| 6,944,324 B2 | 9/2005 | Tran et al. |
| 6,976,590 B2 | 12/2005 | Deshpande et al. |
| 7,029,430 B2 | 4/2006 | Hlavinka et al. |
| 7,069,943 B2 | 7/2006 | Gilbert et al. |
| 7,092,154 B2 | 8/2006 | Yasuda et al. |
| 7,104,405 B2 | 9/2006 | Böhm et al. |
| 7,208,265 B1 | 4/2007 | Schenk |
| 7,195,920 B2 | 5/2007 | Seidel et al. |
| 7,241,988 B2 | 7/2007 | Gruber et al. |
| 7,276,701 B2 | 10/2007 | Lendl |
| 7,298,478 B2 | 11/2007 | Gilbert et al. |
| 7,300,803 B2 | 11/2007 | Lin et al. |
| 7,311,476 B2 | 12/2007 | Gilbert et al. |
| 7,312,085 B2 | 12/2007 | Chou et al. |
| 7,355,696 B2 | 4/2008 | Mueth et al. |
| 7,355,699 B2 | 4/2008 | Gilbert et al. |
| 7,466,734 B1 | 12/2008 | Day et al. |
| 7,472,794 B2 | 1/2009 | Oakey et al. |
| 7,482,577 B2 | 1/2009 | Gruber et al. |
| 7,492,522 B2 | 2/2009 | Gilbert et al. |
| 7,524,681 B2 | 4/2009 | Wolf et al. |
| 7,569,788 B2 | 8/2009 | Deshpande et al. |
| 7,576,861 B2 | 8/2009 | Gilbert et al. |
| 7,584,857 B2 | 9/2009 | Böhm et al. |
| 7,611,309 B2 | 11/2009 | Gilbert et al. |
| 7,670,471 B2 | 3/2010 | Quake et al. |
| 7,697,576 B2 | 4/2010 | Maier et al. |
| 7,760,351 B2 | 7/2010 | Cox et al. |
| 7,820,425 B2 | 10/2010 | Schenk |
| 7,826,509 B2 | 11/2010 | Belkin et al. |
| 7,956,328 B2 | 6/2011 | Sundaram et al. |
| 7,963,399 B2 | 6/2011 | Böhm et al. |
| 7,997,831 B2 | 8/2011 | Gilbert et al. |
| 8,032,200 B2 | 10/2011 | Tearney et al. |
| 8,080,422 B2 | 12/2011 | Neas et al. |
| 8,123,044 B2 | 2/2012 | Johnson et al. |
| 8,149,402 B2 | 4/2012 | Rich |
| 8,158,122 B2 | 4/2012 | Hampson et al. |
| 8,173,001 B2 | 5/2012 | Quake et al. |
| 8,174,394 B2 | 5/2012 | Ridder et al. |
| 8,198,092 B2 | 6/2012 | Durack et al. |
| 8,206,987 B2 | 6/2012 | Durack et al. |
| 8,209,987 B2 | 7/2012 | Hautman et al. |
| 8,210,209 B2 | 7/2012 | Gilbert et al. |
| 8,277,764 B2 | 10/2012 | Gilbert et al. |

(56) References Cited

U.S. PATENT DOCUMENTS

| | | |
|---|---|---|
| 8,388,822 B2 | 3/2013 | Quake et al. |
| 8,408,399 B2 | 4/2013 | Böhm et al. |
| 8,502,148 B2 | 8/2013 | Wagner et al. |
| 8,529,161 B2 | 9/2013 | Gilbert et al. |
| 8,563,325 B1 | 10/2013 | Bartsch et al. |
| 8,567,608 B2 | 10/2013 | Deshpande et al. |
| 8,569,069 B2 | 10/2013 | Durack |
| 8,623,295 B2 | 1/2014 | Gilbert et al. |
| 8,727,131 B2 | 5/2014 | Deshpande et al. |
| 8,731,860 B2 | 5/2014 | Charles et al. |
| 8,863,962 B2 | 10/2014 | Johnson et al. |
| 8,941,062 B2 | 1/2015 | Wagner et al. |
| 8,961,904 B2 | 2/2015 | Xia et al. |
| 8,964,184 B2 | 2/2015 | Gilbert et al. |
| 8,981,298 B2 | 3/2015 | Wagner et al. |
| 9,000,357 B2 | 4/2015 | Mueth et al. |
| 9,003,869 B2 | 4/2015 | Wagner et al. |
| 9,011,797 B2 | 4/2015 | Gilbert et al. |
| 9,109,195 B2 | 8/2015 | Zimmermann et al. |
| 9,140,690 B2 | 9/2015 | Mueth et al. |
| 9,255,874 B2 | 2/2016 | Sharpe et al. |
| 9,260,693 B2 | 2/2016 | Johnson et al. |
| 9,335,247 B2 | 5/2016 | Sharpe et al. |
| 9,335,295 B2 | 5/2016 | Mueth et al. |
| 9,339,850 B2 | 5/2016 | Deshpande et al. |
| 9,365,822 B2 | 6/2016 | Seidel et al. |
| 9,377,400 B2 | 6/2016 | Wagner et al. |
| 9,446,912 B2 | 9/2016 | Gilbert et al. |
| 9,485,984 B2 | 11/2016 | Burbank et al. |
| 9,550,215 B2 | 1/2017 | Deshpande et al. |
| 9,588,100 B2 | 3/2017 | Appleyard et al. |
| 9,618,442 B2 | 4/2017 | Sharpe et al. |
| 9,683,922 B2 | 6/2017 | Wagner et al. |
| D791,338 S | 7/2017 | Morkos et al. |
| 9,752,976 B2 | 9/2017 | Gilbert et al. |
| 9,781,918 B2 | 10/2017 | Zimmermann et al. |
| 9,802,767 B2 | 10/2017 | Gilbert et al. |
| 9,823,252 B2 | 11/2017 | Gilbert et al. |
| 9,835,552 B2 | 12/2017 | Wagner |
| D815,754 S | 4/2018 | Morkos et al. |
| 9,943,847 B2 | 4/2018 | Gilbert et al. |
| 9,964,968 B2 | 5/2018 | Sharpe et al. |
| 10,025,322 B2 | 7/2018 | Lofstrom et al. |
| 10,029,283 B2 | 7/2018 | Deshpande et al. |
| 10,175,159 B2 | 1/2019 | Wagner et al. |
| 10,180,388 B2 | 1/2019 | Wagner |
| 10,216,144 B2 | 2/2019 | Mueth et al. |
| 10,315,194 B2 | 6/2019 | Akiyama et al. |
| 11,187,224 B2 | 11/2021 | Xia et al. |
| 11,193,879 B2 | 12/2021 | Wagner et al. |
| 11,243,494 B2 | 2/2022 | Mueth et al. |
| 2002/0027649 A1 | 3/2002 | Chudner |
| 2002/0042042 A1 | 4/2002 | Fahy |
| 2002/0058332 A1 | 5/2002 | Quake et al. |
| 2002/0106716 A1 | 8/2002 | Leboeuf et al. |
| 2002/0115208 A1 | 8/2002 | Mitchell et al. |
| 2002/0176069 A1 | 11/2002 | Hansen et al. |
| 2002/0198928 A1 | 12/2002 | Bukshpan et al. |
| 2003/0007894 A1 | 1/2003 | Wang et al. |
| 2003/0032204 A1 | 2/2003 | Walt et al. |
| 2003/0047676 A1 | 3/2003 | Grier et al. |
| 2003/0054365 A1 | 3/2003 | Xu et al. |
| 2003/0054558 A1 | 3/2003 | Kurabayashi et al. |
| 2003/0068646 A1 | 4/2003 | Singh et al. |
| 2003/0113709 A1 | 6/2003 | Alivisatos et al. |
| 2003/0175944 A1 | 9/2003 | Yang et al. |
| 2003/0175980 A1 | 9/2003 | Hayenga et al. |
| 2003/0186426 A1 | 10/2003 | Brewer et al. |
| 2004/0043506 A1 | 3/2004 | Haussecker et al. |
| 2004/0079893 A1 | 4/2004 | Dietz et al. |
| 2004/0089798 A1 | 5/2004 | Gruber et al. |
| 2004/0144648 A1 | 7/2004 | Jacobson et al. |
| 2004/0161772 A1 | 8/2004 | Bohm et al. |
| 2004/0166504 A1 | 8/2004 | Rossier et al. |
| 2004/0206399 A1 | 10/2004 | Heller et al. |
| 2004/0217297 A1 | 11/2004 | Moses et al. |
| 2004/0229349 A1 | 11/2004 | Daridon |
| 2004/0266022 A1 | 12/2004 | Sundararajan et al. |
| 2005/0037471 A1 | 2/2005 | Liu et al. |
| 2005/0061962 A1 | 3/2005 | Mueth et al. |
| 2005/0103690 A1 | 5/2005 | Kawano et al. |
| 2005/0112541 A1 | 5/2005 | Durack et al. |
| 2005/0121604 A1 | 6/2005 | Mueth et al. |
| 2005/0123450 A1 | 6/2005 | Gilbert |
| 2005/0124869 A1 | 6/2005 | Hefti et al. |
| 2005/0148085 A1 | 7/2005 | Larsen |
| 2005/0153354 A1 | 7/2005 | Gilmanshin |
| 2005/0190372 A1 | 9/2005 | Dogariu |
| 2005/0196876 A1 | 9/2005 | Chan et al. |
| 2005/0207940 A1 | 9/2005 | Butler et al. |
| 2005/0207943 A1 | 9/2005 | Puzey |
| 2006/0013270 A1 | 1/2006 | Yumoto et al. |
| 2006/0035273 A1 | 2/2006 | Quake et al. |
| 2006/0043301 A1 | 3/2006 | Mantele et al. |
| 2006/0058167 A1 | 3/2006 | Regusa et al. |
| 2006/0078888 A1 | 4/2006 | Griffiths |
| 2006/0105453 A1 | 5/2006 | Brenan et al. |
| 2006/0152707 A1 | 7/2006 | Kanda |
| 2006/0170912 A1 | 8/2006 | Mueth et al. |
| 2006/0252047 A1 | 11/2006 | Ekstrom et al. |
| 2006/0257089 A1 | 11/2006 | Mueth et al. |
| 2006/0263829 A1 | 11/2006 | Evans et al. |
| 2007/0009386 A1 | 1/2007 | Padmanabhan et al. |
| 2007/0078348 A1 | 4/2007 | Holman |
| 2007/0114172 A1 | 5/2007 | Mueth et al. |
| 2007/0128082 A1 | 6/2007 | Yang et al. |
| 2007/0207551 A1 | 9/2007 | Glensbjerg |
| 2007/0247620 A1 | 10/2007 | Koo |
| 2007/0248958 A1 | 10/2007 | Jovanovich et al. |
| 2007/0255362 A1 | 11/2007 | Levinson |
| 2008/0003685 A1 | 1/2008 | Goix et al. |
| 2008/0014574 A1 | 1/2008 | Viator et al. |
| 2008/0021674 A1 | 1/2008 | Puskas |
| 2008/0069733 A1 | 3/2008 | Maltezo et al. |
| 2008/0144037 A1 | 6/2008 | Mueth et al. |
| 2008/0166188 A1 | 7/2008 | Gilbert et al. |
| 2008/0195020 A1 | 8/2008 | Cabuz et al. |
| 2008/0213821 A1 | 9/2008 | Liu et al. |
| 2008/0248966 A1 | 10/2008 | Hansen et al. |
| 2008/0261295 A1 | 10/2008 | Butler et al. |
| 2008/0292555 A1 | 11/2008 | Ye et al. |
| 2008/0299013 A1 | 12/2008 | Trieu et al. |
| 2008/0309919 A1 | 12/2008 | Birmingham et al. |
| 2008/0311005 A1 | 12/2008 | Kim et al. |
| 2009/0004652 A1 | 1/2009 | Rubin et al. |
| 2009/0029870 A1 | 1/2009 | Ward et al. |
| 2009/0032449 A1 | 2/2009 | Mueth et al. |
| 2009/0042241 A1 | 2/2009 | Yu-Chong et al. |
| 2009/0051912 A1 | 2/2009 | Salazar et al. |
| 2009/0114285 A1 | 5/2009 | Hashimoto et al. |
| 2009/0125242 A1 | 5/2009 | Choi et al. |
| 2009/0141279 A1 | 6/2009 | Hillmer |
| 2009/0156932 A1 | 6/2009 | Zharov |
| 2009/0170149 A1 | 7/2009 | Viator et al. |
| 2009/0176271 A1 | 7/2009 | Durack et al. |
| 2009/0201504 A1 | 8/2009 | Ho et al. |
| 2009/0225319 A1 | 9/2009 | Lee et al. |
| 2009/0281250 A1 | 11/2009 | DeSimone et al. |
| 2009/0290156 A1 | 11/2009 | Popescu et al. |
| 2010/0044570 A1 | 2/2010 | McGill et al. |
| 2010/0068723 A1 | 3/2010 | Jovanovich et al. |
| 2010/0079516 A1 | 4/2010 | Nakazawa |
| 2010/0167336 A1 | 7/2010 | Son et al. |
| 2010/0171954 A1 | 7/2010 | Quake et al. |
| 2010/0216208 A1 | 8/2010 | Mueth et al. |
| 2010/0248362 A1 | 9/2010 | Durack et al. |
| 2010/0330693 A1 | 12/2010 | Chapin et al. |
| 2011/0001963 A1 | 1/2011 | Durack |
| 2011/0003303 A1 | 1/2011 | Pagano et al. |
| 2011/0003324 A1 | 1/2011 | Durack |
| 2011/0003325 A1 | 1/2011 | Durack |
| 2011/0003330 A1 | 1/2011 | Durack |
| 2011/0008764 A1 | 1/2011 | Silva et al. |
| 2011/0008767 A1 | 1/2011 | Durack |

(56) References Cited

U.S. PATENT DOCUMENTS

| | | | |
|---|---|---|---|
| 2011/0008817 A1 | 1/2011 | Durack | |
| 2011/0008818 A1 | 1/2011 | Durack | |
| 2011/0075928 A1 | 3/2011 | Jeong et al. | |
| 2011/0076712 A1 | 3/2011 | Gilligan et al. | |
| 2011/0090500 A1 | 4/2011 | Hu et al. | |
| 2011/0096327 A1 | 4/2011 | Papautsky et al. | |
| 2011/0190146 A1 | 8/2011 | Boehm et al. | |
| 2011/0223654 A1 | 9/2011 | Holman et al. | |
| 2011/0256523 A1 | 10/2011 | Mendele et al. | |
| 2011/0256575 A1* | 10/2011 | Durack | G01N 33/48 435/29 |
| 2011/0263747 A1 | 10/2011 | Doyle et al. | |
| 2011/0294139 A1 | 12/2011 | Takeda | |
| 2012/0009619 A1 | 1/2012 | Gilbert et al. | |
| 2012/0028366 A1 | 2/2012 | Krager et al. | |
| 2012/0033220 A1 | 2/2012 | Kotidis et al. | |
| 2012/0033697 A1 | 2/2012 | Goyal et al. | |
| 2012/0081709 A1 | 4/2012 | Durack | |
| 2012/0082362 A1 | 4/2012 | Diem et al. | |
| 2012/0107805 A1 | 5/2012 | Neas et al. | |
| 2012/0122084 A1 | 5/2012 | Wagner et al. | |
| 2012/0138152 A1 | 6/2012 | Villarruel et al. | |
| 2012/0183947 A1 | 7/2012 | Mueth et al. | |
| 2012/0196356 A1 | 8/2012 | Wagner et al. | |
| 2012/0199741 A1 | 8/2012 | Wagner et al. | |
| 2012/0199742 A1 | 8/2012 | Wagner et al. | |
| 2012/0202237 A1 | 8/2012 | Sedoglavich et al. | |
| 2012/0202277 A1 | 8/2012 | Wagner et al. | |
| 2012/0202278 A1 | 8/2012 | Wagner et al. | |
| 2012/0204628 A1 | 8/2012 | Wagner et al. | |
| 2012/0225474 A1 | 9/2012 | Wagner et al. | |
| 2012/0225475 A1 | 9/2012 | Wagner et al. | |
| 2012/0273054 A1 | 11/2012 | Lou et al. | |
| 2012/0287419 A1 | 11/2012 | Sharpe et al. | |
| 2012/0295263 A1 | 11/2012 | Cantor et al. | |
| 2012/0307244 A1 | 12/2012 | Sharpe et al. | |
| 2013/0121877 A1 | 5/2013 | Ono | |
| 2013/0164731 A1 | 6/2013 | Cimino et al. | |
| 2013/0164773 A1 | 6/2013 | Bardell et al. | |
| 2013/0200277 A1 | 8/2013 | Li et al. | |
| 2013/0224843 A1 | 8/2013 | Evans et al. | |
| 2013/0252237 A1 | 9/2013 | Wagner | |
| 2013/0295602 A1 | 11/2013 | Fowler | |
| 2013/0313170 A1 | 11/2013 | Bohm et al. | |
| 2014/0033808 A1 | 2/2014 | Ding et al. | |
| 2014/0050540 A1 | 2/2014 | Gilbert et al. | |
| 2014/0091014 A1 | 4/2014 | Wagner et al. | |
| 2014/0224710 A1 | 8/2014 | Di Carlo et al. | |
| 2014/0273192 A1 | 9/2014 | Sharpe | |
| 2014/0287243 A1 | 9/2014 | Weber et al. | |
| 2014/0318645 A1 | 10/2014 | Koksal | |
| 2014/0339446 A1 | 11/2014 | Yamamoto et al. | |
| 2014/0361148 A1 | 12/2014 | Popescu et al. | |
| 2015/0064694 A1 | 3/2015 | Sadri | |
| 2015/0114093 A1 | 4/2015 | Appleyard et al. | |
| 2015/0192511 A1 | 7/2015 | Wagner et al. | |
| 2015/0198517 A1 | 7/2015 | Simpson et al. | |
| 2015/0276588 A1 | 10/2015 | Marshall et al. | |
| 2016/0004060 A1 | 1/2016 | Simpson et al. | |
| 2016/0123858 A1 | 5/2016 | Kapur et al. | |
| 2016/0199835 A1 | 7/2016 | Tachibana et al. | |
| 2016/0303563 A1 | 10/2016 | Granier et al. | |
| 2017/0016813 A1 | 1/2017 | Wagner et al. | |
| 2017/0052105 A1 | 2/2017 | Appleyard et al. | |
| 2017/0181425 A1 | 6/2017 | Burbank et al. | |
| 2017/0307505 A1 | 10/2017 | Vrane et al. | |
| 2017/0333902 A1 | 11/2017 | Masaeli et al. | |
| 2018/0266937 A1 | 9/2018 | De Wagenaar et al. | |
| 2019/0025212 A1 | 1/2019 | Evans | |
| 2019/0040356 A1 | 2/2019 | Durack et al. | |
| 2019/0071725 A1 | 3/2019 | Roti-Roti et al. | |
| 2019/0187044 A1 | 6/2019 | Appleyard et al. | |
| 2019/0382720 A1 | 12/2019 | Savage et al. | |
| 2019/0390164 A1 | 12/2019 | Morjal et al. | |
| 2020/0070152 A1 | 3/2020 | Kasai et al. | |
| 2022/0025443 A1 | 1/2022 | Korani et al. | |
| 2022/0026341 A1 | 1/2022 | Appleyard et al. | |

FOREIGN PATENT DOCUMENTS

| | | |
|---|---|---|
| CN | 1482369 | 3/2004 |
| CN | 1886315 | 12/2006 |
| CN | 101189504 | 5/2008 |
| CN | 109221081 A | 1/2019 |
| CN | 109497040 A | 3/2019 |
| CN | 109517787 A | 3/2019 |
| EP | 0057907 | 8/1982 |
| EP | 0282994 | 9/1988 |
| EP | 0679325 | 7/1994 |
| EP | 0471758 A1 | 9/1996 |
| FR | 2798557 | 3/2001 |
| GB | 502971 | 5/1939 |
| GB | 2507959 | 5/2014 |
| GN | 1482369 | 3/2004 |
| JP | 57-131451 | 8/1982 |
| JP | 58090513 | 5/1983 |
| JP | 64026125 | 1/1989 |
| JP | S 64-26125 A | 1/1989 |
| JP | 64074451 | 3/1989 |
| JP | 02105041 | 4/1990 |
| JP | 03297385 | 12/1991 |
| JP | H0526799 | 2/1993 |
| JP | 06265452 | 9/1994 |
| JP | 06327494 | 11/1994 |
| JP | 07024309 | 1/1995 |
| JP | 07286953 | 10/1995 |
| JP | 2552582 | 11/1996 |
| JP | H10512952 | 12/1998 |
| JP | H11508182 | 7/1999 |
| JP | 2000146819 | 5/2000 |
| JP | 2000512541 | 9/2000 |
| JP | 2001504936 | 4/2001 |
| JP | 2002503334 | 1/2002 |
| JP | 2002153260 | 5/2002 |
| JP | 2003106980 | 4/2003 |
| JP | 2003515738 | 5/2003 |
| JP | 2004093553 | 3/2004 |
| JP | 2005502482 | 1/2005 |
| JP | 2005530986 | 10/2005 |
| JP | 2006524054 | 10/2006 |
| JP | 2007-514522 A | 6/2007 |
| JP | 2007148981 | 6/2007 |
| JP | 2007514522 | 6/2007 |
| JP | 2007515936 | 6/2007 |
| JP | 2008533440 | 8/2008 |
| JP | 2008261295 A1 | 10/2008 |
| JP | 2009085872 A | 4/2009 |
| JP | 2009115672 A | 5/2009 |
| JP | 2009162660 A | 7/2009 |
| JP | 2010117197 | 5/2010 |
| JP | 2010151777 | 7/2010 |
| JP | 2010190680 | 9/2010 |
| JP | 2011145185 | 7/2011 |
| JP | 2014503195 | 2/2014 |
| WO | WO9622521 | 7/1996 |
| WO | WO9700442 | 1/1997 |
| WO | WO1997030338 A1 | 8/1997 |
| WO | WO9739338 | 10/1997 |
| WO | WO9747390 | 12/1997 |
| WO | WO9810267 | 3/1998 |
| WO | WO99/39223 | 8/1999 |
| WO | 2000070080 | 11/2000 |
| WO | WO20000070080 A1 | 11/2000 |
| WO | WO0118400 | 3/2001 |
| WO | WO0131315 | 5/2001 |
| WO | WO2001040766 | 6/2001 |
| WO | WO0185913 | 11/2001 |
| WO | WO2002006778 A1 | 1/2002 |
| WO | WO200241906 | 5/2002 |
| WO | WO2002081183 A1 | 10/2002 |
| WO | WO02087792 | 11/2002 |
| WO | WO03024163 | 3/2003 |
| WO | WO03062867 | 7/2003 |

(56) References Cited

FOREIGN PATENT DOCUMENTS

| WO | WO03078065 A1 | 9/2003 |
|---|---|---|
| WO | WO2003078065 | 9/2003 |
| WO | WO2004012133 | 2/2004 |
| WO | WO2004029221 | 4/2004 |
| WO | WO2004043506 A1 | 5/2004 |
| WO | 2004088283 | 10/2004 |
| WO | WO2004088283 | 10/2004 |
| WO | WO20040088283 A1 | 10/2004 |
| WO | WO2005023391 | 3/2005 |
| WO | 2005042137 | 5/2005 |
| WO | 2005075629 | 8/2005 |
| WO | WO2005075629 | 8/2005 |
| WO | WO20050075629 A1 | 8/2005 |
| WO | 2006119806 | 11/2006 |
| WO | WO2006119806 | 11/2006 |
| WO | WO20060119806 A1 | 11/2006 |
| WO | WO2007008495 A2 | 1/2007 |
| WO | WO2007133710 A2 | 11/2007 |
| WO | 2008114458 | 9/2008 |
| WO | WO2008114458 | 9/2008 |
| WO | WO2008126064 A2 | 10/2008 |
| WO | WO2008130977 A1 | 10/2008 |
| WO | WO2009032449 A1 | 3/2009 |
| WO | WO2009134395 | 11/2009 |
| WO | WO2010129441 | 11/2010 |
| WO | WO2012068287 A2 | 5/2012 |
| WO | 2012112641 | 8/2012 |
| WO | WO2012112641 | 8/2012 |
| WO | WO20120112641 A1 | 8/2012 |
| WO | 2013018273 | 2/2013 |
| WO | WO20130018273 A1 | 2/2013 |
| WO | WO2013173446 | 11/2013 |
| WO | WO2005037471 A1 | 9/2014 |
| WO | 2015038494 | 3/2015 |
| WO | WO2015063552 | 5/2015 |
| WO | WO2018047011 A2 | 3/2018 |
| WO | WO2018047011 A2 | 5/2018 |
| WO | WO2018151680 A1 | 8/2018 |
| WO | WO2020092321 A1 | 5/2020 |
| WO | WO2020182193 A1 | 9/2020 |

OTHER PUBLICATIONS

Brief in Support of ABS Global, Inc. and Genus PLC's Rule 50(8) Motion for Judgment as a Matter of Law and Rule 59 Motion for a New Trial, *ABS Global, Inc. v. Inguran, LLC d/b/a Sexing Technologies*, Case No. 14-cv-503, United States District Court for the Western District of Wisconsin. Filed Sep. 2, 2016.

Imguran, LLC and XY, LLC's Response To ABS Global, Inc. and Genus PLC's Rule 50(8) Motion Fof Judgment as a Matter of Law and Rule 59 Motion for New Trial, pp. 9-28, 33-36, 73-74. Filed Sep. 23, 2016.

St's Response To ABS's Renewed Motion for Judgment as a Matter of Law That the Asserted Claims of The '987 Patent Are Invalid for Lack of Enablement And, in the Alternative, for a Hew Trial, *ABS Global, Inc. v. Inguran, LLC d/b/a Sexing Technologies*, Case No. 14-cv-503, United States District Court for the Western District of Wisconsin. Filed: Jul. 24, 2020.

Clinical Laboratory Instruments and In Vitro Diagnostic Reagents, Personnel Department of the State Food and Drug Administration, et al., pp. 17-21, China Medical Science and Technology Publishing House, Oct. 31, 2010).

Dicarlo "Continuous inertial focusing, ordering, and separation of particles in microchannels" BioMEMS Resource Center, Center for Engineering in Medicine and Surgical Services, Massachusetts General Hospital, Nov. 27, 2007, PNAS, 18892-18897, vol. 104, No. 48.

Dicarlo "Equilibrium Separation and Filtration of Particles Using Differential Inertial Focusing" BioMEMS Resource Center, Center for Engineering in Medicine and Surgical Services, Massachusetts General Hospital, Anal Chem 2008, 8, 2204-2211.

Dicarlo "Inertial Microfluidics: High-Throughput Focusing and Separation of Cells and Particles" BioMEMS Resource Center, Center for Engineering in Medicine, Massachusetts General Hospital, Twelfth International Conference on Miniaturized Systems for Chemistry and Life Sciences, Oct. 12-16, 2008, San Diego, California, USA.

China National Intellectual Property Administration, "Decision of Rejection," issued in connection with Chinese Patent Application No. 201480071952.0, dated March 4,2 019, 19 pages.

Jokinen, Ville, et al. "Durable superhydrophobicity in embossed CYTOP fluoropolymer micro and nanostructures", Colloids and Surfaces A: Physicochemical and Engineering Aspects, vol. 434, 2013, pp. 207-212.

Forsberg, Pontus, Fredrik Nikolajeff, and Mikael Karlsson, "Cassie-Wenzel and Wenzel-Cassie transitions on immersed superhydrophobic surfaces under hydrostatic pressure", Soft Matter, vol. 7, No. 1, 2011, pp. 104-109.

Lu, Hang, Martin A. Schmidt, and Klavs F. Jensen, "Photochemical reactions and on-line UV detection in microfabricated reactors", Lab on a Chip, vol. 1, No. 1, 2001, pp. 22-28.

Japan Patent Office, "Office Action," issued in connection with Japanese Patent Application No. 2019-513891, dated Jun. 24, 2021, 11 pages.

Brazilian Office Action, Application No. BR112019004727-1, dated Jul. 6, 2021, 4 pages.

Australian Office Action, Application No. 2017323502, dated Jun. 28, 2021, 6 pages.

China Office Action, Application No. 201780056064.5, dated Apr. 26, 2021, 8 pages.

China Office Action, Application No. 201780056064.5, dated Nov. 4, 2020 11 pages.

Europe Office Action, Application No. 17808998.3, dated Jul. 21, 2020.

Pedreira Carlos E et al: "Overview of clinical flow cytometry data analysis: recent advances and future challenges", Trends in Biotechnology, Elsevier Publications, Cambridge, GB, vol. 31, No. 7, Jun. 5, 2013.

China Patent Office, "The Third Office Action," issued in connection with China Patent Application No. 201480071952.0, dated Jul. 23, 2020, 23 pages.

Intellectual Property India, "Examination Report," issued in connection with Indian Patent Application No. 3429/DELNP/2015, dated Mar. 26, 2018, 6 pages.

European Patent Office, "European Search Report," issued in connection with patent application No. 20167363.9, dated Jul. 21, 2020, 9 pages.

Japan Patent Office, "Notice of Reasons for Refusal," issued in connection with Japan Patent Application No. 2018-220397, dated Aug. 5, 2020, 3 pages.

European Patent Office, "Examination Report," issued in connection with European Patent Application No. 16723498.8, dated Oct. 12, 2020, 6 pages.

European Patent Office, "European Search Report," issued in connection with European Patent Application No. 14168200.5, dated Mar. 20, 2015, 12 pages.

European Patent Office, "European Search Report," issued in connection with European Patent Application No. 17172322.4, dated Aug. 24, 2017, 8 pages.

European Patent Office, "European Search Report," issued in connection with European Patent Application No. 15160613.4, dated Jul. 24, 2015, 14 pages.

European Patent Office, "Communication pursuant to Article 94(3) EPC," issued in connection with European Patent Application No. 17172322.4, dated Aug. 14, 2018, 5 pages.

European Patent Office, "Communication pursuant to Article 94(3) EPC," issued in connection with European Patent Application No. 11193936.9, dated Dec. 11, 2015, 3 pages.

European Patent Office, "Communication pursuant to Article 94(3) EPC," issued in connection with European Patent Application No. 15160613.4, dated Jul. 11, 2016, 4 pages.

(56) References Cited

OTHER PUBLICATIONS

Hori et al., "Cell fusion by optical trapping with laser-involves contacting different cells with each other then imparting high voltage pulse to cells," WPI/Thompson, Dec. 27, 1991, Abstract, 1 page.
Japan Patent Office, "Notification of Reasons for Refusal," issued in connection with Japanese Patent Application No. 2016-185743, dated Jul. 3, 2018, 7 pages.
Japan Patent Office, "Final Notification of Reasons for Rejection," issued in connection with Japanese Patent Application No. 2011-256171, dated Oct. 28, 2014, 5 pages.
Japan Patent Office, "Decision for Grant," issued in connection with Japanese Patent Application No. 2015-091320, dated May 6, 2017, 7 pages.
Japan Patent Office, "Final Notification of Reasons for Rejection," issued in connection with Japanese Patent Application No. 2015-091320, dated Mar. 22, 2016, 22 pages.
Japan Patent Office, "Notification of Reasons for Refusal," issued in connection with Japanese Patent Application No. 2016-185743, dated Jul. 26, 2017, 2 pages.
Smith et al., "Inexpensive Optical Tweezers for Undergraduate Laboratories," Am. J. Phys., vol. 67, No. 1, Jan. 1999, 10 pages.
Takayama et al., "Patterning Cells and Their Environments Using Multiple Laminar Fluid Flows in Capillary Networks," Proceedings of National Academy of Sciences, vol. 96, 1999, 4 pages.
Ts'O, Basic Principles in Nucleic Acid Chemistry, National Library of Medicine, 1974, pp. 311-387.
International Preliminary Report on Patentability corresponding to International Patent Application No. PCT/US2013/050669, dated Jan. 28, 2016, 15 pages.
Supplementary European Search Report for U.S. Appl. No. 13/889,551, dated May 22, 2017, 12 pages.
State Intellectual Property Office of People's Republic of China, "Second Office Action," issued in connection with Chinese Patent Application No. 201380079634.4, dated Jun. 4, 2018, 14 pages.
Japan Patent Office, "Notice of Reasons for Rejection," issued in connection with Japanese Patent Application No. 2017-168904, dated Jul. 6, 2018, 3 pages.
State Intellectual Property Office of People's Republic of China, "Third Office Action," issued in connection with Chinese Patent Application No. 201380079634.4, dated Nov. 1, 2018, 20 pages.
Japanese Office Action for Application No. 2016-527978 dated Mar. 28, 2017, 8 pages.
State Intellectual Property Office of People's Republic of China, "First Office Action," issued in connection with Chinese Patent Application No. 201380079634.4, dated Jul. 28, 2017, 18 pages.
Indian Patent Application No. 3425/DELNP/2015 Pre-Grant Opposition, dated Dec. 4, 2020, 138 pages.
Indian Patent Application No. 3425/DELNP/2015 Pre-Grant Opposition, dated Jul. 21, 2020, 59 pages.
Indian Patent Application No. 3425/DELNP/2015 Pre-Grant Opposition, dated Jul. 21, 2020, 96 pages.
Indian Patent Application No. 3425/DELNP/2015 Pre- Grant Opposition, dated Jul. 2, 2020, 137 pages.
Sell, "Cellular Origin of Cancer: Dedifferentiation or Stem Cell Maturation Arrest?", Environmental Health Perspectives, vol. 101, Suppl. 5, 1993, p. 15-26.
Shapiro et al., "Pratical Flow Cytometry," Fourth Edition, New Jersey: John W. Wiley & Sons, 2003, 733 pages.
Sharpe et al.,"Advances in Flow Cytometry for Sperm Sexing," Theriogenology, vol. 71, 2009, pp. 4-10.
Short, "Raman Spectroscopy Detects Biochemical Changes Due to Proliferation in Mammalian Cell Cultures," Biophysical Journal, vol. 88, Jun. 2005, pp. 427 4-4288.
USPTO, "Non-Final Office Action," issued in connection with U.S. Appl. No. 15/226,899, dated Apr. 12, 2018, 14 pages.
USPTO, "Notice of Allowance," issued in connection with U.S. Appl. No. 15/226,899, dated Aug. 23, 2018, 5 pages.
USPTO, "Notice of Allowance," issued in connection with U.S. Appl. No. 15/226,899, dated Sep. 20, 2018, 6 pages.

USPTO, "Final Office Action," issued in connection with U.S. Appl. No. 15/174,681, dated Jan. 2, 2018, 15 pages.
USPTO, "Final Office Action," issued in connection with U.S. Appl. No. 15/174,681, dated Sep. 14, 2018, 17 pages.
USPTO, "Non-Final Office Action," issued in connection with U.S. Appl. No. 15/174,681, dated May 4, 2017, 13 pages.
USPTO, "Non-Final Office Action," issued in connection with U.S. Appl. No. 15/174,681, dated Apr. 5, 2018, 16 pages.
USPTO, "Notice of Allowance," issued in connection with U.S. Appl. No. 15/174,681, dated Nov. 27, 2018, 5 pages.
USPTO, "Final Office Action," issued in connection with U.S. Appl. No. 13/298,148, dated Oct. 18, 2013, 46 pages.
USPTO, "Non-Final Office Action," issued in connection with U.S. Appl. No. 13/298,148, dated Feb. 5, 2013, 66 pages.
USPTO, "Notice of Allowance," issued in connection with U.S. Appl. No. 13/298,148, dated Sep. 19, 2014, 9 pages.
USPTO, "Office Action," issued in connection with U.S. Appl. No. 13/298,148, dated Sep. 28, 2012, 5 pages.
USPTO, "Final Office Action," issued in connection with U.S. Appl. No. 13/894,831, dated Sep. 10, 2015, 11 pages.
USPTO, "Final Office Action," issued in connection with U.S. Appl. No. 13/894,831, dated Jun. 15, 2017, 19 pages.
USPTO, "Non-Final Office Action," issued in connection with U.S. Appl. No. 13/894,831, dated Dec. 23, 2014, 11 pages.
USPTO, "Non-Final Office Action," issued in connection with U.S. Appl. No. 13/894,831, dated Oct. 5, 2016, 17 pages.
USPTO, "Notice of Allowance," issued in connection with U.S. Appl. No. 13/894,831, dated Apr. 1, 2016, 8 pages.
USPTO, "Notice of Allowance," issued in connection with U.S. Appl. No. 13/894,831, dated Sep. 5, 2017, 9 pages.
Wang et al., Detection of endogenous biomolecules in Barrett's esophagus by Fourier transform infrared spectroscopy, PNAS, vol. 104, No. 40, Oct. 2, 2007, p. 15864-15869.
Webster, Merriam, "Definition of "successive," Merriam Webster's Online Dictionary, accessed at http://www.merriamwebster.com/dictionary/successive," Jun. 18, 2013, 1 page.
Weida et al., "Quantum Cascade Laser Based Replacement for FTIR Microscopy," http://www.daylightsolutions. ::om/assets/003/5308.pdf, accessed online Aug. 2, 2012, 7 pages.
International Bureau, "International Preliminary Report on Patentability," issued in connection with International Patent Application No. PCT/IB2017/001289, dated Mar. 21, 2019, 12 pages.
International Search Report and Written Opinion for Application Serial No. PCT/IP2017/001289, dated Apr. 3, 2018, 21 pages.
Mehrnoush Malek et al: flowDensity: reproducing manual gating of flow cytometry data by automated density-based cell population identification11, Bioinformatics., vol. 31, No. 4, Oct. 16, 2014 (Oct. 16, 2014), pp. 606-607.
International Search Report and Written Opinion for Application Serial No. PCT/IB2018/001641, dated Jun. 25, 2020 4 pages.
China Patent Office, "The Fourth Office Action," issued in connection with China Patent Application No. 201480071952.0, dated Jan. 3, 2021, 25 pages.
Japan Patent Office, "Notice of Reasons for Refusal," issued in connection with Japan Patent Application No. 2019-088655, dated Oct. 13, 2020, 5 pages.
Johnson LA et al., Flow sorting of X and Y chromosome-bearing spermatozoa into two populations, Gamete Research. Jan. 16, 1987(1):1-9. (Johnson 1987).
Paape et al., Flow Cytometry: A Versatile Tool for Studies on Cells From Domestic Animals, National Cytometry Symposium, Abstract Only, Dec. 14, 1997, https://www.ars.usda.gov/research/publications/publication/?seqNo115=86408.
Keij, J.F. et al., "High-Speed Photodamage Cell Selection Using a Frequency-Doubled Argon Ion Laser." Cytometry 19 (1995): 209-216. (Keij 1995).
Keij, J.F., "Introduction to High-Speed Flow Sorting." Flow and Image Cytometry. Series H: Cell Biology, 95 (1996) 213-227. (Keij 1996).
Johnson LA, Welch GR, Rens W. "The Beltsville sperm sexing technology: high-speed sperm sorting gives improved sperm output for in vitro fertilization and AI" J Anim Sci 1999. 77:213-220.

(56) References Cited

OTHER PUBLICATIONS

Counterclaim Defendants ABS Global Inc.'s And Genus PLC's Invalidity Contentions. *ABS Global, Inc., v. Inguran, LLC D/B/A Sexing Technologies and. XY, LLC v. Genus PLC.* Case No. 14-cv-503 United States District Court for the Western District of Wisconsin; pp. 1, 43-114, and 168-177.
ABS Global, Inc. And Genus PLC's Renewed Motion For Judgment As A Matter Of Law That The Asserted Claims Of The '987 Patent Are Invalid For Lack Of Enablement And, In The Alternative, For A New Trial. *ABS Global, Inc. v. Inguran, LLC & XY, LLC v. Genus PLC.* Case: 3:14-cv-00503-wmc. Filed on Jul. 3, 2020.
Brief in Support of ABS Global, Inc. And Genus PLC's Motion for Judgment as A Matter of Law That the Asserted Claims Of The '987 Patent Are Not Enabled. *Inguran, LLC d/b/a Stgenetics, XY, LLC, and Cytonome/St, LLC,* Plaintiffs/Counterclaim-Defendants, v.*ABS Global, Inc., Genus PLC, and Premium Genetics (UK) LTD,* Defendants/Counterclaim-Plaintiffs. Case: 3:17-cv-00446-wmc. Filed Sep. 6, 2019.
ABS Global, Inc. And Genus Plc Renewed Motion for Judgment As A Matter Of Law That The Asserted Claims Of The 987 Patent Are Invalid For Lack Of Enablement And, In The Alternative, For A New Trial. *Inguran, LLC d/b/a Stgenetics, XY, LLC, and Cytonome/St, LLC,* Plaintiffs/Counterclaim-Defendants, v.*ABS Global, Inc., Genus PLC, and Premium Genetics (UK) Ltd,* Defendants/Counterclaim-Plaintiffs. Case: 3:17-cv-00446-wmc. filed Jul. 3, 2020.
ABS Global, Inc. And Genus PLC's Reply In Support Of Their Renewed Motion For Judgment As A Matter Of Law That The Asserted Claims Of The '987 Patent Are Invalid For Lack Of Enablement And, In The Alternative, For A New Trial. *Inguran, LLC d/b/a Stgenetics, XY, LLC, and Cytonome/St, LLC,* Plaintiffs/Counterclaim-Defendants, v. *ABS Global, Inc., Genus PLC, and Premium Genetics (UK) LTD,* Defendants/Counterclaim-Plaintiffs. Case: :17-cv-00446-wmc Filed Aug. 17, 2020.
ABS Global, Inc. and Genus PLC's Motion For Judgment As A Matter Of Law That The Asserted Claims Of The 987 And '092 Patents Are Invalid. *ABS Global, Inc.,* Plaintiff/Counterclaim Defendant, v. *Inguran, LLC d/b/a Sexing Technologies,* Defendant/Counterclaim Plaintiff, *and XY, LLC,* Intervenor-Defendant/Counterclaim Plaintiff, v. *Genus PLC,* Counterclaim Defendant. Case: 3:14-cv-00503-wmc. Filed August 9, 2016.
ABS Global, Inc. and Genus PLC's Rule 50(8) Motion For Judgment As A Matter Of Law And Rule 59 Motion For A New Trial. *ABS Global, Inc.,* Plaintiff/Counterclaim Defendant, v. *Inguran, LLC d/b/a Sexing Technologies,* Defendant/Counterclaim Plaintiff, *and XY, LLC,* Intervenor-Defendant/Counterclaim Plaintiff, v. *Genus PLC,* Counterclaim Defendant. Case: 3:14-cv-00503-wmc. Filed Sep. 2, 2016.
Opinion and Order of the United States District Court For The Western District Of Wisconsin. Plaintiff/Counterclaim Defendant, v. *Inguran, LLC d/b/a Sexing Technologies,* Defendant/Counterclaim Plaintiff, *and XY, LLC,* Intervenor-Defendant/Counterclaim Plaintiff, v. *Genus PLC,* Counterclaim Defendant Case: 3:14-cv-00503-wmc. riled Mar. 31, 2017.
Appeal from the United States District Court for the Western District of Wisconsin. No. 14-CV-503. *ABS Global, NC.,* Plaintiff/Counterclaim Defendant-Appellant, *and Genus PLC,* Counterclaim Defendant-Appellant, v. *Inguran, LLC, doing business as Sexing Technologies,* Defendant/Counterclaim Plaintiff-Appellee, *and XY, LLC,* Intervening Defendant/Counterclaim Plaintiff-Appellee. Case: 3:14-cv-00503-wmc. Filed: Mar. 8, 2019.
Judge's Opinion & Order in Case No. 14-cv-503-wmc. Plaintiff/Counterclaim Defendant, v. *Inguran, LLC b/a Sexing Technologies,* Defendant/Counterclaim Plaintiff, *and XY, LLC,* Intervenor-Defendant/Counterclaim Plaintiff, v. *Genus PLC,* Counterclaim Defendant. Case: 3:14-cv-00503-wmc. Filed Jul. 21, 2016.
ABS Global Inc. and Genus PLC's Reply in Support of Their Motion for Claim Construction and Partial Summary Judgment, *ABS Global, Inc. v. Inguran, LLC d/b/a Sexing Technologies,* Case No. 14-cv-503. United States District Court for the Western District of Wisconsin. Mar. 7, 2016.

Brazilian Office Action, Application No. BR122017012966-0, dated Jun. 2, 2020, 2020, 6 pages.
USPTO, "Non-Final Office Action," issued in connection with U.S. Appl. No. 17/403,642, dated Nov. 29, 2021, 13 pages.
Intellectual Property India, "Examination Report," issued in connection with Indian Patent Application No. 201917009874, dated Nov. 25, 2021, 6 pages.
Australian Office Action, Application No. 2017323502, dated Oct. 22, 2021, 6 pages.
Jun et al. "Detecting and estimating contamination of human DNA samples in sequencing and array-based genotype data." The American Journal of Human Genetics 91.5 (2012): 839-848.
International Searching Authority, "International Search Report and Written Opinion," issued in connection with International Patent Application No. PCT/US21/56094, dated Mar. 16, 2022, 22 pages.
USPTO, "Notice of Allowance," issued in connection with U.S. Appl. No. 17/496,469, dated May 10, 2022, 54 pages.
China National Intellectual Property Administration, "Notice of Allowance," issued in connection with Chinese Patent Application No. 201480071952.0, dated Mar. 21, 2022, 3 pages.
Intellectual Property India, "Examination Report," issued in connection with Indian Patent Application No. 3425/DELNP/2015, dated Jan. 20, 2020, 6 pages.
Al-Holy et al., "The Use of Fourier Transform Infrared Spectroscopy to Differentiate *Escherichia coli* O157:H7 from Other Bacteria Inoculated Into Apple Juice," Food Microbiology, vol. 23, 2006, 162-168.
Alberts et al., "Molecular Biology of the Cell, 5th edition," New York: Garland Science, 2008, p. 1293.
Barcot et al., "Investigation of Spermatozoa and Seminal Plasma by Fourier Transform Infrared Spectroscopy," Applied Spectroscopy, vol. 61, No. 3, Mar. 2007, pp. 309-313.
Bassan et al; "Reflection Contributions to the Dispersion Artefact in FTIR Spectra of Single Biological Cells," Analyst, vol. 134, Apr. 9, 2009, pp. 1171-1175.
Bassan et al; "Resonant Mie Scattering in Infrared Spectrascopy of Biological Materials—Understanding the Dispersion Artefact'," Analyst, vol. 134, 2009, pp. 1586-1593.
Bassan et al; "Resonant Mie Scattering {RMieS) Correction of Infrared Spectra From Highly Scattering Biological Samples," Analyst, vol. 135, No. 2, Feb. 2010, pp. 268-277.
Belkin et al.; "Intra-Cavity Absorption Spectroscopy with Narrow-Ridge Microfluidic Quantum Cascade Lasers,"Applies Express, vol. 15, No. 18, Sep. 3, 2007, pp. 11262-11271.
Boustany et al.; "Microscopic Imaging and Spectroscopy with Scattered Light," Annual Review of Biomedical Engineering, vol. 12, 2010, pp. 285-314.
Chan et al.; "Nondestructive Identification of Individual Leukemia Cells by Laser Trapping Raman Spectroscopy," Analytical Chemistry, vol. 80, No. 6, Mar. 15, 2008, 8 pages.
Chan et al.; "Label-Free Biochemical Characterization of Stem Cells Using Vibrational Spectroscopy," Journal of Biophotonics vol. 2, No. 11, Aug. 5, 2009, pp. 656-668.
Chan et al.; "Label-Free Separation of Human Embryonic Stem Cells {hESCs) and their Cardiac Derivatives using Raman Spectroscopy," Lawrence Livermore Journal, LLNL-JRNL-406938, Sep. 11, 2008, 30 pages.
Chen et al..; "Synchrotron Infrared Measurements of Protein Phosphorylation in Living Single PC12 Cells during Neuronal Differentiation," Analytical Chemistry, vol. 84, 2012, pp. 4118-4125.
Cheng et al., "Laser-Scanning Coherent Anti-Strokes Raman Scattering Microscopy and Applications to Cell Biology," Biophysical Journal, vol. 83, Jul. 2002, pp. 502-509.
Cho et al., "Passively Driven Integrated Microfluidic System for Separation of Motile Sperm," Analytical Chemistry, vol. 75, Apr. 1, 2003, Abstract.
Cho et al., A Microfluidic Device For Separating Motile Sperm From Nonmotile Sperm Via Inter-Streamline.
Cleary et al., "Infrared Surface Plasmon Resonance Biosensor," OSA Biomed, Miami, Florida, Apr. 2010, 6 pages.

(56) References Cited

OTHER PUBLICATIONS

Dousseau et al., "On the Spectral Subtraction of Water from the FT-IR Spectra of Aqueous Solutions of Proteins," Applied Spectroscopy, vol. 43, No. 3, 1989, pp. 538-542.

Downes et al., "Optical Spectroscopy for Noninvasive Monitoring of Stem Cell Differentation," Journal of Biomedicine and Biotechnology, vol. 2010, Article ID 101864, 2010, 10 pages.

Ege, "Organic Chemistry: Structure and Reactivity," Fifth Edition, Boston, MA, Houghton Mifflin Company, 2004, pp. 453-457.

European Patent Office, "Extended European Search Report," issued in connection with European Patent Application No. 11841869.8, dated Feb. 15, 2018, 9 pages.

Fu et al., "A Microfabricated Fluorescence-Activated Cell Sorter," Nature Biotechnology, vol. 17, Nov. 1999, pp. 1109-1111.

Green et al., "Flow Cytometric Determination of Size and Complex Refractive Index for Marine Particles: Comparison with Independent and Bulk Estimates," Applied Optics, vol. 42, No. 3, Jan. 20, 2003, pp. 526-541.

Harvey et al., "Discrimination of Prostate Cancer Cells by Reflection Mode Fi Ir Photoacoustic Spectroscopy," The Analyst, vol. 132, 2007, pp. 292-295.

Herzenberg et al., "Fluorescence-activated Cell Sorting," Scientific American, vol. 234, Mar. 1976, pp. 108-117.

Holman et al., "Synchrotron-Based FTIR Spectromicroscopy: Cytotoxicity and Heating Considerations," Journal of Biological Physics, vol. 29, 2003, pp. 275-286.

Holman et al., "IR Spectroscopic Characteristics of Cell Cycle and Cell Death Probed by Synchrotron Radiation Based Fourier Transform IR Spectromicroscopy," Biopolymers (Biospectroscopy) vol. 57, 2000, pp. 329-335.

Holman et al., "Tracking Chemical Changes in a Live Cell: Biomedical Applications of SR-FTIR Spectromicroscopy,"Lawrence Berkeley National Laboratory, http://escholarship.org/uc/item/9k185794, Berkeley, CA Jul. 25, 2002, 34 pages.

Huser et al., "Raman Spectroscopy of DNA Packaging in Individual Human Sperm Cells Distinguishes Normal From Abnormal Cells," Journal of Biophotonics, vol. 2, No. 5, 2009, pp. 322-332.

Intel, "Intel C-bank Tunable Laser, Performance and Design," White Paper, May 2003, 14 pages.

International Searching Authority, "International Search Report and Written Opinion," International Patent Application No. PCT/US2013/41123, dated Aug. 19, 2013, 12 pages.

International Search Authority, "International Preliminary Report on Patentability," International Patent Application No. PCT/US2011/061046, dated May 30, 2013, 7 pages.

International Searching Authority, "International Preliminary Report on Patentability," International Patent Application No. PCT/US2013/041123, dated Nov. 18, 2014, 7 pages.

Japan Patent Office, "Office Action," issued in connection with Japanese Patent Application No. 2013-539983, dated Jul. 8, 2015, 6 pages.

Japan Patent Office, "Office Action," issued in connection with Japanese Patent Application No. 2013-539983, dated Jul. 2, 2016, 6 pages.

Japan Patent Office, "Office Action," issued in connection with Japanese Patent Application No. 2016-198323, dated Oct. 2, 2017, 3 pages.

Japan Patent Office, "Office Action," issued in connection with Japanese Patent Application No. 2016-198323, dated Jul. 25, 2018, 9 pages.

Lee et al., "DFB Quantum Cascade Laser Arrays," IEEE Journal of Quantum Electronics, vol. 45, No. 5, May 9, pp. 554-565.

Ibbus et al., "Incidence of Chromosome Aberrations in Mammalian Sperm Stained with Hoechst 33342 and UV-aser Irradiated During Flow Sorting," Mutation Research, vol. 182, 1987, pp. 265-274.

Malone, Jr., "Infrared Microspectroscopy: A Study of the Single Isolated Bread Yeast Cell," Thesis, The Ohio State University, 2010, 162 pages.

Meister et al., "Confocal Raman Microspectroscopy as an Analytical Tool to Assess the Mitochondral Status in Human Spermatozoa," Analyst, vol. 135, 2010, pp. 1370-1374.

Miyamoto et al., "Label-free Detection and Classification of DNA by Surface Vibration Spectroscopy in Conjugation with Electrophoresis," Applied Physics Letters, vol. 86, No. 053902, 2005, 3 pages.

Mohlenhoff et al., "Mie-Type Scattering and Non-Beer-Lambert Absorption Behavior of Human Cells in Infared Microspectroscopy," Biophysical Journal, vol. 88, May 2005, pp. 3635-3640.

Montag et al., "Laser-induced Immobilization and Plasma Membrane Permeabilization in Human Spermatozoa," Human Reproduction, vol. 15, No. 4, 2000, pp. 846-852.

Mourant et al., "Methods for Measuring the Infrared Spectra of Biological Cells," Physics in Medicine and Biology, vol. 48, 2003, pp. 243-257.

Van Munster, "Interferometry in Flow to Sort Unstained X-and Y-Chromosome-Bearing Bull Spermatozoa,"Cytometry, vol. 47, 2002, pp. 192-199.

Rajagopalan et al., "Aneuploidy and Cancer," Nature, vol. 432, Nov. 2004, pp. 338-341.

Ropcke et al., "Application of Mid-Infrared Tuneable Diode Laser Absorption Spectroscopy to Plasma Diagnostics: A Review," Plasma Sources Science and Technology, vol. 15, 2006, S148-S168.

Schaden et al., "Quantum Cascade Laser Modulation for Correction of Matrix-Induced Background Changes in Aqueous Samples," Applied Physics B, vol. 86, 2007, pp. 347-351.

Sandt et al., "Identification of Spectral Modifications Occurring during Reprogramming of Somatic Cells," PLoS ONE, vol. 7, Issue 4, e30743, Apr. 2012, 7 pages.

International Searching Authority, "International Search Report," issued in connection with International Patent Application No. PCT/IB2014/001425, dated Apr. 28, 2015, 6 pages.

Herweijer et al., "High-Speed Photodamage Cell Selection Using Bromodeoxyuridine/Hoechst 33342 Photosensitized Cell Killing," Cytometry, vol. 9, No. 2, Mar. 1988, pp. 143-149, 7 pages.

Johnson et al., "Sex Preselection: High-Speed Flow Cytometric Sorting of X and Y Sperm for Maximum Efficiency," Theriogenology, vol. 52, No. 8, Dec. 1999, pp. 1323-1341, 19 pages.

Bazyar et al., "Compact 151W green laser with U-type resonator for prostate surgery," Optics & Laser Technology, vol. 47, Apr. 2013, pp. 237-241, 6 pages.

Khodjakov et al., "Views and Review—A Synergy of Technologies: Combining Laser Microsurgery With Green Fluorescent Protein Tagging," Cell Motility and the Cytoskeleton, vol. 38, 1997, pp. 311-317, 11 pages.

Keij et al., "Chaper 22—High-Speed Photodamage Cell Sorting: An Evaluation of the ZAPPER Prototype," Methods in Cell Biology, vol. 42, 1994, pp. 371-386, 16 pages.

International Searching Authority, "Written Opinion," issued in connection with International Patent Application No. PCT/US2013/050669, dated Mar. 7, 2014, 13 pages.

Fulwyler, "Hydrodynamic Orientation of Cells," The Journal of Histochemistry and Cytochemistry, vol. 25, No. 7, 1977, pp. 781-783, 3 pages.

Kachel et al., "Uniform Lateral Orientation, Caused by Flow Forces, of Flat Particles in Flow-Through Systems," The Journal of Histochemistry and Cytochemistry, vol. 25, No. 7, 1977, pp. 774-780, 7 pages.

United States Patent and Trademark Office, "Office Action," issued in connection with U.S. Appl. No. 15/033,001, dated Jun. 15, 2018, 7 pages.

United States Patent and Trademark Office, "Notice of Allowance," issued in connection with U.S. Appl. No. U.S. Appl. No. 13/943,322, dated Sep. 12, 2014, 16 pages.

State Intellectual Property Office of People's Republic of China, "Notification of the First Office Action," issued in connection with Chinese Patent Application No. 201480071952.0, dated Mar. 16, 2018.

International Searching Authority, "Written Opinion," issued in connection with International Patent Application No. PCT/IB2014/001425, dated Apr. 28, 2015, 10 pages.

(56) References Cited

OTHER PUBLICATIONS

Japan Patent Office, "Notification of Reasons for Refusal," issued in connection with Japanese Patent Application No. 2016-551082, dated Apr. 24, 2018, 9 pages.
Mew Zealand Intellectual Property Office, "First Examination Report," issued in connection with New Zealand Patent Application No. 720575, dated Sep. 9, 2016, 5 pages.
Mew Zealand Intellectual Property Office, "Further Examination Report," issued in connection with New Zealand Patent Application No. 720575, dated Apr. 28, 2017, 3 pages.
Canadian Office Action, Application No. 2,929,275, dated May 4, 2020, 8 pages.
USPTO, "Non-Final Office Action," issued in connection with U.S. Appl. No. 16/741,608, dated Mar. 18, 2022, 12 pages.
USPTO, "Notice of Allowance," issued in connection with U.S. Appl. No. 17/412,789, dated Mar. 21, 2022, 30 pages.
USPTO, "Notice of Allowance," issued in connection with U.S. Appl. No. 17/458,947, dated Mar. 31, 2022, 30 pages.
European Patent Office, "Extended European Search Report," issued in connection with patent application No. 19182993.6, dated Oct. 21, 2019, 11 pages.
USPTO, "Final Office Action," issued in connection with U.S. Appl. No. 17/403,642, dated Mar. 4, 2022, 14 pages.
Australian Office Action, Application No. 2021200818, dated Mar. 4, 2022, 3 pages.
China Patent Office, "The Fifth Office Action," issued in connection with China Patent Application No. 2014800719520, dated Oct. 20, 2021, 7 pages.
USPTO, "Non-Final Office Action," issued in connection with U.S. Appl. No. 17/458,947, dated Dec. 15, 2021, 9 pages.
USPTO, "Notice of Allowance," issued in connection with U.S. Appl. No. 16/864,514, dated Jan. 3, 2022, 24 pages.
USPTO, "Notice of Allowance," issued in connection with U.S. Appl. No. 16/419,756, dated Jan. 12, 2022, 16 pages.
USPTO, "Non-Final Office Action," issued in connection with U.S. Appl. No. 16/852,303, dated Jan. 6, 2022, 27 pages.
Intellectual Property India, "Examination Report," issued in connection with Indian Patent Application No. 202147003036, dated Jan. 4, 2022, 5 pages.
Di Carlo, "Inertial microfluidics." Lab on a Chip 9.21 (2009): 3038-3046.
Intellectual Property India, "Examination Report," issued in connection with Indian Patent Application No. 202017054203, dated Jan. 7, 2022, 5 pages.
Japan Patent Office, "Reconsideration Report by Examiner before Appeal," issued in connection with Japanese Patent Application No. 2016-551082, dated Jul. 12, 2019, 17 pages.
Altendorf et al., "Results Obtained Using a Prototype Microfluidics-Based Hematology Analyzer," in Proceedings of the microTAS 1998 Symposium, 73-76 (Oct. 1998).
Nieuwenhuis et al., "Particle-Shape Sensing-Elements for Integrated Flow Cytometer," in Proceedings of the microTAS 2001 Symposium, 357-358 (Oct. 21, 2001).
Nieuwenhuis et al. "Virtual Flow Channel: A Novel Micro-fluidics System with Orthogonal, Dynamic Control of Sample Flow Dimensions," in Proceedings of the microTAS 2002 Symposium, vol. 1, 103-105 (Nov. 3, 2002).
Nieuwenhuis, J., et al. "Integrated flow-cells for novel adjustable sheath flows." Lab Chip, 2003, 3, 56-61 (Mar. 2003.
Shoji, S., et al. "Design and fabrication of micromachined chemical/biochemical systems." RIKEN Rev., vol. 36, pp. 8-11, 2001.
Lin, C., et al. "A Novel Microflow Cytometer with 3-dimensional Focusing Utilizing Dielectrophoretic and Hydrodynamic Forces." The Sixteenth Annual International Conference on Micro Electro Mechanical Systems, 2003. MEMS-03 Kyoto IEEE, Kyoto, Japan, 2003, pp. 439-442.
Miyake et al., "A Development of Micro Sheath Flow Chamber," in Proceedings of the IEEE Micro Electro Mechanical Systems Workshop 1991, 265-270 (Jan. 1991).

Tashiro et al., "Design and Simulation of Particles and Biomolecules Handling Micro Flow Cells with Three-Dimensional Sheath Flow," in Proceedings of the microTAS 2000 Symposium, 209-212 (May 14, 2000).
Weigl, B. et al. "Design and Rapid Prototyping of Thin-Film Laminate-Based Microfluidic Devices." Biomedical Microdevices, 3:4, pp. 267-274, 2001.
Blankenstein, G. et al. "Modular concept of a laboratory on a chip for chemical and biochemical analysis." Biosensors & Bioelectronics, vol. 13. No 3-4, pp. 427-438, 1998.
Shapiro, Practical Flow Cytometry, 15-17, 133-135 (3rd ed. 1995).
Shapiro, Practical Flow Cytometry, 55-57, 166-169 (4th ed. 2003).
International Search Report for PCT Patent Application No. PCT/IB2014/001425 dated Apr. 28, 2015.
Herweijer, H. et al., "High Speed Photodamage Cell Selection Using Bromodeoxyuridine/Hoechst 33342 Photosensitized Cell Killing", Radiobiological Institute TNO, Rotterdam, The Netherlands, Jun. 1, 1987.
Johnson, L.A., et al., "Sex Preselection: High-Speed Flow Cytometric Sorting of X and Y Sperm for Maximum Efficiency" U.S. Dept. of Agriculture, Beltsville, MD, Sep. 23, 1999.
Bazyer H., et al., "Views and Reviews—Compact 151W Green Laser with U-Type Resonator for Prostate Surgery", Optics & Laser Technology, vol. 47, Apr. 27, 2013, 237-241.
Keij, J. et al., "High-Speed Photodamage Cell Sorting: An Evaluation of the ZAPPER Prototype", Methods in Cell Biology, 1994; pp. 371-386, vol. 42, Chapter 22, Academic Press, Inc.
International Search Report and Written Opinion dated Mar. 7, 2014 in connection with PCT/US2013/050669.
Kachel, V, et al., "Uniform Lateral Orientation, caused by Flow Forces, of Flat Particles in Flow-Through Systems", The Journal of Histochemistry and Cytochemistry, vol. 25, No. 7, pp. 774-780, 1977.
Notice of Allowance issued in U.S. Appl. No. 13/943,322 dated Sep. 12, 2014.
Fulwler, M., "Hydrodynamic Orientation of Cells", The Journal of Histochemistry and Cytochemistry, vol. 25, No. 7, pp. 781-783, 1977.
Khodjakov A., et al., "A Synergy of Technologies: Combining Laser Microsurgery with Green Fluorescent Protein Tagging", Cell Motility and the Cytoskeleton 38:311-317 (1997), Division of Molecular Medicine and Department of Biomedical Sciences, Albany, New York.
Australian Office Action, Application No. 2019202882, dated Mar. 26, 2020, 3 pages.
Brazilian Office Action, Application No. BR122017012966-0, dated Jun. 2, 2020, 6 pages.
Japan Patent Office, "Reconsideration Report by Examiner before Appeal," issued in connection with Japanese Patent Application No. 2016-551082, dated Jul. 12, 2019, 17 pp. 20090114285.
China National Intellectual Property Administration, "Second Office Action," issued in connection with Chinese Patent Application No. 201480071952.0, dated Nov. 26, 2018, 34 pages.
China National Intellectual Property Administration, "Decision of Rejection," issued in connection with Chinese Patent Application No. 201480071952.0, dated Mar. 4, 2019, 19 pages.
IP Australia, "Examination Report No. 1 for Standard Patent Application," issued in connection with Australian Patent Application No. 2014343391, dated Sep. 4, 2018, 3 pages.
International Preliminary Report on Patentability, issued in connection with application PCT/IB/001425, May 3, 2016, 11 pages.
Japan Patent Office, "Non Final Notice of Reasons for Rejection," issued in connection with Japanese Patent Application No. 2016-551082, dated Apr. 24, 2018, 5 pages.
New Zealand IP Office, "First Examination Report," issued in connection with New Zealand Patent Application No. 720575, dated Sep. 9, 2016, 5 pages.
New Zealand IP Office, "Further Examination Report," issued in connection with New Zealand Patent Application No. 720575, dated Apr. 28, 2017, 3 pages.

(56) References Cited

OTHER PUBLICATIONS

State Intellectual Property Office of People'S Republic of China, "Notification of First Office Action," issued in connection with Chinese Patent Application No. 201480071952.0, dated Mar. 16, 2018, 31 pages.
New Zealand IP Office, "Further Examination Report," issued in connection with New Zealand Patent Application No. 735496, dated Aug. 31, 2018, 2 pages.
Drobnis et al., Cold Shock Damage is due to Lipid Phase Transitions in Cell Membranes: A Demonstration Using Sperm as a Model, The Journal of Experimental Zoology, 1993, 265:432-437.
Way et al., Comparison of four staining methods for evaluating acrosome status and viability of ejaculated and cauda epididymal bull spermatozoa, Theriogenology, 1995, 43(8): 1301-1316.
Marian et al., Hypo-osmotic Shock Induces an Osmolality-dependent Permeabilization and Structural Changes in the Membrane of Carp Sperm, 1993, 41(2):291-297.
Molecular Probes Inc., Product Information, Influx Pinocylic Cell-Loading Reagent (1-14402), Revised Feb. 1, 2001, 1-7.
Parks, Processing and Handling Bull Semen for Artificial Insemination—Don't Add Insult to Injury!, Department of Animal Sciences, Cornell University, 2001, retrieved on May 29, 2015, retrieved from the internet: http://www/ansci.cornell.edu/bullsemen.pdf.
Mammal (Online Datasheet), Wikipedia, 2003, retrieved on Aug. 13, 2018, retrieved from internet: http://web.archive.org/web/20031230110838/hllps://en.wikipedia.org/wiki/Mammal.
International Searching Authority, "International Search Report and Written Opinion," issued in connection with International Patent Application No. PCT/IB2016/000295, dated Oct. 14, 2016, 19 pages.
International Bureau, "International Preliminary Report on Patentability," issued in connection with International Patent Application No. PCT/IB2016/000295, dated Aug. 31, 2017, 14 pages.
Japan Patent Office, "Office Action," issued in connection with Japanese Patent Application No. 2017-543990, dated Jul. 31, 2019, 23 pages.
Di Carlo et al. "Equilibrium Separation and Filtration of Particles Using Differential Inertial Focusing" Anal. Chem. 2008, 30, 2204-2211 (Year: 2008).
"Hydraulic Diameter", Neutrium, Apr. 1, 2012, https://neutrium.net/fluid-flow/hydraulic-diameter/ (Year: 2012).
Gossett et al. "Particle Focusing Mechanisms in Curving Confined Flows" Anal. Chem. 2009, 81, 8459-8465 (Year 2009).
Di Carlo et al. "Continuous inertial focusing, ordering, and separation of particles in microchannels" PNAS Nov. 27, 2007 vol. 104 No. 48 18893 (Year: 2007).
Kang, et al. "Effect of an osmotic differential on the efficiency of gene transfer by electroporation of fish spermatozoa" Aquaculture 173.1 4 (1999): 297-307. (Year: 1999).
Rieth et al. "Electroporation of bovine spermatozoa to carry DNA containing highly repetitive sequences into oocytes and detection of homologous recombination events." Molecular Reproduction and Development: Incorporating Gamete Research 57.4 (2000): 338-345.
Chamberland et al. "The effect of heparin on motility parameters and protein phosphorylation during bovine sperm capacitation."Theriogenology 55.3 (2001): 823-835. (Year: 2001).
Chan, et al. "Luminescent quantum dots for multiplexed biological detection and imaging." Current opinion in biotechnology 13.1 (2002): 40-46. (Year: 2002).
USPTO, "Non-Final Office Action," issued in connection with U.S. Appl. No. 16/561,146, dated Jan. 21, 2022, 14 pages.
USPTO, "Non-Final Office Action," issued in connection with U.S. Appl. No. 17/496,469, dated Jan. 28, 2022, 13 pages.
USPTO, "Final Office Action," issued in connection with U.S. Appl. No. 16/741,608, dated Jun. 13, 2022, 11 pages.
USPTO, "Non-Final Office Action," issued in connection with U.S. Appl. No. 17/403,642, dated Jul. 13, 2022, 7 pages.
USPTO, "Final Office Action," issued in connection with U.S. Appl. No. 16/852,303, dated May 27, 2022, 48 pages.
International Search Report and Written Opinion for Application Serial No. PCT/US2021/059148, dated May 4, 2022, 15 pages.
European Patent Office, "Communication under Rule 71(3) EPC," issued in connection with European Patent Application No. 16723498.8, dated May 18, 2022, 54 pages.
European Patent Office, "Examination Report," issued in connection with U.S. Appl. No. 20/167,363 9, dated Mar. 22, 2022, 4 pages.
European Patent Office, "Examination Report," issued in connection with patent application No. 19182993.6, dated May 10, 2022, 8 pages.
Ip Australia, "Notice of Acceptance for Patent Application," issued in connection with Australian Patent Application Mo. 2021200818, dated Jun. 1, 2022, 3 pages.
New Zealand IP Office, "First Examination Report," issued in connection with New Zealand Patent Application No. 751869, dated Aug. 12, 2022, 3 pages.
Canadian Office Action, Application No. 3,034,007, dated Aug. 25, 2022, 3 pages.
USPTO, "Non-Final Office Action," issued in connection with U.S. Appl. No. 17/692,876, dated Sep. 19, 2022, 21 pages.
USPTO, "Notice of Allowance," issued in connection with U.S. Appl. No. 17/403,642, dated Sep. 29, 2022, 24 pages.
CNIPA, "First Office Action," issued in connection with Chinese Patent Application No. 202080028183.1, dated Jul. 6, 2022, 21 pages.
Japan Patent Office; "Notice of Reasons for Refusal,"issued in connection with Japanese Patent Application No. 2019-088655, dated Feb. 18, 2020, 5 pages.
European Patent Office, "European Search Report," issued in connection with European Patent Application No. 20792020.8, dated Dec. 23, 2022, 10 pages.
Brazilian Office Action, Application No. BR112020023607-1, dated Dec. 12, 2022, 5 pages.
USPTO, "Non-Final Office Action," issued in connection with U.S. Appl. No. 17/496,614, dated Dec. 21, 2022, 9 pages.
UPSTO, "Non-Final Office Action," issued in connection with U.S. Appl. No. 16/852,303, dated Jan. 9, 2023, 30 pages.
USPTO, "Final Office Action," issued in connection with U.S. Appl. No. 16/741,608, dated Oct. 19, 2022, 12 pages.
USPTO, "Non-Final Office Action," issued in connection with U.S. Appl. No. 17/851,319, dated Nov. 2, 2022, 12 pages.
Notice of Allowance issued in U.S. Appl. No. 16/741,608 dated Feb. 7, 2023, 22 pages.
European Patent Office, "Intention to Grant Notice," issued in connection with patent application No. 20167363.9, dated Dec. 15, 2022, 8 pages.
Notice of Allowance issued in U.S. Appl. No. 17/692,876 dated Feb. 1, 2023, 24 pages.
European Patent Office, "European Search Report," issued in connection with European Patent Application No. 22190948.4, dated Jan. 23, 2023, 10 pages.
Ron Bardell et al. "Microfluidic disposables for cellular and chemical detection: CFD model results and fluidic verification experiments," Proc. SPIE 4265, Biomedical Instrumentation Based on Micro- and Nanotechnology, May 21, 2001; doi: 10.1117/12.427961 Invited Paper: BiOS 2001 The International Symposium on Biomedical Optics, 2001, San Jose, CA, United States, 14 pages.
Notice of Allowance issued in U.S. Appl. No. 17/851,319 dated Feb. 15, 2023, 52 pages.
China National Intellectual Property Administration, "Second Office Action," issued in connection with Chinese Patent Application No. 202080028183.1, dated Jan. 13, 2023, 23 pages.
Brazilian Office Action, Application No. BR112019004727-1, dated Mar. 20, 2023, 6 pages.
USPTO "Final Office Action," issued in connection with U.S. Appl. No. 16/852,303, dated May 1, 2023, 33 pages.
USPTO, "Non-Final Office Action," issued in connection with U.S. Appl. No. 17/164,710, dated Jun. 26, 2023, 13 pages.
National Institute of Industrial Property (INPI) Argentina, "Examination Report," issued in connection with Argentina Patent Application No. 20190101378, dated Apr. 19, 2023, 8 pages.

(56) References Cited

OTHER PUBLICATIONS

China National Intellectual Property Administration, "Decision of Rejection," issue in connection with Chinese Patent Application No. 202080028183.1, dated Jun. 7, 2023, 23 pages.

* cited by examiner

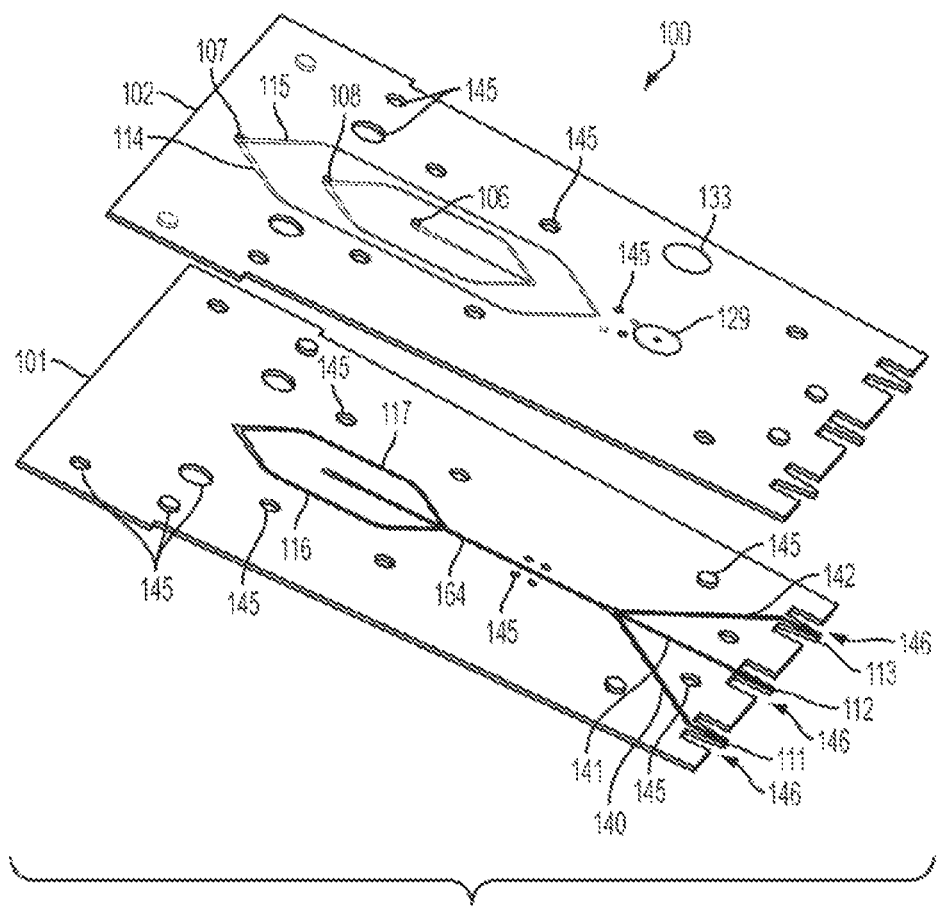
FIG. 1B-(a)

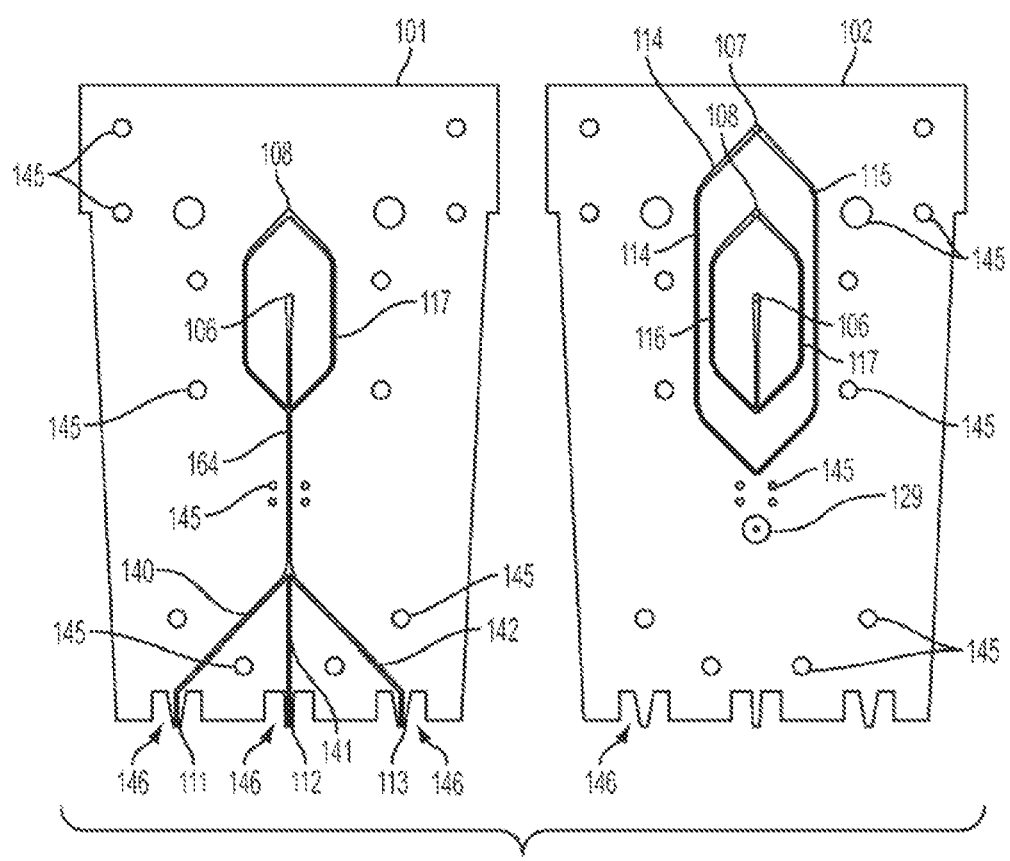
FIG. 1B-(b)

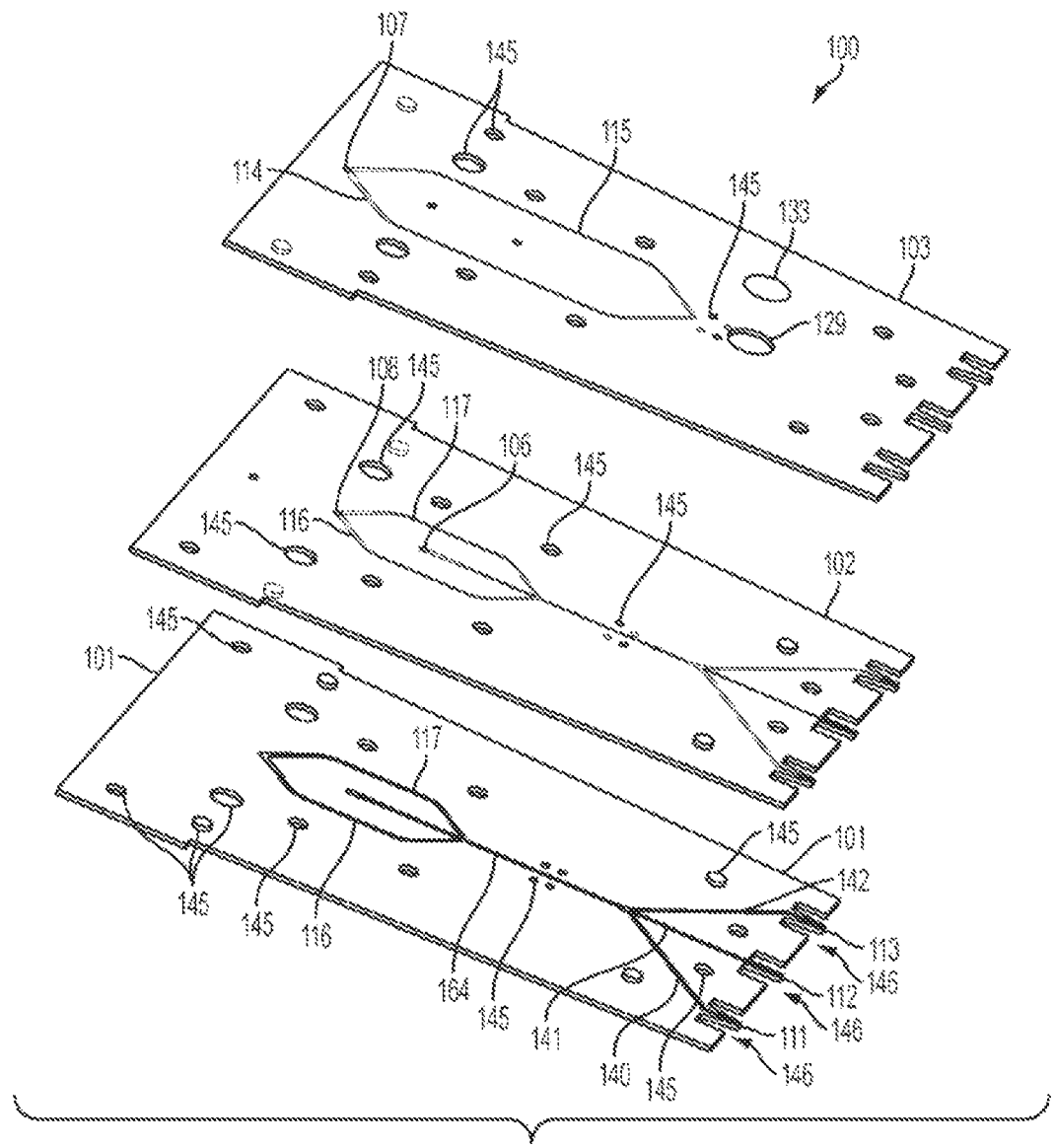
FIG. 1C-(a)

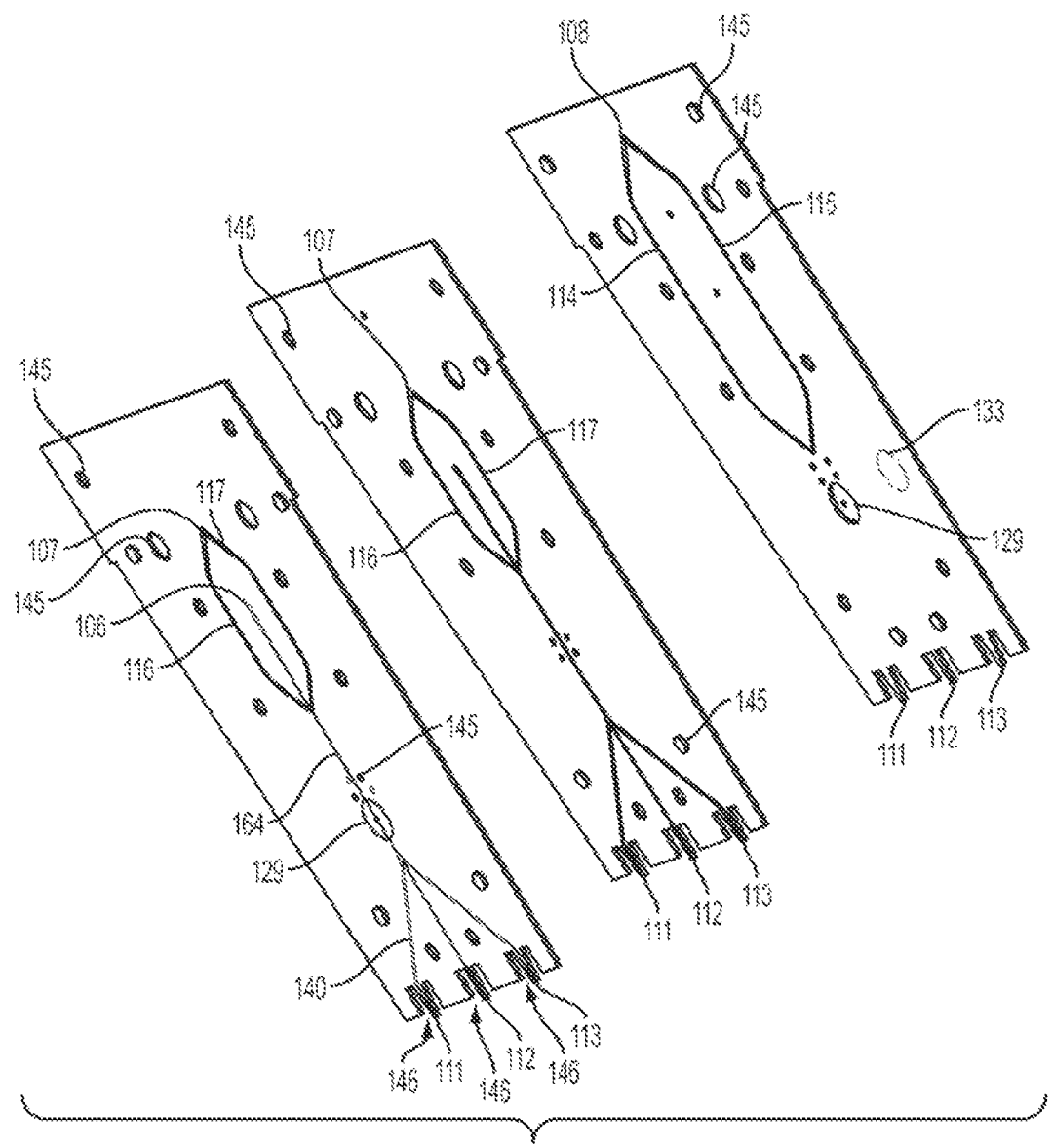
FIG. 1C-(b)

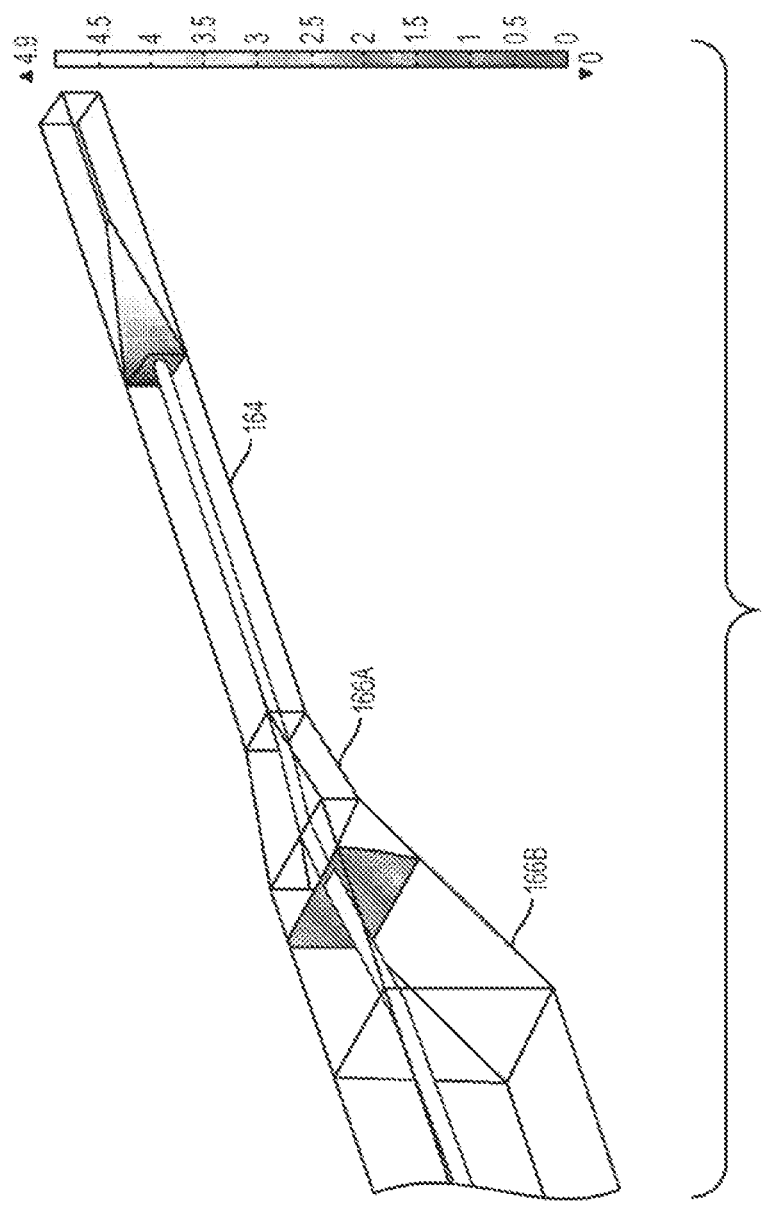

355 nm – closest laser source frequency trippled Nd:YAG

Max excitation: 350 nm
Max emission: 461 nm

MICROFLUIDIC SYSTEM AND METHOD WITH FOCUSED ENERGY APPARATUS

CROSS-REFERENCE TO RELATED APPLICATIONS

The application is a continuation-in-part application of Ser. No. 15/387,034, filed Dec. 21, 2016, which is a continuation application of Ser. No. 15/033,001, filed Aug. 24, 2016, which is a national stage of international application PCT/IB2014/001425, filed Jun. 18, 2014, which claims priority from U.S. Provisional Patent Application No. 61/897,743, filed Oct. 30, 2013, the contents of which are herein incorporated by reference in their entirety.

FIELD OF THE INVENTION

The present invention relates to a microfluidic system with an interrogation apparatus which detects and interrogates objects in a sample fluid mixture of a microfluidic chip, and a focused energy apparatus which performs an action which affects the objects. In one embodiment, the interrogation apparatus interrogates the objects to determine their identity, and the focused energy apparatus is an apparatus acts on target objects. In one embodiment, the focused energy apparatus is used to damage, kill, alter, disable, or destroy the targeted objects.

BACKGROUND OF THE INVENTION

In the separation of various particles or cellular materials—for example, the separation of sperm into viable and motile sperm from non-viable or non-motile sperm, or separation by gender—the process is often a time-consuming task, with severe volume restrictions. Thus, current separation techniques cannot, for example, produce the desired yield, or process volumes of cellular materials in a timely fashion.

Photo-damaging laser systems have utilized lasers to photodamage or kill undesired cellular objects. However, the prior art has required flow cytometers using nozzles, to interrogate and arrange the individual objects in droplet flow, and to attempt to separate and photodamage the objects as they fall into various containers—which has been difficult to achieve.

Thus, there is needed, a method and apparatus which identifies and discriminates between target objects, is continuous, has high throughput, is time and cost effective, and which causes negligible or minimal damage to the various target objects. In addition, such an apparatus and method should have further applicability to other biological and medical areas, not just in sperm discrimination, but in the discrimination of blood and other cellular materials, including viral, cell organelle, globular structures, colloidal suspensions, and other biological materials.

SUMMARY OF THE INVENTION

The present invention relates to a microfluidic system with an interrogation apparatus which detects and interrogates objects in a sample fluid mixture of a microfluidic chip, and a focused energy apparatus which performs an action which affects the objects. In one embodiment, the interrogation apparatus interrogates the objects to determine their identity, and the focused energy apparatus is an apparatus acts on target objects. In one embodiment, the focused energy apparatus is used to damage, kill, alter, disable, or destroy the targeted objects.

In one embodiment, an apparatus which identifies objects includes: a microfluidic chip in which are disposed a plurality of channels, including: a main fluid channel into which a sample fluid mixture of objects to be identified is introduced; a plurality of sheath fluid channels into which sheath fluids are introduced, the sheath fluids which orient the objects in the main fluid channel in a predetermined direction while still maintaining laminar flow in the main fluid channel; an interrogation apparatus which detects and interrogates the oriented objects in the main fluid channel; and a focused energy apparatus which performs an action on the objects.

In one embodiment, the interrogation apparatus detects and interrogates the objects to determine information about the objects.

In one embodiment, the information about the objects determines whether the objects are targeted by the focused energy apparatus.

In one embodiment, the action of the focused energy apparatus acts on the targeted objects or a region surrounding the targeted objects.

In one embodiment, the action on the targeted objects is to damage, disable, alter, kill or destroy the targeted objects.

In one embodiment, the apparatus further includes at least one output channel leading from the main fluid channel, the at least one output channel which removes the objects from the microfluidic chip.

In one embodiment, the at least one output channel removes both targeted and non-targeted objects from the microfluidic chip.

In one embodiment, the apparatus further includes a plurality of side output channels leading from the main fluid channel, the plurality of side output channels disposed on either side of the at least one output channel, the plurality of side output channels which remove the sheath fluids from the microfluidic chip.

In one embodiment, the plurality of sheath fluid channels includes: a first plurality of sheath fluid channels which intersect the main fluid channel at a first intersection, such that the sheath fluids compress the sample fluid mixture on at least two sides, such that the sample fluid mixture becomes a relatively smaller, narrower stream, bounded by the sheath fluids, while maintaining laminar flow in the main fluid channel.

In one embodiment, the plurality of sheath fluid channels further includes: a second plurality of sheath fluid channels which intersect the main fluid channel at a second intersection downstream from the first intersection, such that the sheath fluids from the second plurality of sheath fluid channels compress the sample fluid mixture in one of the at least two sides, or in two sides opposite from the at least two sides, such that the sample fluid mixture is further compressed while still maintaining laminar flow in the main fluid channel.

In one embodiment, when the second set of sheath fluid channels compresses the sample fluid mixture from the at least two sides, the plurality of sheath fluids further comprise: a third sheath fluid channel disposed vertical to the main fluid channel at a third intersection, and disposed downstream from the second intersection, the sheath fluid from the third sheath fluid channel which further compresses the sample fluid while still maintaining laminar flow in the main fluid channel.

In one embodiment, the plurality of sheath fluid channels hydrodynamically focuses the objects such that the objects are oriented in a predetermined direction and disposed in a restricted core volume as the objects flow through the main fluid channel.

In one embodiment, the apparatus further includes an action chamber in which the interrogation apparatus interrogates the hydrodynamically focused objects in the sample fluid mixture, the action chamber disposed in the microfluidic chip downstream from at least one of the second intersection or the third intersection.

In one embodiment, the interrogation apparatus includes: a light source which emits a light beam into the action chamber, to illuminate and excite the objects in the sample fluid mixture.

In one embodiment, the light beam excites fluorescence in the objects such that the targeted objects are distinguished from the non-targeted objects.

In one embodiment, the light source is a laser.

In one embodiment, the apparatus further includes an optical signal detector which detects the light beam and converts it into an electronic signal; and a controller, which analyzes the electronic signal to determine whether the objects are to be targeted or non-targeted.

In one embodiment, the focused energy apparatus is a laser.

In one embodiment, the microfluidic chip contains one or more structural layers or planes.

In one embodiment, the main fluid channel is disposed in a different structural layer or plane from the plurality of sheath channels.

In one embodiment, the at least one of the sample input channel and the plurality of sheath channels are disposed in-between the structural layers or the planes of the microfluidic chip.

In one embodiment, the first plurality of sheath channels is disposed in a different structural layer or plane from the second plurality of sheath channels.

In one embodiment, the action chamber includes a first opening cut through at least one of the structural layers or the planes in the microfluidic chip, the first opening which is configured to receive a first transparent covering.

In one embodiment, the action chamber includes a second opening cut through the at least one of the structural layers or the planes on an opposite side of the microfluidic chip from the first opening, the second opening which is configured to receive a second transparent covering.

In one embodiment, the microfluidic chip contains at least one functional layer which includes the plurality of sheath fluid channels and the main fluid channel, and a top layer which contains holes to access the at least one functional layer.

In one embodiment, a size of one of the second plurality of sheath fluid channels is different from another of the second plurality of sheath channels.

In one embodiment, the size of the second plurality of sheath channels is different from a size of the first plurality of sheath channels.

In one embodiment, the apparatus further includes a first output disposed at an end of the at least one output channel.

In one embodiment, the apparatus further includes a plurality of outputs disposed at an end of each of the plurality of side output channels.

In one embodiment, the apparatus further includes at least one notch disposed in the microfluidic chip, the at least one notch provided between outputs.

In one embodiment, a size of the plurality of side output channels increases from a size of the main fluid channel.

In one embodiment, the main fluid channel tapers at an entry point into the first intersection in the microfluidic chip.

In one embodiment, the main fluid channel tapers into the action chamber.

In one embodiment, the second plurality of sheath channels tapers before joining the main fluid channel.

In one embodiment, the second plurality of sheath channels includes at least a first vertical portion which joins the main fluid channel from approximately a right angle above the main fluid channel.

In one embodiment, the second plurality of sheath channels includes a second vertical portion which joins the main fluid channel from approximately a right angle below the main fluid channel.

In one embodiment, the internal ramps are disposed in at least one of the main fluid channel prior to the first intersection.

In one embodiment, the internal ramps are disposed in the main fluid channel prior to the second intersection.

In one embodiment, the internal ramps are disposed in at least one of the second plurality of sheath channels.

In one embodiment, the objects are cells.

In one embodiment, the cells to be acted upon by the focused energy apparatus include at least one of viable or motile sperm from non-viable or non-motile sperm, or sperm discriminated by gender or other sex discrimination variations.

In one embodiment, the cells to be acted upon by the focused energy apparatus include: stem cells discriminated from cells in a population; one or more labeled cells discriminated from un-labeled cells; cells discriminated by desirable or undesirable traits; cells discriminated based on surface markers; cells discriminated based on membrane integrity or viability; cells having genes which are discriminated in nuclear DNA according to a specified characteristic; cells discriminated based on potential or predicted reproductive status; cells discriminated based on an ability to survive freezing; cells discriminated from contaminants or debris; healthy cells discriminated from damaged cells; red blood cells discriminated from white blood cells and platelets in a plasma mixture; or any cells discriminated from any other cellular objects into corresponding fractions.

In one embodiment, the laser is one of a 349 or 355 nm pulsed laser.

In one embodiment, the laser is a pulsed Q-switch laser able to deliver 15 ns or shorter energy pulses to the objects at a rate of over 1,000 pulses per second.

In one embodiment, the laser is a 532 nm laser.

In one embodiment, the pulsed Q-switch laser preferably delivers 10 ns energy pulses to the objects at a rate of over 200,000 pulses per second.

In one embodiment, the focused energy apparatus acts upon the objects a predetermined amount of time after the interrogation of the objects.

In one embodiment, the focused energy apparatus acts upon the objects prior to interrogation of the objects by the light source.

In one embodiment, the focused energy apparatus acts upon the objects when the objects leave the at least one output prior to being collected in a container.

In one embodiment, the apparatus further includes a container which collects both the targeted and the non-targeted objects.

In one embodiment, the apparatus further includes a pumping apparatus which pumps at least one of the sample fluid mixture or the plurality of sheath fluids into the microfluidic chip.

In one embodiment, the pumping apparatus pumps the at least one of the sample fluid mixture or the plurality of sheath fluids into the microfluidic chip using external tubing.

In one embodiment, the apparatus further includes: at least one external reservoir which holds at least one of the sample fluid mixture or the plurality of sheath fluids.

In one embodiment, the apparatus further includes: a microfluidic chip holder on which the microfluidic chip is mounted, the microfluidic chip holder which includes openings through which the external tubing accesses the microfluidic chip from the at least one external reservoir.

In one embodiment, the apparatus further includes: a controller which controls the pumping of the one of the sample fluid mixture or the plurality of sheath fluids into the microfluidic chip.

In one embodiment, the apparatus further includes a plurality of microfluidic chips disposed in parallel, the plurality of microfluidic chips containing a plurality of sample fluid mixtures; wherein a single interrogation apparatus is used for each of the plurality of microfluidic chips.

In one embodiment, a computer system identifies objects, including: at least one memory which contains at least one program which includes the steps of: controlling a flow of a sample fluid mixture containing objects to be identified, through a main fluid channel of a microfluidic chip; controlling an introduction of a plurality of sheath fluid channels into the microfluidic chip, the plurality of sheath fluids which orient the objects in the main fluid channel in a predetermined direction while still maintaining laminar flow in the main fluid channel; and analyzing an interrogation of the oriented objects in the main fluid channel using an interrogation apparatus; and controlling an action on the objects using a focused energy apparatus; and a processor which executes the program.

In one embodiment, a non-transitory computer readable medium containing instructions to identify objects, includes: controlling a flow of a sample fluid mixture containing objects to be identified, through a main fluid channel of a microfluidic chip; controlling an introduction of a plurality of sheath fluid channels into the microfluidic chip, the plurality of sheath fluids which orient the objects in the main fluid channel in a predetermined direction while still maintaining laminar flow in the main fluid channel; analyzing an interrogation of the oriented objects in the main fluid channel using an interrogation apparatus; and controlling an action on the objects using a focused energy apparatus.

In one embodiment, an apparatus which identifies objects includes: a microfluidic chip in which are disposed a plurality of channels, including: a main fluid channel into which a sample fluid mixture of objects to be identified is introduced; and a plurality of sheath flow channels which perform at least a three step hydrodynamic focusing process on the objects, such that the objects are oriented in a predetermined direction as the objects flow through the main fluid channel.

In one embodiment, the plurality of sheath fluid channels includes: a first plurality of sheath fluid channels which intersect the main fluid channel at a first intersection to accomplish a first step of the at least three hydrodynamic focusing steps, such that the sheath fluids compress the sample fluid mixture on at least two sides, such that the sample fluid mixture becomes a relatively smaller, narrower stream, bounded by the sheath fluids, while maintaining laminar flow in the main fluid channel.

In one embodiment, the plurality of sheath fluid channels further includes: a second plurality of sheath fluid channels which intersect the main fluid channel at a second intersection downstream from the first intersection to accomplish a second step of the at least three hydrodynamic focusing steps, such that the sheath fluids from the second plurality of sheath fluid channels further compress the sample fluid mixture in the at least two sides, such that the sample fluid mixture is further compressed while still maintaining laminar flow in the main fluid channel.

In one embodiment, the plurality of sheath fluids further includes: a third sheath fluid channel disposed vertical to the main fluid channel at a third intersection, and disposed downstream from the second intersection to accomplish a third step of said at least three hydrodynamic focusing steps, the sheath fluid from the third sheath fluid channel which compresses the sample fluid while still maintaining laminar flow in the main fluid channel.

In one embodiment, the apparatus further includes: an interrogation apparatus which detects and interrogates the oriented objects in the main fluid channel; and a focused energy apparatus which performs an action on the objects.

In one embodiment, a method of identifying objects flowing in a sample fluid mixture, includes: flowing a sample fluid mixture containing objects to be identified, through a main fluid channel of a microfluidic chip; introducing a plurality of sheath fluid channels into the microfluidic chip, the plurality of sheath fluids which orient the objects in the main fluid channel in a predetermined direction while still maintaining laminar flow in the main fluid channel; interrogating the oriented objects in the main fluid channel using an interrogation apparatus; and using a focused energy apparatus on the objects.

Thus has been outlined, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the objects set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

BRIEF DESCRIPTION OF THE DRAWINGS

The objects, features and advantages of the present invention will be more readily appreciated upon reference to the following disclosure when considered in conjunction with the accompanying drawings, in which:

FIG. 1B (a) shows an exploded perspective view of an illustrative embodiment of a two-layer microfluidic chip, with the functional layers on the top of the bottom layer, and on the underside of the top layer, according to yet another embodiment consistent with the present invention.

FIG. 1B (b) shows a top view of bottom layer, and the underside of the top layer of the embodiment shown in FIG. 1B (a).

FIG. 1C (a) shows an exploded perspective view of an illustrative embodiment of a three layer microfluidic chip with three functional layers, the top and middle layers having the functional portions on the underside of the layers, according to yet another embodiment consistent with the present invention.

FIG. 1C (b) shows the three layer illustrative embodiment of FIG. 1C (a), from the opposite perspective, with the layers flipped over, showing the underside, functional layers of the top and middle layers.

FIG. 4C shows a ramp feature in the sample channel prior to action chamber, according to one embodiment consistent with the present invention.

DESCRIPTION OF THE INVENTION

Figure 1A:
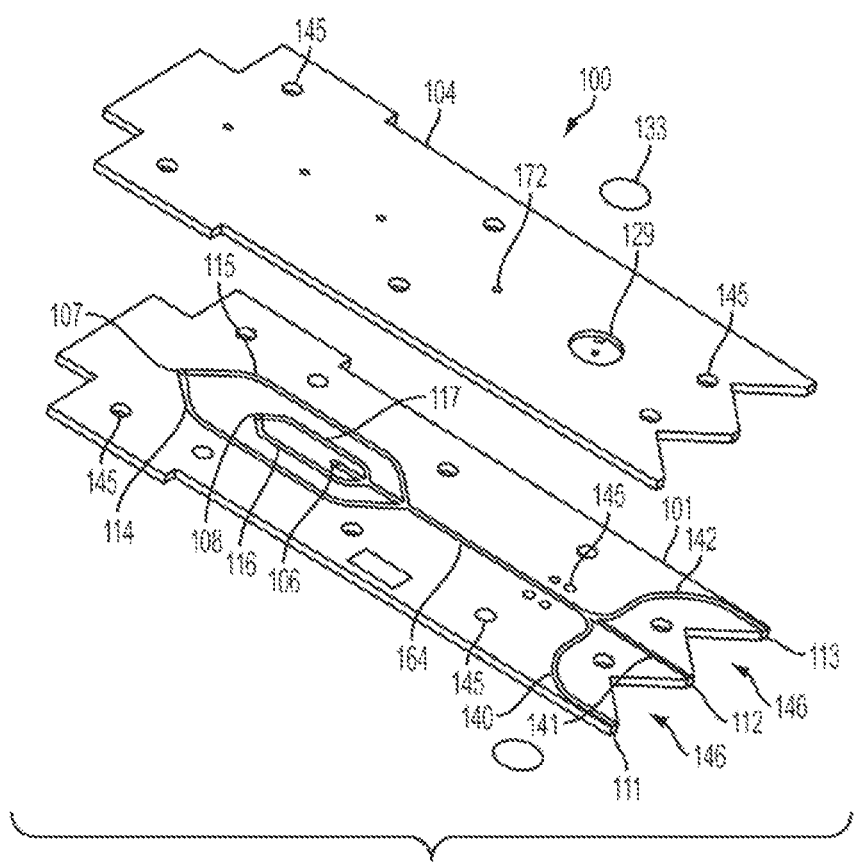
FIG. 1A shows an exploded perspective view of an illustrative embodiment of a single layer microfluidic chip with top "blank" layer, according to one embodiment consistent with the present invention.

Before turning to the Figures, which illustrate the illustrative embodiments in detail, it should be understood that the present disclosure is not limited to the details or methodology set forth in the description or illustrated in the Figures. It should also be understood that the terminology is for the purpose of description only and should not be regarded as limiting. An effort has been made to use the same or like reference numbers throughout the drawings to refer to the same or like parts.

The present invention relates to a microfluidic chip with an interrogation apparatus which detects and interrogates objects in a sample fluid mixture, and a focused energy apparatus which performs an action on the objects or a region around the objects. In one embodiment, the interrogation apparatus interrogates the objects to identify the objects, and to determine whether the objects should be targeted by the focused energy apparatus. In one embodiment, the targeted objects are unwanted targeted objects.

In one embodiment, the focused energy apparatus is a discrimination apparatus which discriminates between targeted and non-targeted objects by damaging, killing, altering, disabling, or destroying the targeted objects. The present invention is conducted in a flowing, continuous fluid stream within the microfluidic network, where objects are subject to hydrodynamic focusing, positioning and orientation, and non-targeted objects are allowed to flow through the microfluidic chip undisturbed, and targeted objects may be acted upon, including photodamaged, killed, altered, disabled, or destroyed, by a focused energy apparatus.

Applications F

The various embodiments of the present invention provide for the selection of objects in a fluid mixture, such as, for example: selecting viable or motile sperm from non-viable or non-motile sperm; selecting sperm by gender, and other sex selection variations; selecting stems cells from cells in a population; selecting one or more labeled cells from un-labeled cells distinguishing desirable/undesirable traits; selecting cells for desirable characteristics; selecting genes in nuclear DNA in cells, according to a specified characteristic; selecting cells based on surface markers; selecting cells based on membrane integrity (viability), potential or predicted reproductive status (fertility), ability to survive freezing, etc.; selecting cells from contaminants or debris; selecting healthy cells from damaged cells (i.e., cancerous cells) (as in bone marrow extractions); red blood cells from white blood cells and platelets in a plasma mixture; and selecting any cells from any other cellular objects, into corresponding fractions; selecting damaged cells, or contaminants or debris, or any other biological materials that are desired to discriminated. The objects may be cells or beads treated or coated with, linker molecules, or embedded with a fluorescent or luminescent label molecule(s). The objects may have a variety of physical or chemical attributes, such as size, shape, materials, texture, etc.

In one embodiment, a heterogeneous population of objects may be measured, with each object being examined for different quantities or regimes in similar quantities (e.g., multiplexed measurements), or the objects may be examined and distinguished based on a label (e.g., fluorescent), image (due to size, shape, different absorption, scattering, fluorescence, luminescence characteristics, fluorescence or luminescence emission profiles, fluorescent or luminescent decay lifetime), and/or particle position etc.

In addition, the subject matter of the present disclosure is also suitable for other medical applications as well. For example, the various laminar flows discussed below may be utilized as part of a kidney dialysis process, in which whole blood is cleansed of waste products and returned to the patient. Further, the various embodiments of the present disclosure may have further applicability to other biological or medical areas, such as for selection of cells, viruses, bacteria, cellular organelles or subparts, globular structures, colloidal suspensions, lipids and lipid globules, gels, immiscible particles, blastomeres, aggregations of cells, microorganisms, and other biological materials. For example, the object selection in accordance with the present disclosure may include cell "washing", in which contaminants (such as bacteria) are removed from cellular suspensions, which may be particularly useful in medical and food industry applications. Further, the present invention has applicability to select non-motile cellular objects from motile cellular objects.

The subject matter of the present disclosure may also be utilized to transfer a species from one solution to another solution where separation by filtering or centrifugation is not practical or desirable. In addition to the applications discussed above, additional applications include selecting colloids of a given size from colloids of other sizes (for research or commercial applications), and washing particles such as cells, egg cells, etc. (effectively replacing the medium in which they are contained and removing contaminants), or washing particles such as nanotubes from a solution of salts and surfactants with a different salt concentration or without surfactants, for example.

The action of selecting species may rely on a number of physical properties of the objects or objects including self-motility, self-diffusivity, free-fall velocity, or action under an external force, such as an actuator, an electromagnetic field or a holographic optical trap. The properties which may be selected include, for example, cell motility, cell viability, object size, object mass, object density, the tendency of objects to attract or repel one another or other objects in the flow, object charge, object surface chemistry, and the tendency of certain other objects (i.e., molecules) to adhere to the object.

While discussion below focuses on the identification and selection of viable or motile sperm from non-viable or non-motile sperm, or selecting sperm by gender and other sex selection variations, or selecting one or more labeled cells from un-labeled cells distinguishing desirable/undesirable traits, etc., the apparatus, methods and systems of the present invention may be extended to other types of particulate, biological or cellular matter, which are capable of being interrogated by fluorescence techniques within a fluid flow, or which are capable of being manipulated between different fluid flows into one or more outputs.

Sample Preparation

In one embodiment, a concentration of objects 160, such as cells (i.e., raw semen), is determined using a cell counting device, such as a Nucleocounter. In one embodiment, the appropriate staining volume is obtained (i.e., using staining a calculator worksheet), and the volume of staining TALP and objects 160 (i.e., neat semen) that need to be added for a predetermined cell concentration (i.e., 200×106/ml sperm concentration), are calculated. For example, a 1 ml amount of stained sample is prepared when the neat semen concentration=1500×106/ml. Thus, 200×106/ml/1500×106/ml=0.133 ml neat semen, which is added to (in order) 0.012 ml Hoechst 33342 (5 mg/ml stock solution), and 0.855 staining TALP (pH 7.4), to equal 1 ml total staining volume at 200×106/ml.

In one embodiment, staining TALP is prepared by filling a container (i.e., beaker) with Milli-Q water to 2/3 of the total desired volume. A stir bar and stir plate are used to mix the solution as chemicals are added. The chemicals, which are added in the order listed (up to the Gentamicin, which is added later), include:

TABLE 1

Chemical components of staining TALP

| CHEMICAL | | g/100 ml | g/500 ml | g/1000 ml |
|---|---|---|---|---|
| HEPES | $C_6H_{12}N_2O_4S$ | 0.952 | 4.760 | 9.520 |
| Magnesium Chloride 6-Hydrate, crystal | $MgCl_2$ *6H2O | 0.008 | 0.040 | 0.080 |
| Sodium Chloride | NaCl | 0.5518 | 2.759 | 5.518 |
| Potassium Chloride | KCl | 0.0224 | 0.116 | 0.224 |
| Sodium Phosphate Dibasic/Anhydrous | $Na_2HPO_4$ | 0.004 | 0.020 | 0.040 |
| Sodium Bicarbonate | $NaHCO_3$ | 0.084 | 0.420 | 0.840 |
| Pyruvic Acid | Na Pyruvate | 0.022 | 0.110 | 0.220 |
| Glucose | $C_6H_{12}O_6$ | 0.090 | 0.450 | 0.900 |
| Lactic Acid, 60% Syrup (ml) | Na Lactate | 0.361 | 1.805 | 3.610 |
| Bovine Serum Albumin | BSA | 0.300 | 1.500 | 3.000 |
| Gentamicin Solution (10 mg/ml) AFTER FILTRATION | | 0.25 ml | 1.25 ml | 2.50 ml |

In one embodiment, after adequate mixing of the chemicals, the pH is adjusted to 7.4 using NaOH. Additional Milli-Q water is used to bring the solution to a final volume in a container (i.e., volumetric flask). A sterile filter (i.e., 0.22 sterile filter) is used to filter/sterilize the volume. An antibiotic (i.e., Gentamicin solution) is added after filtration, and the volume of staining TALP is stored at 5° C., and can be used for 7-10 days.

Thus, after the volume of sample is stained with staining TALP, in one embodiment, the stained samples 120 are placed in containers (i.e., tubes) into a water bath set at 34-35° C., and incubated for a predetermined time (i.e., 45 minutes). In one embodiment, after incubation, the stained samples are removed from the water bath, and an equal volume of 4.0% egg-yolk TALP with red food dye that has been warmed in the water bath set to 34-35° C., is added.

To obtain 4% egg yolk TALP with red food dye, the staining TALP as noted above is prepared, and a desired volume of final solution is determined. The volume of staining TALP and egg yolk required to prepare a 4% egg yolk solution is calculated as follows:

The desired volume: (250 ml)×0.04=10 ml egg yolk needed for 4% solution. 240 ml of staining TALP is added to a graduated container (i.e., cylinder), and 10 ml of egg yolk is added. FD&C #40 food dye is added to the container (i.e., cylinder), to obtain: 0.261 ml/100 ml of solution. With a desired 250 ml total volume, 0.261 ml×250 ml/100=0.653 ml of red food dye. The container (i.e., cylinder) is covered with parafilm and carefully inverted until the volume is thoroughly mixed. The volume container is then allowed to sit overnight and cooled in a cool room. The volume container is then carefully decanted into a sterile container, leaving any sediment at the bottom of the volume container. The volume is then filter/sterilized through a 0.22 .tm bottle top filter, and an appropriate amount of antibiotic solution is added (i.e., 0.250 ml Gentamicin/100 ml of egg yolk TALP).

Thus, after the addition of an equal volume of 4% egg-yolk TALP with red food dye to the stained sample 120, the stained samples 120 are filtered by pouring the samples 120 into a 20-micron filter (i.e., CellTrics filter), that drains into another sterile 5 ml culture container. After a predetermined time of staining (i.e., 45 minutes), equal volume of 4% egg yolk TALP is added. The stained sample 120 (i.e., cells) are run through a filter (i.e., Partec filter, with 50 micron mesh), and the sample is placed into a sample holder or reservoir 233 for introduction into the microfluidic chip 100 (see FIGS. 19-21).

In one embodiment, the final sperm concentration=100× 106/ml, and the final egg-yolk percentage=2%. A new sample aliquot 120 can be prepared and used every hour is desired.

Microfluidic Chip System

The various embodiments of the microfluidic chip, as described below, utilize one or more flow channels, having a plurality of substantially laminar flows, allowing one or more objects to be interrogated for identification by an interrogation apparatus, and to be acted upon by a focused energy apparatus, with the objects exiting the microfluidic chip into one or more outputs. In one embodiment, the objects not targeted by the focused energy apparatus are undisturbed, and the focused energy apparatus photodamages, alters, disables, kills or destroys targeted objects.

The various embodiments of the present invention thereby provide selection of objects on a continuous basis, such as, within a continuous, closed system without the potential damage and contamination of prior art methods, particularly as provided in sperm separation. The continuous process of the present invention also provides significant time savings in selecting and discriminating objects.

Figure 1D:
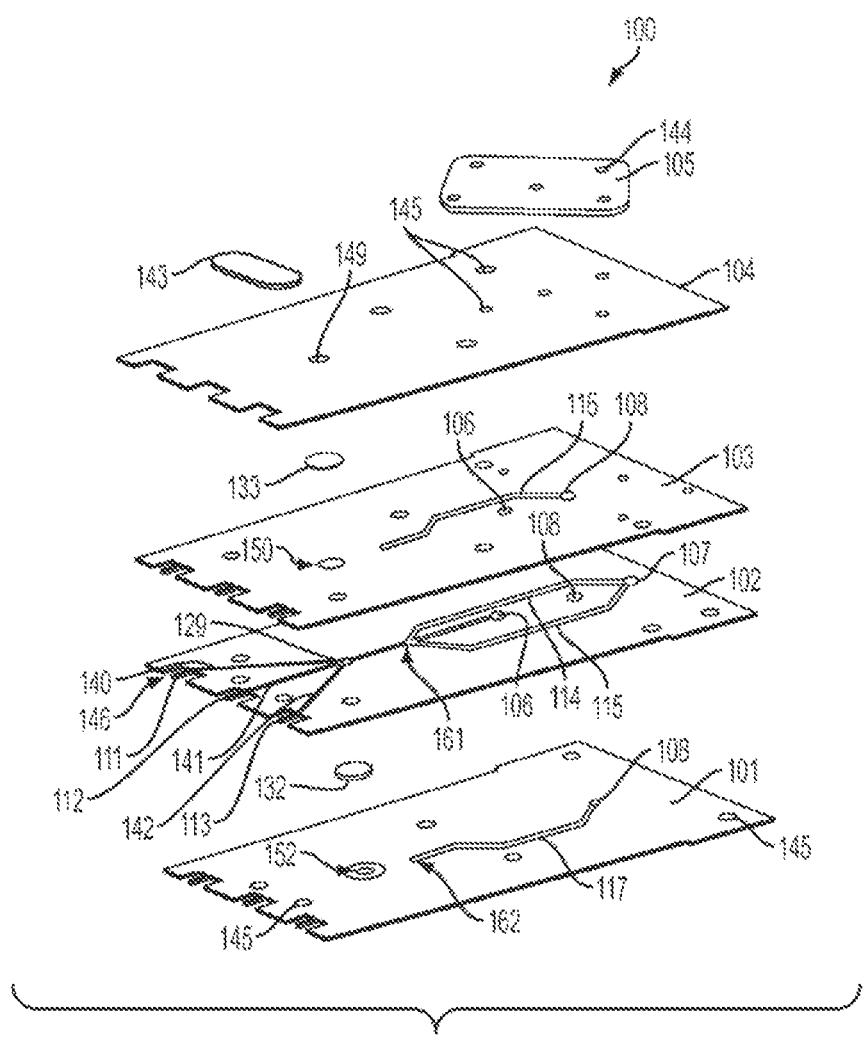
FIG. 1D shows an exploded perspective view of an illustrative embodiment of a four layer microfluidic chip with the top layer being a "blank" layer, according to yet another embodiment consistent with the present invention.
Figure 2:
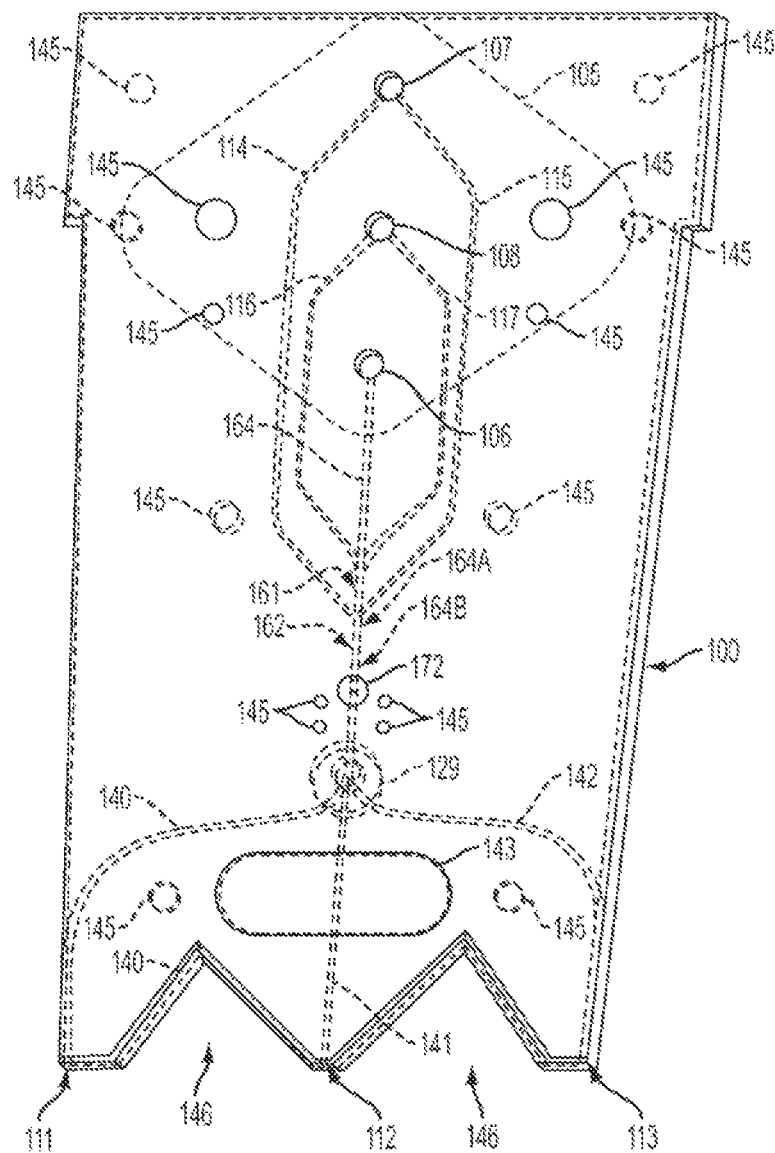
FIG. 2 shows a top view of an illustrative embodiment of a microfluidic chip, according to one embodiment consistent with the present invention.
Figure 20:
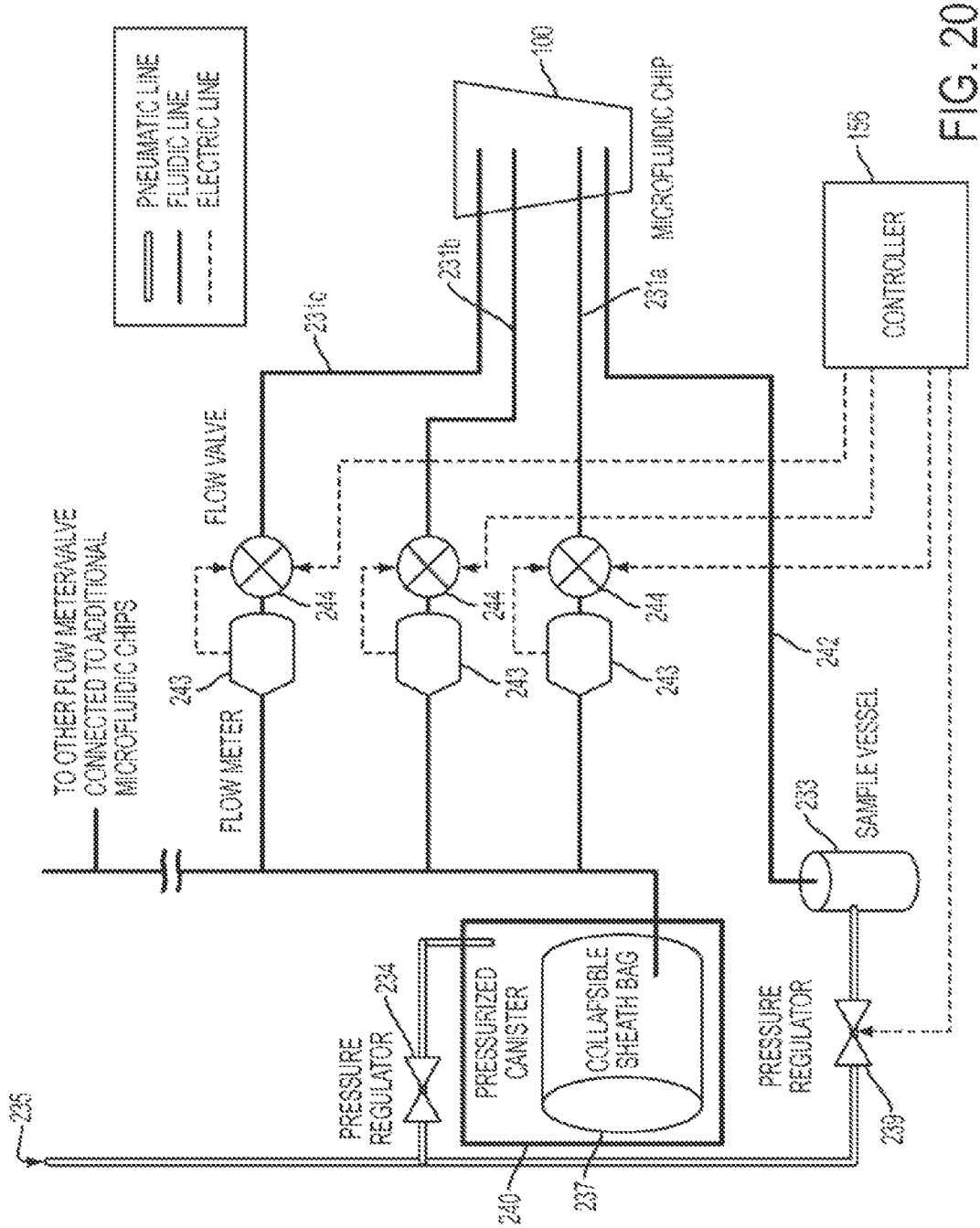
FIG. 20 shows a schematic view of the flow control network of the microfluidic chip system, with an external single sheath or buffer reservoir and sample reservoir, according to one embodiment consistent with the present invention.
Figure 21:
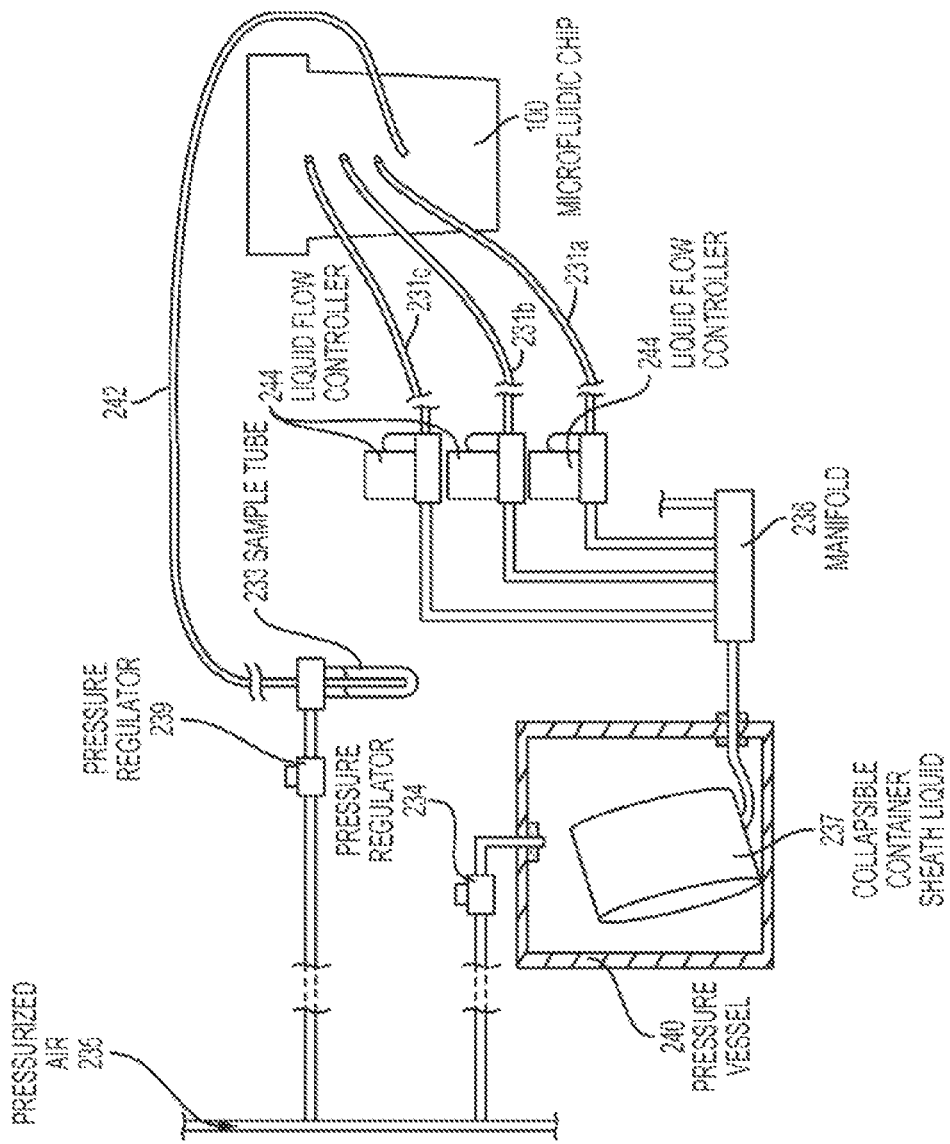
FIG. 21 shows a schematic view of a pressure regulated network of the microfluidic chip system with a single sheath or buffer reservoir, according to one embodiment consistent with the present invention.

While the present subject matter is discussed in detail with respect to a microfluidic chip 100 illustrated in FIGS. 1A-2 and a microfluidic chip holder 200 illustrated in FIGS. 20-21, it should be understood that this discussion applies equally to the various other embodiments discussed herein or any variation thereof.

Microfluidic Chip

FIG. 1A is an illustrative embodiment of a microfluidic chip 100. The microfluidic chip 100 is manufactured of a suitable material such as glass, or a thermoplastic (e.g., low auto-fluorescing polymer etc.), or combination of materials, through an embossing process, soft photolithography, or injection molding process, as well known to one of ordinary skill in the art, and is of suitable size. Each layer may be any suitable thickness, for example, the thickness may be within a range of approximately 300-400 μm, and more preferably the thickness may be approximately 400 μm.

The microfluidic chip 100 includes one or more structural layers in which are disposed micro-channels which serve as sample input channel(s), sheath or buffer fluid channel(s), output channel(s), etc. The micro-channels are of suitable size to accommodate laminar flow streams containing objects, and may be disposed in any of the layers of the chip 100 in the appropriate length, as long as the object of the present invention is realized. In one embodiment, the dimensions of the microfluidic channels range from 50 microns to 500 microns, with 100-300 microns being preferably used to avoid clogging.

The desired flow rate through the microfluidic chip 100 may be controlled by a predetermined introduction flow rate into the chip 100, maintaining the appropriate micro-channel dimensions within the chip 100, by pumping mechanisms which pump external fluids into the chip 100, and by providing narrowing or tapering of the micro-channels at various locations, and/or by providing obstacles, ramps, or dividers within the micro-channels (further discussed below).

More specifically, a plurality of inputs is provided into the microfluidic chip 100, which inputs provide access to the micro-channels/channels. In one embodiment, as shown in FIGS. 1A-2, a sample input 106 is used for introducing a sample of particles or objects (i.e., cells) 160 in a sample fluid mixture 120 into a main fluid channel 164 of the microfluidic chip 100 from at least one reservoir source (see FIG. 19).

The microfluidic chip 100 also includes at least one sheath or buffer input for the introduction of sheath or buffer fluids. In one embodiment, there are two sheath or buffer inputs in the microfluidic chip 100, which include a sheath or buffer input 107 and sheath or buffer input 108, both disposed proximate to the sample input 106, and which both introduce sheath or buffer fluids 163 into the microfluidic chip 100 (see FIGS. 1A-3B).

In one embodiment, there are three sheath or buffer inputs 107, 108, and 172 (see FIGS. 1A and 3B) which introduce sheath or buffer fluids into the channel 164 of the microfluidic chip 100. The location of the sheath or buffer inputs 107, 108, 172 may vary, and they may access channels in the chip 100 which are in the same or different structural layers. In one embodiment, the sheath or buffer fluids 163 are introduced into inputs 107, 108, 172 from a common reservoir (see FIGS. 20-21), or in another embodiment, from separate reservoirs (see FIG. 19).

The sheath or buffer fluids are well known in the art of microfluidics, and in one embodiment, may contain nutrients well known in the art to maintain the viability of the objects 160 (i.e., sperm cells) in the fluid mixture. Commercially available Tris, as sold by Chata Biosystems, is one example, and the sheath or buffer fluid 163 may be formulated to include the following: Water—0.9712 L; Tris—23.88 gg; citric acid monohydrate—11.63 g; D-fructorse—8.55 g. The pH is adjusted to 6.80±0.05 with hydrochloric acid, and osmolarity is adjusted, if necessary, to 270-276 mOsm with fructose high purity. The mixture is filtered using a 0.22 micron filter.

The microfluidic chip 100 may have one or more structural layers in which the micro-channels are disposed. The channels may be disposed in one or more layers or in-between layers. The following embodiments describe a bonding process, but one of ordinary skill in the art would know how to achieve the various features by using an injection molding process. For example, in injection molding, instead of forming two layers, two molds could be made and joined together, such that an injection is made into the cavity in order to obtain the chip of the present invention.

In one embodiment, as shown in FIG. 1A, one structural layer 101 is included in the microfluidic chip, with a top, "blank" plastic layer 104 disposed thereon. The top, "blank" layer 104 bonds with the functional layer 101 to form an enclosed microfluidic network, and may have multiple holes to provide access to the lower layer(s) of the chip 100. For example, the top "blank" layer 104 may have holes corresponding to inputs 106, 107, 108, 172, etc., or provide holes 145 for pins to secure the layers 101, 102, 104 etc., of the chip 100 together. In one embodiment, the top layer 104 of the microfluidic chip 100 includes a plurality of apertures configured to align with the fittings on a microfluidic chip holder 200 (further described below).

In another embodiment, as shown in FIG. 1B (a), two functional, structural plastic layers 101-102 are included in the microfluidic chip 100, with no top, "blank" layer. In this embodiment, the functional side of the top layer 102 is disposed on the underside of the layer 102, so that when the layers are put together, the channels 114, 115, 116, 117 are formed (see FIG. 1B (b)).

In yet another embodiment, as shown in FIG. 1C (a), three functional, structural layers 101, 102, 103 are used in the microfluidic chip 100. As with FIG. 1B (a), layers 102, 103 include functional sides on the undersides of the layers 102, 103, with layers 101 and 102 forming channels 116, 117 when put together. Layer 103 has channels 114, 115 disposed on the underside of the layer 103 (see FIG. 1C (b)).

In yet another embodiment, as shown in FIG. 1D, four structural plastic layers 101-103 and a top, "blank" layer 104, are used in the microfluidic chip 100. In this embodiment, layer 102 includes 114, 115, and layers 101 and 103 each include one of channels 117, 116, respectively.

However, one of ordinary skill in the art would know that more or fewer structural layers with functional sides, and with or without "blank" layers, may be used, and the channels may be disposed in any of the structural layers, or in different structural layers, and in any arrangement, with access to those channels through a top "blank" layer, as long as the object of the present invention is achieved.

In one embodiment, a sample fluid mixture 120 including objects 160, is introduced into sample input 106, and the fluid mixture 120 flows through main channel 164 toward action chamber 129 (see FIGS. 1A-2). The sheath or buffer fluids 163 are introduced into sheath or buffer inputs 107, 108 (see FIGS. 1A-2) in most embodiments, and into sheath or buffer inputs 107, 108, and 172 in another embodiment (see FIG. 1A). The sheath or buffer fluids 163 flow through channels 114, 115 and 116, 117, into the main channel 164, and towards the action chamber 129 before flowing out through at least output channels 140 and 142, in laminar flow.

In one embodiment, the fluid mixture 120 from main channel 164 joins with the sheath or buffer fluids 163 from channels 114, 115 at intersection 161 of the microfluidic chip 100. In one embodiment, buffer fluids 163 from channels 116, 117 join the combined fluid mixture 120 and sheath or buffer fluids 163 from first intersection 161, downstream at second intersection 162 (see FIGS. 1A-2). In one embodiment, sheath or buffer fluids 163 are inputted via input 172 into main fluid channel 164, downstream from the second intersection 162 (see FIGS. 1A and 3B).

In one embodiment, channels 114, 115 are substantially the same dimensions as channels 116, 117, as long as the desired flow rate(s) is achieved to accomplish the object of the present invention, but one of ordinary skill in the art would know that the dimensions may be different as long as they accomplish the desired results (further discussion below).

In one embodiment, channels 114-117 and 140-142 may have substantially the same dimensions, however, one of ordinary skill in the art would know that the size of any or all of the channels in the microfluidic chip 100 may vary in dimension (for example, between 50 and 500 microns), as long as the desired flow rate(s) is achieved to accomplish the object of the present invention.

In one exemplary embodiment, the channels 114, 115 or 116, 117 are disposed in the same structural layer or plane of the microfluidic chip 100, than the layer or plane in which the channel 164 is disposed (see FIG. 1A, for example), or may be disposed in a different structural layer or plane (see FIG. 1B, for example). In another embodiment, the input channel 164 and the sheath channels 114, 115 or 116, 117, may be disposed in-between structural layers or planes of the chip 100. Thus, one of ordinary skill in the art would know that the channels 114-117, 164, and 140-142, etc., can be disposed in any layer or between any two layers. Further, although the channels 114-117, 164, and 140-142, etc. are described in exemplary embodiments as shown in the Figures, one of ordinary skill in the art would know that the particular arrangement or layout of the channels on the chip 100 may be in any desired arrangement as long as they achieve the described features of the present invention.

In one embodiment, the channels 116, 117 are cut through layer 101 (see FIGS. 1A and 2), and join the fluid mixture 120 in channel 164 in the same plane, via holes cut through the layers. In one embodiment, channels 116, 117 substantially parallel input channel 164, and each join intersection 161 at an angle from channel 164 (see FIGS. 2-3). The sheath or buffer fluids from channels 116, 117 compress the fluid mixture 120 flow horizontally from the sides, or laterally, such that the objects 160 in the fluid mixture 120 are flattened and/or oriented in a selected or desired direction, while still maintaining laminar flow in channel 164 (i.e., the first in two steps of hydrodynamic focusing, as described further below).

Further, in one embodiment, channels 114, 115 join the fluid mixture 120 in channel 164 at intersection 162, with each channel 114, 115 at an angle from channel 164 (see FIG. 1A). The sheath or buffer fluids from channels 114, 115 compress the fluid mixture 120 flow with respect to channel 164 (see FIG. 14), such that the objects 160 in the fluid mixture 120 are further flattened and/or oriented in the selected or desired direction, while still maintaining laminar flow in channel 164 (i.e., the second in two steps of hydrodynamic focusing, as described further below).

Further to this embodiment, a third sheath or buffer fluid input 172 is disposed downstream from intersection 162 (see FIG. 3B), which allows a third hydrodynamic focusing step to take place, where the sample fluid mixture 120 is compressed from above the channel 164 by the sheath or buffer fluids 163 introduced therein.

In an alternative embodiment, after the first hydrodynamic focusing step described above, the channels 114, 115 join the fluid mixture 120 in channel 164 at intersection 162 from an angle from above (see FIG. 3A)—and may be above and below (see FIG. 12A)—channel 164, to compress the fluid mixture 120 from a vertical direction to further flatten and/or orient the objects 160 in the channel 164 (i.e., the second hydrodynamic focusing step).

However, one of ordinary skill in the art would appreciate that the depicted configurations, angles, and structural arrangements of the microfluidic chip 100 sheath or buffer inputs, sample input, and sample input channel and sheath or buffer channels, as well as the hydrodynamic focusing steps, may be different as long as they achieve the desired features of the present invention.

In one embodiment, as shown in FIG. 2, channels 114, 115 and 116, 117 are depicted as partially coaxial to one another with a center point defined by the sample input 106. Thus, in one embodiment, channels 114, 115 and 116, 117 are disposed in a substantially parallel arrangement, with the channels 114, 115 and 116, 117 being equidistant to main channel 164. However, one of ordinary skill in the art would recognize that the depicted configuration may be different as long as it achieves the desired features of the present invention.

In one embodiment, holes and pins/posts 145 are disposed at various convenient positions in the layers 101, 102, 103, 104 etc., to fix and align the multiple layers during chip 100 fabrication.

Figure 22A:
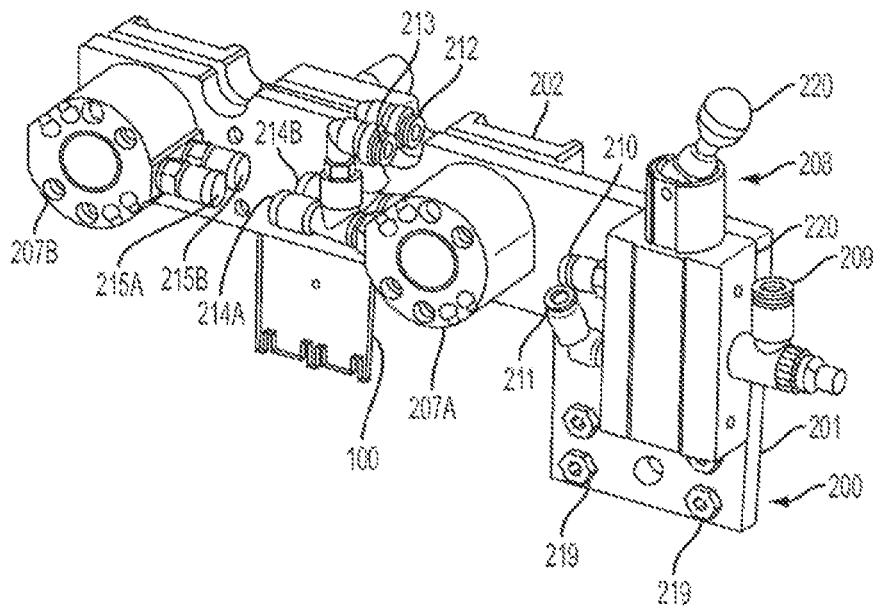
FIGS. 22A and 22B show the front and back, respectively, of a microfluidic chip holder having three ports for fluids to a functional multilayer microfluidic chip, according to one embodiment consistent with the present invention.
Figure 22B:
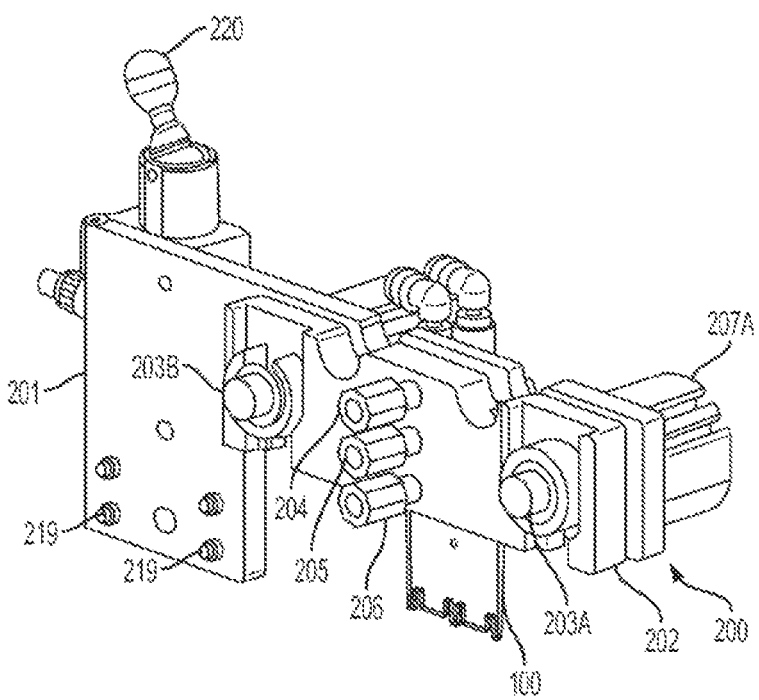
Figure 23A:
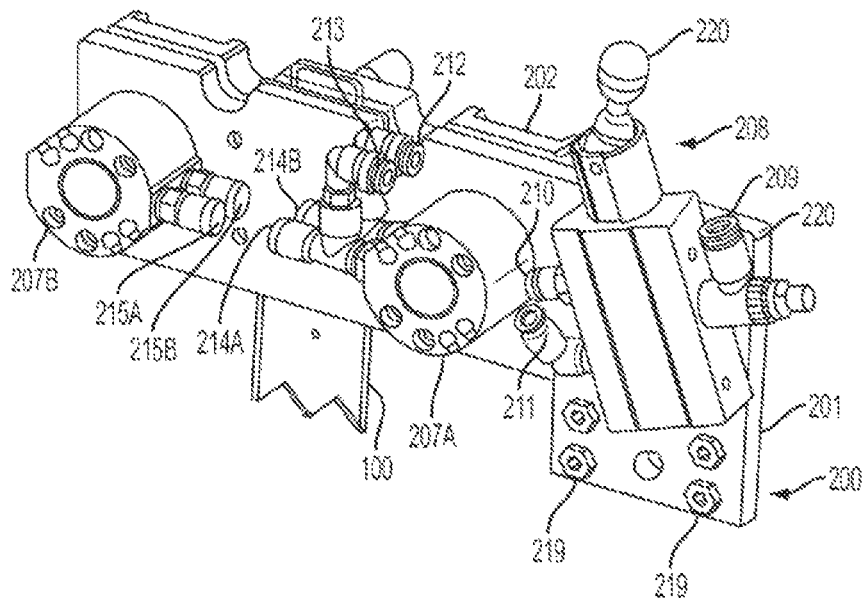
FIGS. 23A and 23B show the front and back, respectively, of a microfluidic chip holder having four ports for fluids to a single layer microfluidic chip, according to one embodiment consistent with the present invention.
Figure 23B:
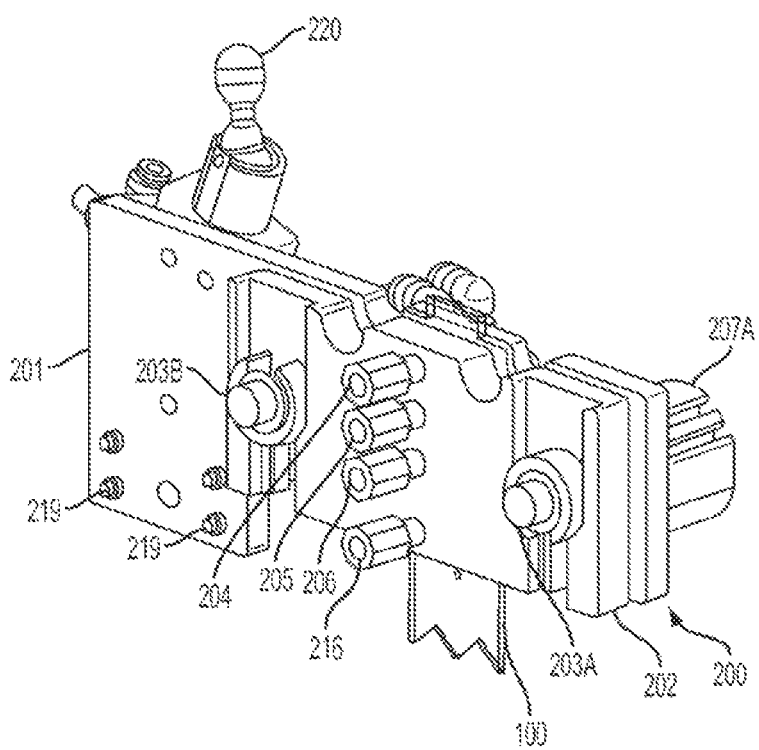

In one embodiment, a gasket 105 of any desired shape, or O-rings, may be provided to maintain a tight seal between the microfluidic chip 100 and the microfluidic chip holder 200 (see FIGS. 1D and 21-22, for example). In the case of a gasket 105, it may be a single sheet or a plurality of objects, in any configuration, or material (i.e., rubber, silicone, etc.) as desired. In one embodiment, as shown in FIG. 1D, a first gasket 105 is disposed at one end of the microfluidic chip 100 and interfaces, or is bonded with layer 104. A plurality of holes 144 are provided in the first gasket 105 and are configured to align with the sample input 106, sheath/buffer input 107, and sheath/buffer input 108.

In one embodiment, a second gasket 143 may be disposed at another end of the microfluidic chip 100 opposite to the first gasket 105 (see FIG. 1D, for example), and interfaces or is bonded with (using epoxy) the top structural layer 104 (see FIGS. 1D and 21-22).

In one embodiment, O-rings are used instead of gaskets, to assist in sealing, as well as stabilizing the microfluidic chip 100 in the chip holder 200.

However, one of ordinary skill in the art would know that one or more gaskets or O-rings may be applied to the outer layers of the chip 100 in order to protect the chip 100 in a chip holder 200, during operation thereof.

In one embodiment, the channels 114-117, and 140-142, of the microfluidic chip 100, may not just vary in dimension, but may have tapered shapes at entry points to other channels in the chip 100 in order to control the flow of fluid through the channels. For example, main channel 164 may taper at the entry point into intersection 161 (see FIG. 4A, taper 166A), or at the entry point into intersection 162 (see FIG. 4B, taper 166A) to control and speed up the flow of sample 120 into the intersection 161, and allow the sheath or buffer fluids 163 from channels 116, 117 or 114, 115, respectively, to compress the sample fluid mixture 120 in a first direction (i.e., horizontally or laterally) on at least two sides, if not all sides (depending on where the fluid channel 164 enters the intersection 161), and in a second direction (i.e., vertically) (see FIGS. 3A-3B, 4A-4B, and tapers 166A).

In another embodiment, ramps may be disposed in channel 164 or channels 114-117 to achieve the effect of controlling and speeding up the sample flow through the channels. The ramps may be in addition or instead of tapers.

Figure 4A:
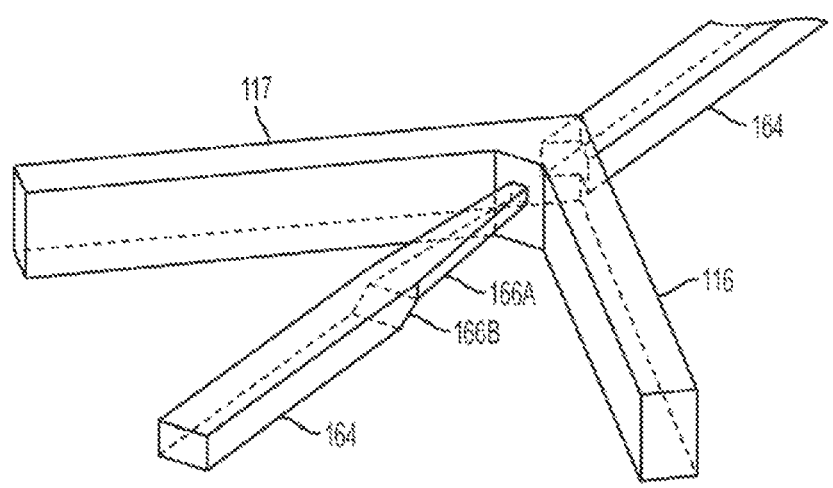
FIG. 4A shows a perspective view of the sample channel, with taper and internal ramp, entering the intersection of the first hydrodynamic focusing region according to one embodiment consistent with the present invention.
Figure 4B:
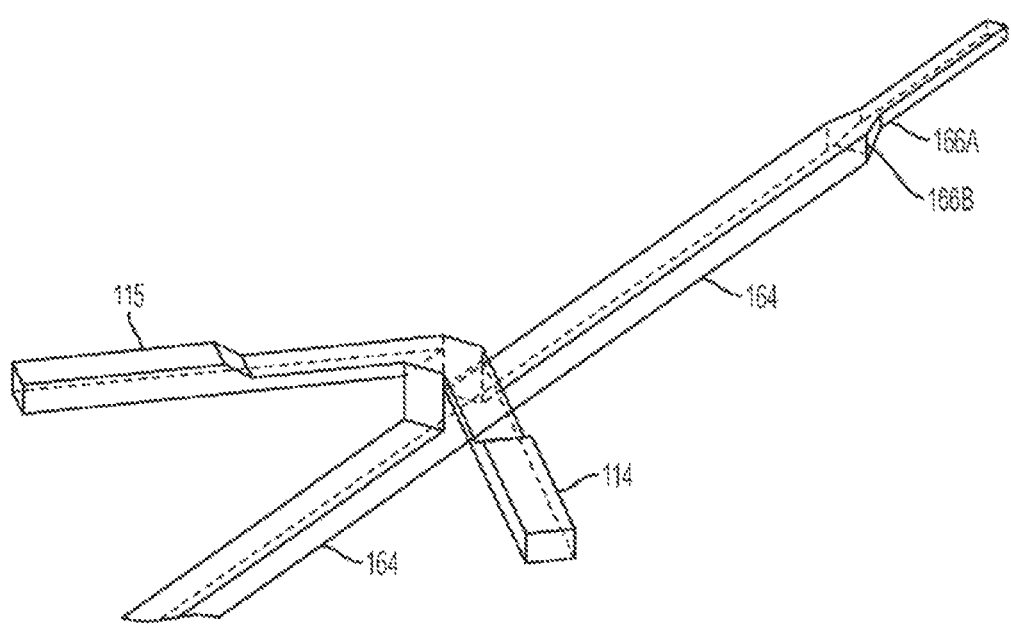
FIG. 4B shows a perspective view of the main channel, with taper and internal ramp, entering the second hydrodynamic focusing region, according to one embodiment consistent with the present invention.

For example, a ramp 166B may be disposed in channel 164 prior to the sample flow approaching intersections 161 and 162, respectively, or prior to entering action chamber 129 (see FIGS. 4A and 4B).

Thus, the sample fluid mixture 120 becomes a relatively smaller, narrower stream, bounded or surrounded by sheath or buffer fluids 163, while maintaining laminar flow in channel 164. However, one of ordinary skill in the art would know that the main channel 164, or the buffer channels 114-117 may be of any physical arrangement, such as a rectangular or circular-shaped channel, with tapers, ramps, or other internal features, as long as the object of the present invention is obtained.

In one embodiment, a plurality of output channels stemming from main channel 164 (see FIG. 2) is provided for removal of fluid flowed through the microfluidic chip 100, including any targeted or non-targeted objects 160 and/or sheath or buffer fluids 163. In one embodiment as shown in FIGS. 1A-2, there are three output channels 140-142 which include a left side output channel 140, a center output channel 141, and a right side output channel 142. The left side output channel 140 ends at a first output 111, the center output channel 141 ends at a second output 112 and the right side output channel 142 ends at a third output 113. However, it is possible to have only one output channel 141 and output 112.

In one embodiment, output channels 140-142 depart from channel 164 within chamber 129 to outputs 111-113. In one embodiment, the cross-section and the length of the output channels 140-142 should be maintained at a predetermined volume ratio (i.e., 2:1:2, or 1:2:1 etc.) to obtain the desired hydraulic resistance of the output channels 140-142.

In one embodiment, the output channels 140-142 increase in dimension from the channel 164, leaving the chamber 129, such that the output ratio for the objects 160, is increased through the relevant channel 141.

In one embodiment, instead of a straight edge, where necessary, a plurality of notches or recesses 146 may be disposed at a bottom edge of the microfluidic chip 100 to separate the outputs (i.e., outputs 111-113) and for the attachment of containers, and external tubing (for recycling the sheath or buffer fluids 163—see FIGS. 19-21) etc. The first output 111, the second output 112 and the third output 113 are reached via output channels 140-142 which originate from action chamber 129 (see FIG. 2).

In one embodiment, a container 188 collects the objects 160 from the second output 112, although other containers may collect the output from first output 111 and third output 113 (see FIGS. 6A-6D). In one embodiment, portions of the first, second, and third outputs 111-113 may be characterized electronically, to detect concentrations of objects 160, pH measuring, cell 160 counts, electrolyte concentration, etc.

In one embodiment, the targeted objects 160 are acted upon by the focused energy apparatus 157, and those objects 160, as well as non-targeted objects 160, may be collected as product 165 from the second output 112.

In one embodiment, the product 165 of targeted and non-targeted objects 160 may continue to be processed for storage, for further separation, or for processing, such as cryopreservation (discussed further below).

In one embodiment, the microfluidic chip 100 is provided in a sterile state, and may be primed with one or more solutions (i.e., sheath or buffer fluids 163), or purged of any fluids or materials by either draining the microfluidic chip 100 or by flowing sheath or buffer fluids 153 or other solutions through the microfluidic chip 100, according to known methods.

Action Chamber

In one embodiment, downstream from intersection 162, the objects 160 in the fluid mixture 120 flow through channel 164 into an action chamber 129, where the objects 160 are interrogated and acted upon. In one embodiment, channel 164 tapers into the chamber 129 (see FIG. 4B), which speeds up the flow of the fluid mixture through the chamber 129. However, one of ordinary skill in the art would know that the channel 164 need not taper and could be of any dimension and size as long as the present invention performs according to the desired requirements.

In one embodiment, an interrogation apparatus 147 is used to interrogate and identify the objects 160 in the fluid mixture in channel 164 passing through the chamber 129. Further, in one embodiment, the focused energy device 157 also acts upon the objects 160 passing through the chamber 129.

In one embodiment, the chamber 129 includes a relatively small diameter opening or window 150 (see FIG. 5) cut through the microfluidic chip 100 and layers 101-102, through which the objects 160 can be visualized as they pass through channel 164.

Figure 5:
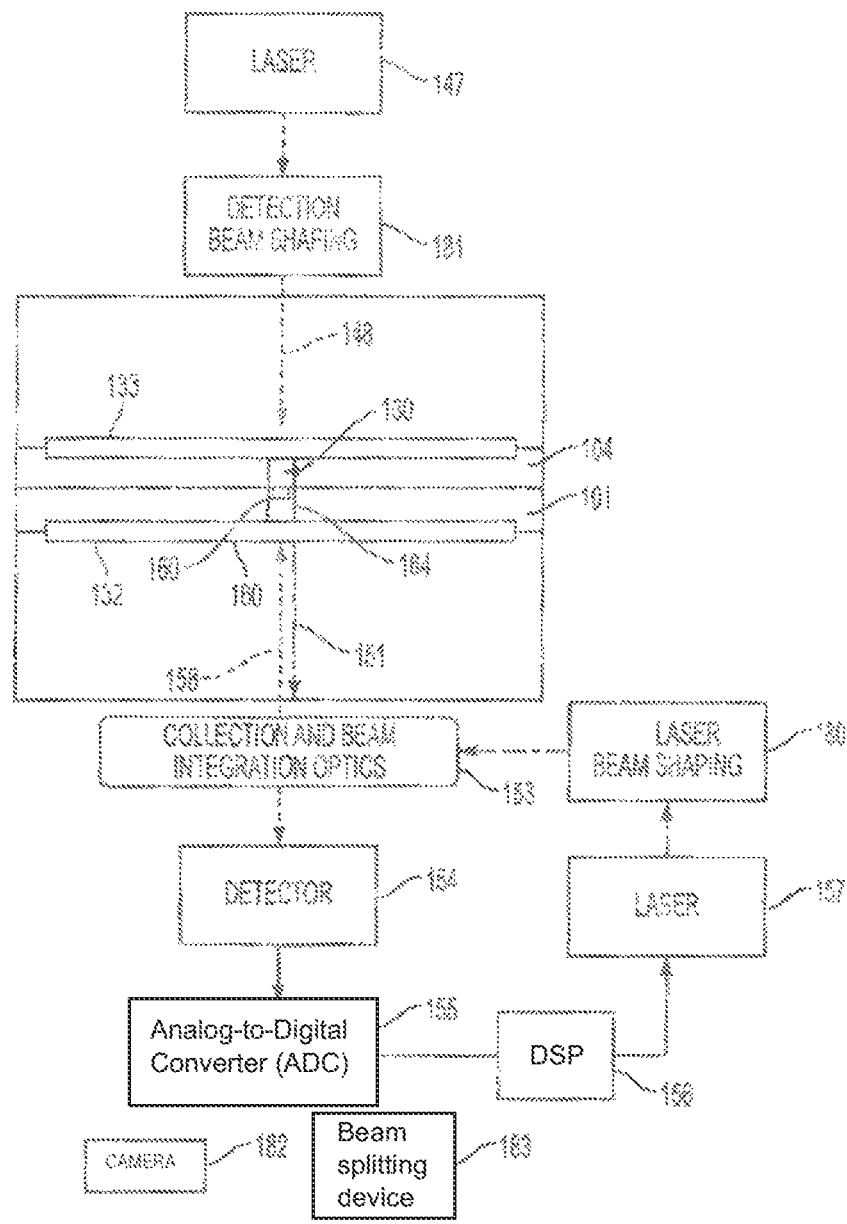
FIG. 5 shows a cross-sectional internal view of an illustrative interrogation by a light source, of objects flowing in a fluid mixture through the main channel of the microfluidic chip system of FIG. 1A, according to one embodiment consistent with the present invention.

Further, a relatively larger diameter and shallow opening is cut into layer 104 as a top window, and into layer 101 as a bottom window. In one embodiment, the top window is configured to receive a first transparent covering 133, and the bottom window 152 is configured to receive a second transparent covering 132. The coverings 133, 132 may be made of any material with the desired transmission requirements, such as plastic, glass, or may even be a lens. In another embodiment, instead of a window with coverings, a contiguous plastic sheet can be used. Note that although the relative diameters of the coverings 132, 133 and opening 150 are shown in FIG. 5, these may vary according to design or manufacturing considerations.

In one embodiment, the above-mentioned first and second coverings 133, 132 are configured to enclose the chamber 129. The windows and coverings 133, 132 (see FIG. 5), allow the objects 160 flowing in the fluid mixture 120 in channel 164 through the chamber 129, to be viewed through opening 150, and acted upon by a suitable light source 147 and a focused energy apparatus 167 (discussed later).

In one embodiment, windows and/or openings are not required due to the structure of the chip layers (i.e., glass), and/or their configuration, or the focused energy device 157 and light source 147 wavelengths and power levels are such that no damage to the chip 100 will occur.

Interrogation Apparatus

The interrogation apparatus of the present invention includes a light source 147 which is configured to emit a high intensity beam 148 with any wavelength that matches excitable objects in the fluid mixture 120 (see FIG. 5). Although a laser 147 is preferred, any suitable other light sources 147 may be used, such as a light emitting diode (LED), or arc lamp, etc. to emit a beam which excites the objects.

In one embodiment, such a high intensity laser beam 148 from a suitable laser 147 of a preselected wavelength—for example, a 349 nm or 355 nm continuous wave (CW), or quasi-CW pulsed laser 147—is required to excite the objects 160 in the fluid mixture (i.e., sperm cells). In another embodiment, a 532 nm green laser 147 is utilized.

In one embodiment, the laser 147 (see FIG. 5) emits a laser beam 148 through the covering 133 at an uppermost portion of the chip 100, through opening 150, to illuminate the objects 160 flowing through channel 164 in chamber 129 of the chip 100, and then through covering 132 in layer 101 of the chip 100, In one embodiment, the light beam 148 can be delivered to the objects 160 by an optical fiber that is embedded in the microfluidic chip 100 at opening 150.

The high intensity beam 148 interacts with the objects 160 (see detailed explanation below), and passes through the first coverings 133, to exit from the covering 132 at the bottom window, such that the emitted light 151, which is induced by the beam 148, is received by an objective lens 153 or other collection optics. The objective lens 153 or other collection optics may be disposed in any suitable position with respect to the microfluidic chip 100—for example, parallel to the main channel with the optical axis perpendicular to the sample fluid flow 120. Because the chamber 129 is sealed by the first and second coverings 133, 132, the high intensity beam 148 does not impinge on the microfluidic chip 100 and damage the layers 101, 104 (see FIG. 1A). Thus, the first and second coverings 133, 132 help prevent damage to the microfluidic chip 100 from the high intensity beam 148 and photonic noise induced from the microfluidic chip 100 material (i.e., plastic).

In one embodiment, the light beam 148 passes through the chip 100 and the emitted light 151 received by the objective lens 153 or other collection optics, is detected by detector 154, and is converted into an electronic signal by an optical sensor 154, such as a photomultiplier tube (PMT) or photodiode, etc. The electronic signal can be digitized or processed by an analog-to-digital converter (ADC) 155 and sent to a digital signal processor (DSP) based controller 156 or computer. The electronic controller 156 can be any electronic processer with adequate processing power, such as a DSP, a Micro Controller Unit (MCU), a Field Programmable Gate Array (FPGA), or even a Central Processing Unit (CPU).

In one embodiment, the DSP based controller 156 monitors the electronic signal, and based upon predetermined criteria, the focused energy apparatus 157 may be employed when a targeted object 160 is detected.

Figure 6A:
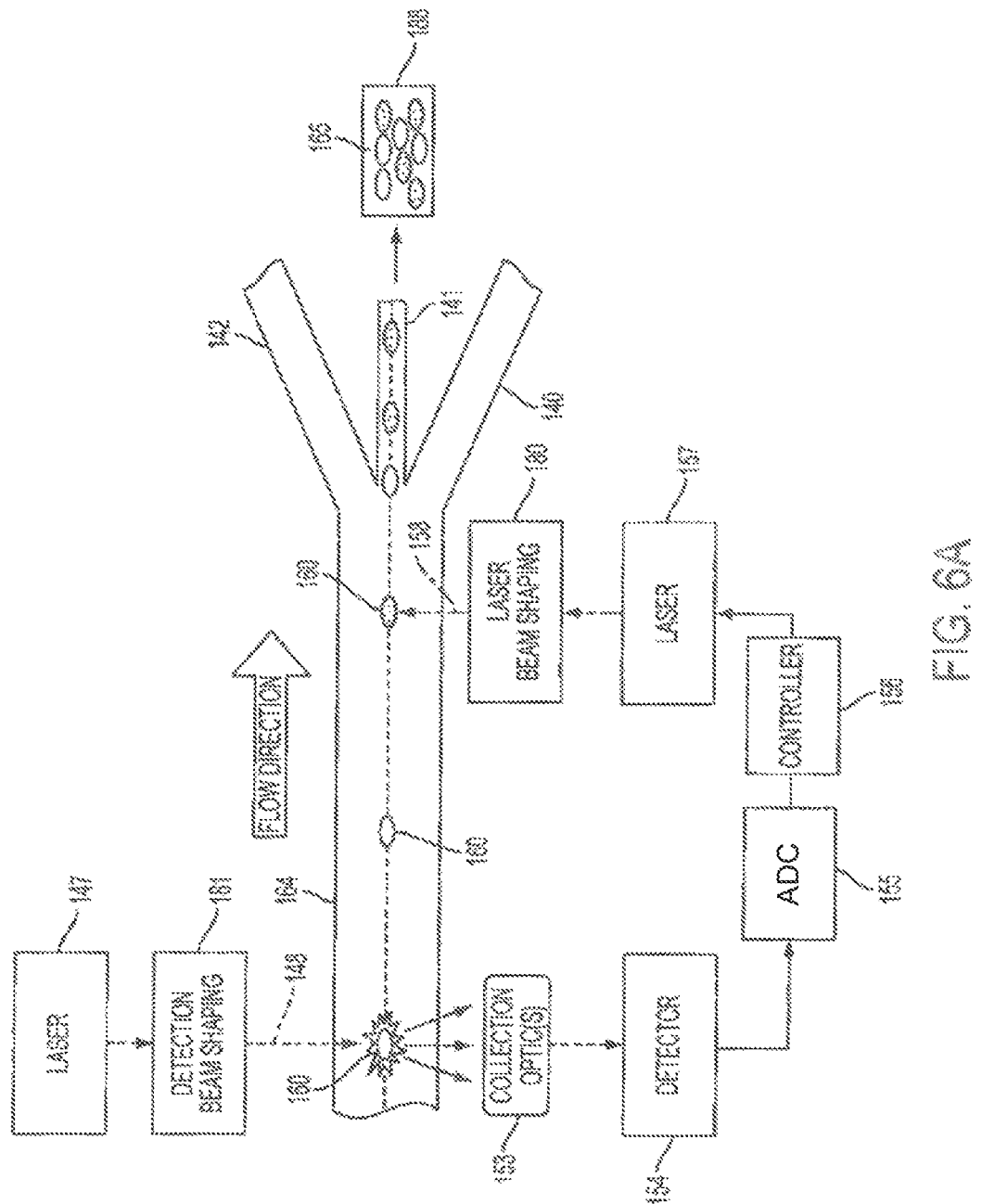
FIG. 6A shows a slanted, schematic side view of the flow of objects in the main channel of a microfluidic chip system, from interrogation to discrimination, with activation of the focused energy device after interrogation, according to one embodiment consistent with the present invention.
Figure 6B:
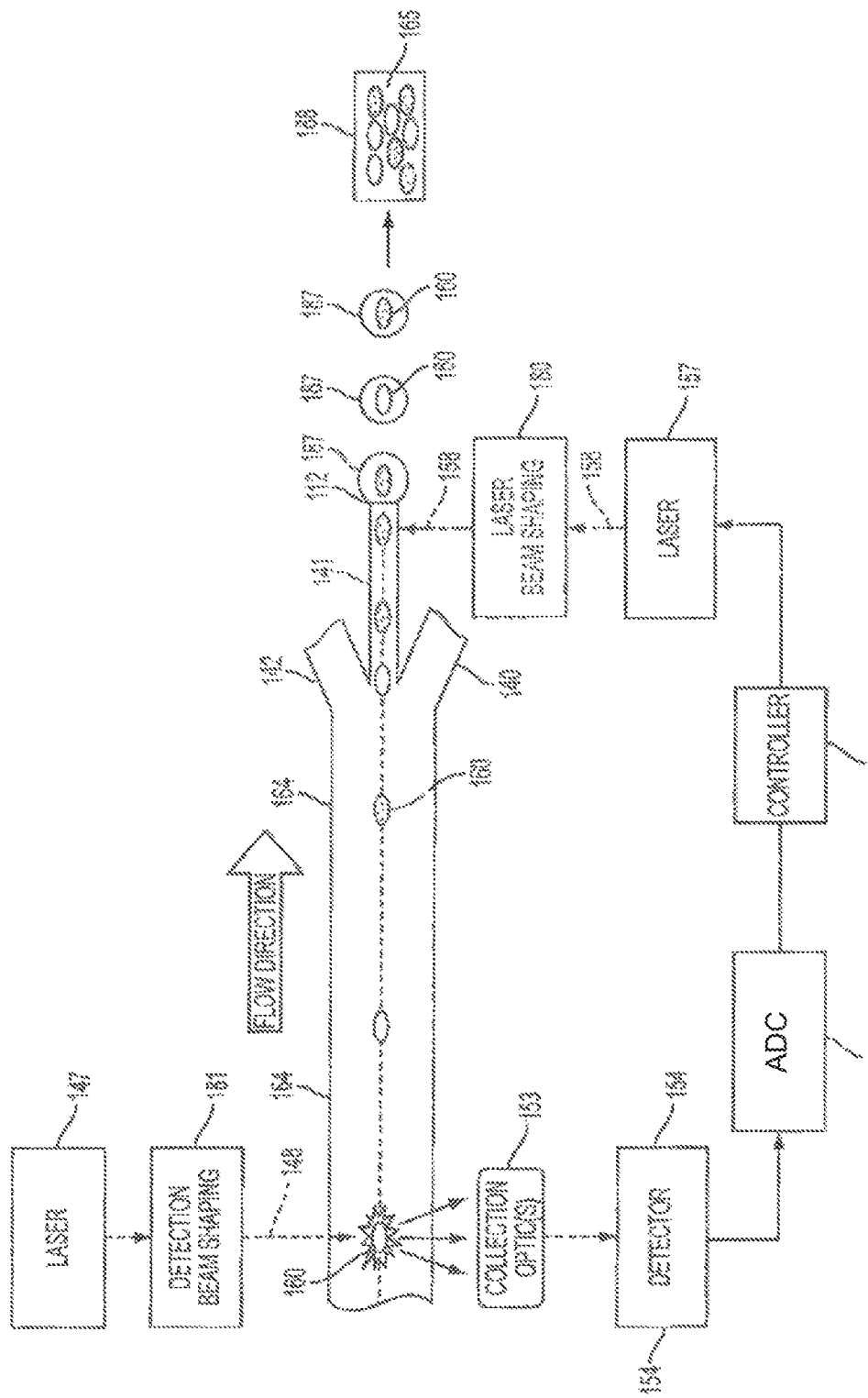
FIG. 6B shows a slanted, schematic side view of the flow of objects in the main channel of a microfluidic chip system, from interrogation to discrimination, with activation of the focused energy device at output channel exit, according to another embodiment consistent with the present invention.
Figure 6C:
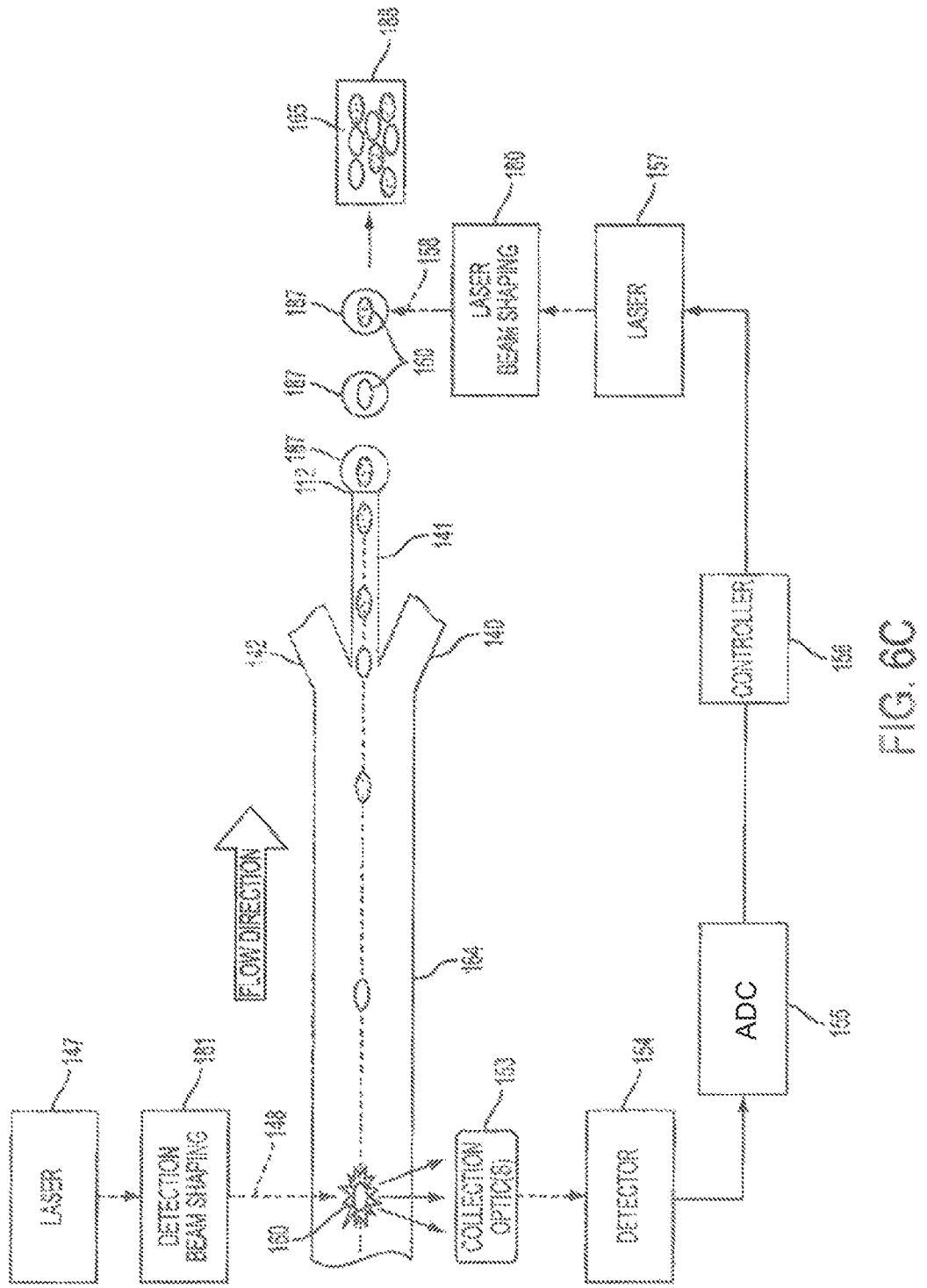
FIG. 6C shows a slanted, schematic side view of the flow of objects in the main channel of a microfluidic chip system, from interrogation to discrimination, with activation of the focused energy device on a disconnected droplet between output channel exit and collection, according to another embodiment consistent with the present invention.

However, in another embodiment, the interrogation apparatus simply interrogates the objects 160 in the sample fluid flow 120 for identity, and it is not connected to the employment of the focused energy apparatus 157 (see FIG. 6C).

Focused Energy Apparatus

In one embodiment, in order to deliver a desired energy level to objects 160, a focused energy apparatus 157 is used to provide focused energy pulses to the objects 160. The focused energy apparatus 157 may be a thermal, electrical, optical, or electromagnetic device 157, which would have a desired wavelength, and would deliver high peak power with a very high repetition rate (or pulse frequency), to the target objects 160.

In one embodiment, the focused energy apparatus 157 is triggered a predetermined time (i.e., milliseconds) after activation by the controller 156 (the timing being set based upon the traveling speed of objects 160 through the channel 164, and is discussed further below), and issues a pulse to the selected or targeted (i.e., unwanted) object 160.

Examples of pulsed lasers 157 include mode-locked, Q-switch, as well as those lasers using both mode-locking and Q-switch techniques. For example, a focused energy device 157 such as an Avia 355-5-100 (made by Coherent, Inc., Santa Clara, CA), or the Explorer XP lasers Q-switch laser from Spectra-Physics Inc., is capable of operating in a pulse-on-demand mode, and can deliver 15 ns energy pulses or less, at a rate of over 1000 pulses per second, to the target objects 160.

In one embodiment, pulse energy levels of 0.5-8.0 µJ are used, and in a preferable embodiment, a Q-switch laser 157 in pulse-on-demand mode is used to deliver an average pulse energy of 1.8 pJ with a range for individual pulses of 1.3 pJ to 2.3 µJ. In one embodiment, the pulse width ranges from 3 nanoseconds to 1 microsecond, and preferably, is in a range of 5-9 nanoseconds. However, one of ordinary skill in the art would know that any high power laser existing now, or later developed, with the appropriate high energy pulses and pulse frequency, would be suitable for the present invention in order to achieve the desired target accuracy and/or effect.

In one embodiment, the need for a tight action region (i.e., chamber 129, or space between the chip 100 and container 188) in order to deliver the pulsed energy from the focused energy apparatus 157 to target objects 160 or a surrounding region thereof, is important to minimize the potential impact of delivering the energy outside of the targeted objects 160 or region, to otherwise unselected, or non-targeted objects 160. For example, a focused energy apparatus 157 such as the Explorer XP 355-1 Q-switch laser, is capable of delivering <4% rms, providing high pulse-to-pulse stability when fired at regular uniform intervals.

However, for flow cytometric analysis and action systems where objects 160 or cells enter the action region (i.e. chamber 129, or space between the chip 100 and container 188—see FIGS. 6A-D) in non-uniform intervals, additional measures are employed to deliver uniform pulse energy 158 to impinge only the targeted objects 160 or cells, or the surrounding region thereof. Such measures include matching laser 157 performance parameters such as pulse length and peak power levels, to enable the system of the present invention to achieve a desired target accuracy (i.e., in one embodiment, photodamage or kill rate of 95% or higher hit rate on target objects 160).

In addition, further tuning the pulse-on-demand operation and performance of the laser 157 to deliver extremely high pulse-to-pulse stability when fired at non-uniform intervals, greatly reduces the spatial variability in the area impacted by the pulse 158. Thus, by reducing pulse-to-pulse variability in the focused energy device 157, the unintended action, damage or destruction to non-target objects 160 or cells, is greatly reduced, achieving, for example, an 85% or higher rate of viability for live, non-target objects 160 or cells.

In one embodiment, the focused energy apparatus 157 is utilized in an action region 129, such as chamber 129, prior to interrogation by the interrogation apparatus 157 (see FIG. 6D), and in another embodiment, the focused energy apparatus 157 is utilized in the action region (i.e., chamber 129) after interrogation by the interrogation apparatus 157 (see FIG. 6A). In yet another embodiment, the focused energy apparatus 157 acts upon the sample fluid with objects 160 after it leaves the chip 100 and enters a container 188—either at the output 112, or in disconnected droplet form 187 before it enters the container 188 (see FIGS. 6B-C).

In the embodiment where the focused energy apparatus 157 acts upon the objects 160 after they are interrogated by the interrogation apparatus 147 in the action region 129 (i.e., chamber 129), upon determination that the objects 160 are to be targeted, the focused energy apparatus 157 emits a focused energy beam 158 to act upon the objects 160 flowing through channel 164 (see FIGS. 5 and 6A-6C, for example).

In the embodiment, the focused energy apparatus 157 acts upon the objects 160 after interrogation in action region 129, and after the objects 160 flow through output channel 141, but before the sample fluid 120 is collected by container 188. In this embodiment, the focused energy apparatus 157 is utilized as above, but is positioned to emit the beam between the chip 100 and the container 188. In one embodiment the sample fluid 120 simply falls from output 112 through the air into the container 188 in droplet form 187, and in another embodiment, there may be a transparent enclosure between the chip 100 and the container 188.

The focused energy apparatus 157 can be set to damage, alter, disable, kill or destroy the targeted or unwanted object 160 in the sample fluid 120 with a pulse, or to activate one of several mechanisms in the object 160 or cell, such that cell damage or death ensues.

However, depending on the desired arrangement (see further below for various embodiments), the targeted or selected objects 160 may be wanted objects 160, in which case the focused energy apparatus 157 is not activated or triggered, or the targeted or selected objects 160 may be unwanted objects 160, where the focused energy apparatus 167 is activated act upon the objects 160, such as to damage, alter, disable, kill or destroy the selected, unwanted objects 160. However, these are not the only embodiments, and the various embodiments are discussed further below.

In one embodiment, when the selected object 160 is damaged, altered, disabled, killed, or destroyed by the focused energy device 157, the object 160 continues to flow through the main channel 164 to the center output channel 141, and to second output 112, and into container 188, along with any non-targeted objects 160. The sheath or buffer fluids 163 proceed in laminar flow through output channels 140, 142, to outputs 111, 112, respectively.

However, in one embodiment, as noted above, the objects 160 in channel 164 may flow out from the chip 100 through output channel 141 and single output 112.

Accordingly, in one embodiment, the present methods and apparatus are capable of producing a discriminated product 165 (see FIGS. 6A-6D) of objects 160 in container 188, including a high viability of non-target or wanted objects 160 or cells, and a high percentage of photodamaged, altered, disabled, destroyed, or dead target objects 160.

Beam Shaping and Optics

Figure 16:
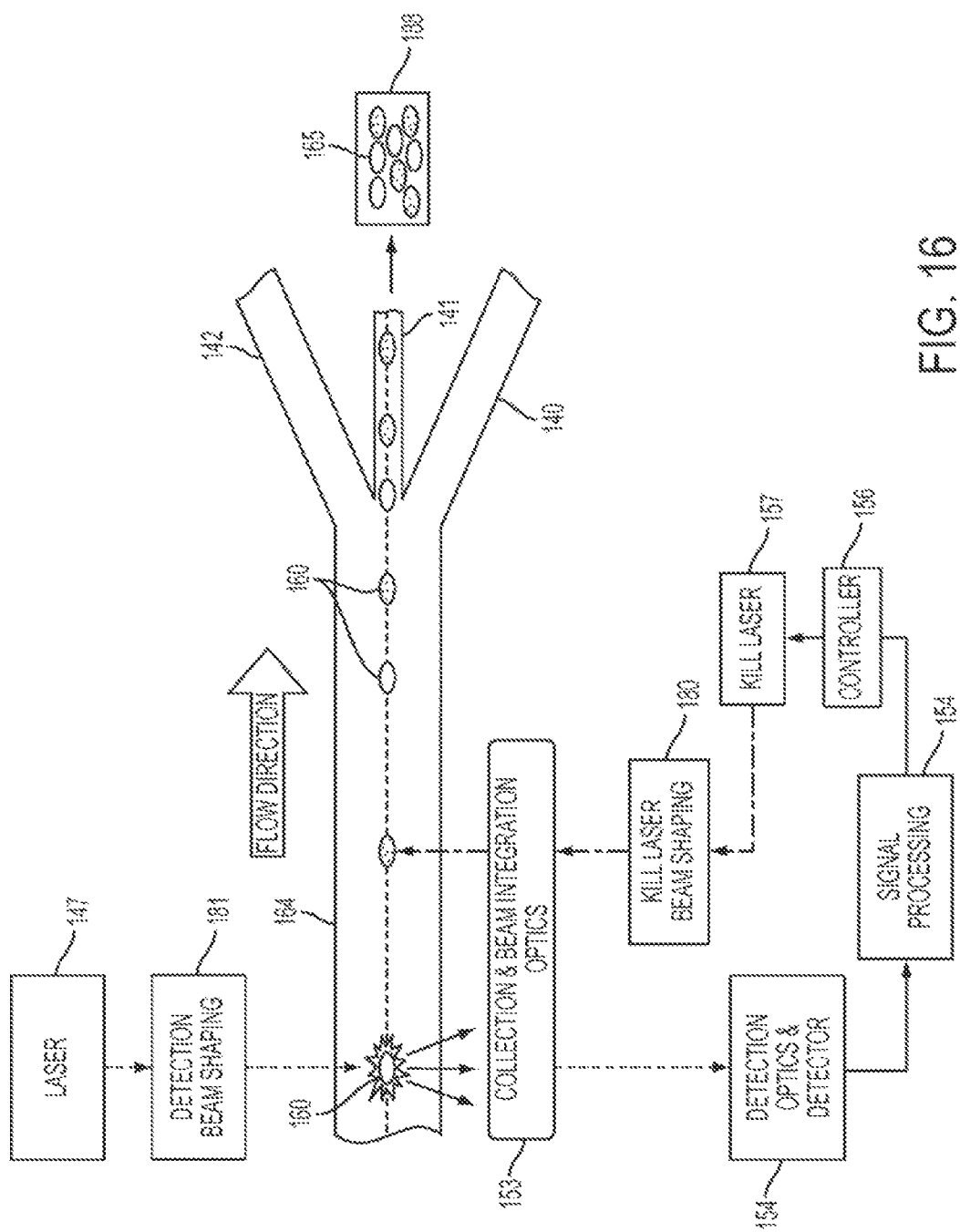
FIG. 16 shows a slanted, side schematic view of the microfluidic chip system with interrogation and discrimination apparatus, and implementation of the beam optics from opposite sides of the sample channel, with the collection optics shared with the focused energy device optics, according to one embodiment consistent with the present invention.
Figure 17:
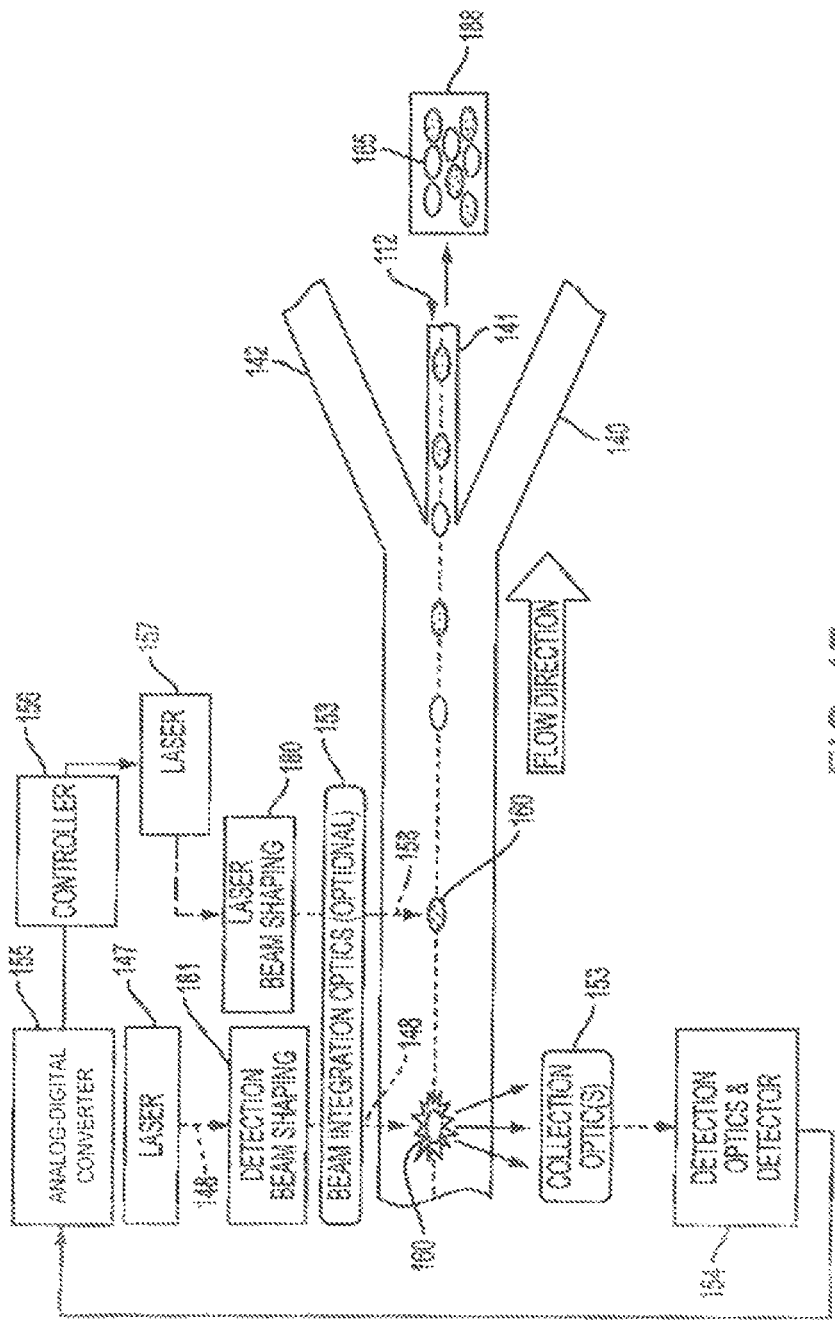
FIG. 17 shows a slanted, side schematic view of the microfluidic chip system with interrogation and discrimination apparatus, and implementation of the beam optics from a same side of the sample channel, with the interrogation and focused energy beams combined through the same, or separate optics, according to one embodiment consistent with the present invention.

In order to achieve satisfactory signal repetition and efficient damaging, altering, disabling, killing, or destruction of objects 160, it is advantageous to use beam shaping optics for both the interrogation beam 148 and the focused energy beam 158 (see FIGS. 16-17). As used herein, the phrase "beam spot" refers to a cross-section of either beam 148, or beam 158.

In one embodiment, the focused energy apparatus 157 is disposed downstream from light source 147, and on the same side as the light source 147 (see FIG. 17), but the focused energy apparatus 157 may also be disposed downstream and on an opposite side of light source 147 (see FIG. 16, for example).

In the embodiment of FIG. 16, a beam shaping optics for the interrogation beam 148 are disposed on one side of chip 100. The interrogation beam 148 from light source 147 passes through the action region (i.e., chamber 129) and is received by objective lens 153.

In one embodiment, the beam 148 is expanded by beam shaping optics 181, which may include a plurality of lenses, which arrangement would be well known to one of ordinary skill in the art. For example, the beam shaping optics 181 may include a pair of prisms and a pair of cylindrical lenses with appropriate focal lengths, or may include other lenses, with or without prisms, which would be available to one of ordinary skill in the art. The beam expansion enables the final spot size at the focal point in the interrogation region 129. In one embodiment, the circular beam 148 spot is expanded using a beam expander 180. The beam expansion also reduces the influence on the downstream optics, limiting damage and extending lifetime. However, in one embodiment, no beam expander is utilized. Alternatively, if the source beam has too large of a diameter, optics could be used to reduce that diameter to a suitable size.

In one embodiment, the beam shaping optics 181 include two perpendicular cylindrical lenses to alter the beam shape 148 into an ellipse perpendicular to the direction of sample fluid 120 flow, and along the direction of sample fluid 120 flow, when focused at the center thereof. This elliptical beam 148 spot serves to excite the objects 160 passing through the channel 164 of the microfluidic chip 100, and provides maximum uniform illumination at a center area of the beam 148 spot, to compensate for minor fluctuations in the flow of objects 160 through the channel 164. Further, in one embodiment, the ellipse of the beam shape having a wider dimension perpendicular to the sample fluid 120 flow, helps to reduce variation in the fluorescence signal coming from the objects 160 (i.e., sperm cells) that are not perfectly centered within the sample fluid 120 flow stream. The narrow dimension keeps the beam 148 at a high enough intensity to adequately excite the fluorescent dye for interrogation of the objects 160 (i.e., sperm cells). While an elliptical beam 148 spot is preferred, in other embodiments of the present invention, a different shaped beam may be utilized. The power of the interrogation beam can be adjusted as well to assist in the interrogation and to limit impact on the interrogated objects In one embodiment, the focused energy beam 158 is also shaped by beam shaping optics 180. The shape of the focused beam 158 spot of the focused energy device 157 influences the desired target accuracy and potential for impacting non-target objects 160 in the channel 164, and can be varying beam shapes, as the application requires. In a flow-based system, the beam width along the direction of flow of the sample fluid 120 should be adjusted to be sufficiently narrow such that only the target object 160 is affected, and sufficient beam intensity concentration is achieved. The length of the beam 158 spot across the fluid channel 164 can be intentionally adjusted to compensate for any slight instability and variability in the focused flow of the sample fluid 120. Desired beam shaping can easily be achieved by one skilled in the art.

In one embodiment, as shown in FIG. 16, beam shaping optics 180 for the focused energy beam 158 is utilized to focus the beam 158 down to a much smaller size to increase a laser flux in the action region 129. In one embodiment, the beam 158 is expanded by beam expander optics 180 (see FIG. 16) which may include a plurality of lenses or prisms with appropriate focal lengths, which would be readily known to one of ordinary skill in the art.

In one embodiment, the beam 158 passes through a pair of anamorphic prisms, for example, to shape the beam 158. The beam 158 is further focused and compressed in the horizontal and vertical directions by an optical object due to a Gaussian beam property. In one embodiment, the optical object may be, for example, detector optics 153 such as a microscope objective or a focusing lens with a short focal length. The beam spot provides a combination of energy concentration for efficient action (i.e., killing, etc.) and sufficient width to compensate for minor fluctuations in a flow of the objects 160 through the microfluidic channel 164. In one embodiment, a pair of cylindrical lenses is used to expand the beam in the vertical dimension, before a spherical focusing lens or objective lens is used to focus the beam to an elliptical beam spot of a minor diameter of 2 .tm and a major diameter of 20 gm.

In alternative embodiments, a different shape and/or dimension(s) may be used for the beam 158. Note that other major and minor diameters are attainable by one skilled in the art and can be applied to the same process.

In another embodiment, the focused energy device 157 is implemented from the opposite side from the interrogation beam 148, as shown in FIG. 17. The configuration shown is advantageous because it is easily implemented and efficiently uses the free space at a photo detector side of the system.

In one embodiment, dichroic mirrors are used to split off specific wavelengths, or to integrate specific wavelengths into the optical path. Further, although a mirror and dichroic mirror/beam splitter may be used, one of ordinary skill in the art would know that more than one mirror and/or dichroic mirror/beam splitter may be utilized in the present system.

In one embodiment, collection optics 153, including a microscope objective, collect the fluorescence emission from the objects 160 in the chip 100, and a dichroic mirror passes the fluorescence emission from the collection optics 153 towards the optical signal detector 154. In one embodiment, the focused energy device 157 emits a beam 158 which passes through beam shaping optics 180 (as described above), and which is directed by a mirror and also reflected by dichroic mirror through collection optics 153 onto the chip 100. Specifically, in one embodiment, the objective lens of the collection optics 153 focuses the focused energy beam 158, which enters the back aperture of the objective lens, into a tight spot on the objects 160 just slightly downstream from the interrogation/excitation point in action region 129. However, one of ordinary skill in the art would know that the focused energy beam 158 may be disposed below the output 112 of the chip 100, or slightly upstream from the interrogation/excitation region 129.

In one embodiment, a distance between the beam spot of the interrogation beam 148 and the beam spot of the focused energy beam 158, is adjustable.

In one embodiment, a dichroic mirror or any beam splitting device, may split a small bit of light off to a camera 182 (see FIG. 5), allowing the user to visually examine alignment.

In one embodiment, the camera 182 provides a visual image of the microfluidic flow environment for general alignment purposes. The camera can be used to determine location and timing for firing of the focused energy device 157.

In another embodiment, the focused energy beam 158 is implemented from the same side as the interrogation beam 148 (see FIG. 17). With this approach, the focusing lens for the focused energy apparatus 157 is not shared with the detection side, so it is more flexible for beam shaping, and it eliminates the need for a microscope objective which is rated for high power at the action (i.e., photodamage, killing) wavelength, which can reduce the system cost.

In this embodiment, the focused energy device 157 emits a beam 158 from the same side as the interrogation apparatus 147, and the beam 158 is shaped by beam shaping optics 180 (described above), to be directed and aligned by a mirror and dichroic mirror, to be focused onto the objects 160 in channel 164 of the chip 100. In one embodiment, beam focusing optics 181 (as described above), are disposed between a dichroic mirror and the chip 100, to focus the beam 158.

As stated above, in the embodiment, the beam 158 is focused into a tight spot on the objects 160 just slightly downstream from the interrogation/excitation point in action region 129. However, one of ordinary skill in the art would know that the focused energy beam 158 may be disposed below the output 112 of the chip 100, or slightly upstream from the interrogation/excitation region 129 (see FIGS. 6A-D).

Further, as stated above, in the embodiment, a distance between the beam spot of the interrogation beam 148 and the beam spot of the focused energy beam 158, is adjustable.

Object Focusing and Orientation

In conventional flow cytometry systems, since objects or cells, especially with asymmetric shapes, tend to orient as they flow close to a solid surface, the function and improvement of object or cell orientation relies on complex nozzle designs, such as orienting baffles or an offset structure inside the nozzle. To avoid the complex design of nozzle-based flow cytometry systems, and their high fabrication cost, the microfluidic chip 100 design of the present invention focuses, positions and orients the objects 160, in order to optimize its analytical capability. Thus, in one embodiment, the objects 160 (i.e., cells) with non-spherical shapes are aligned into a restricted core volume in channel 164 and maintained in a similar and desired orientation when they pass through the interrogation/detection beam 148. As a result, more uniform scattering and detection signals will be obtained, thus, helping to increase the system's 100 sensitivity and stability.

In one embodiment, the orientation of objects 160 can be realized by positioning the sample core stream 120 offset with respect to the center of the central plane of the channel 164 cross-section, using hydrodynamic focusing.

Two-Step Hydrodynamic Focusing

The following describes two-step hydrodynamic focusing that takes place during fluid flow in one embodiment of the microfluidic chip 100 (see FIGS. 1B-1D).

In one embodiment, the first hydrodynamic focusing step of the present invention is accomplished by inputting a fluid sample 120 containing objects 160, including biological samples such as sperm cells 160 etc., through sample input 106, and inputting sheath or buffer fluids 163 through sheath or buffer inputs 107, 108. In one embodiment, the objects 160 are pre-stained with dye according to known methods (e.g., Hoechst dye), in order to allow fluorescence and imaging thereof.

Figure 3A:
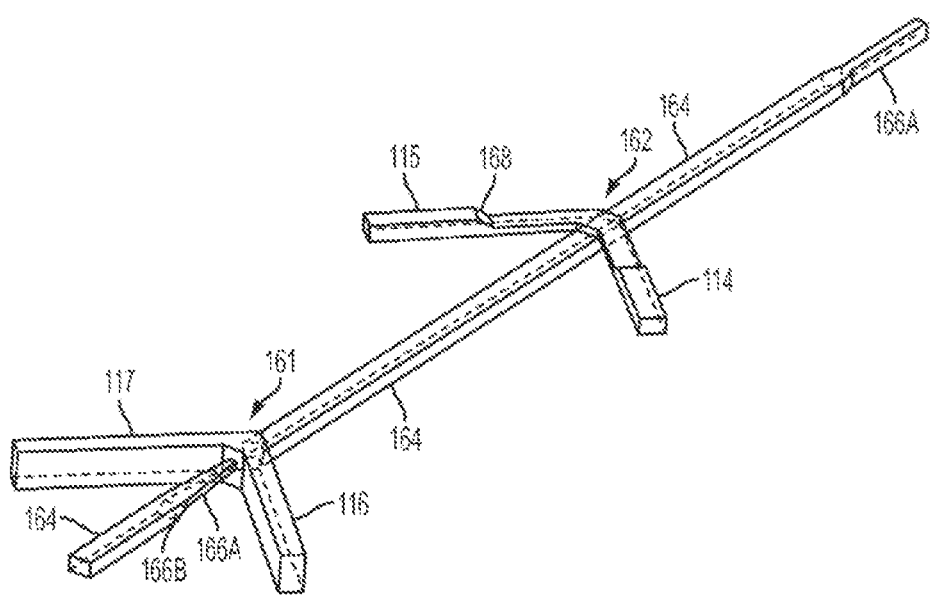
FIG. 3A shows a perspective view of the sample, and sheath or buffer channels in a two (functional) layer microfluidic chip, according to one embodiment consistent with the present invention.

In one embodiment, objects 160 in the sample fluid mixture 120 flow through main channel 164, are surrounded and shaped by the fluid flow, and have random orientation and position (see FIGS. 3A and 6A). At intersection 161, the sample mixture 120 flowing in main channel 164 is surrounded and shaped by the sheath or buffer fluids 163 from channels 116, 117, and compressed in a first direction (i.e., at least horizontally, on at least both sides of the flow, if not all sides depending on where the main channel 164 enters the intersection 161), when the sheath or buffer fluids 163 meet with the sample mixture 120. This compression is termed hydrodynamic focusing (three-dimensional (3-D)), and is used to align the objects 160 in the channel 164 into a restricted core volume that may approximate a single file formation. The hydrodynamic focusing takes advantage of significantly large sheath or buffer flow in channel 164 to accelerate the travelling velocity of the objects 160 through the planar microfluidic channel 164. In one embodiment, the sample core stream 120 may also be offset from the central plane by a ramp 166B or taper 166A structure in the channel 164 which is prior to the junction 161 of the channel 164 and the first-step sheath or buffer channels 116, 117.

As a result, the objects 160 are speeded up and the spacing between the objects 160 in the microfluidic channel 164 also can be stretched. The velocity of the objects 160 is dependent upon the sample 120 flow rate and the ratio of the value to total sheath or buffer 163 flow rate. This function is useful to avoid clogging issues and object 160 clumping with highly concentrated object samples 120.

Figure 8A:
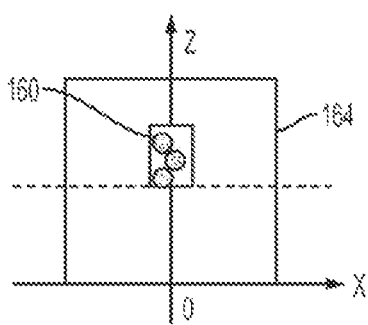
FIG. 8A shows a cross-sectional view of the main channel of a microfluidic chip, after the first-step hydrodynamic focusing, with the sample fluid compressed on the sides of the main channel, and the objects offset from the central portion of the main channel.

However, as shown in FIG. 8A, at this stage, the resulting sample 120 core stream across the main channel 164 still shows overlapped objects 160 or cells along the channel 164 depth direction or vertical axis. In particular, the objects 160 are focused around the center of the channel 164, and may be compressed into a thin strip across the depth of the channel 164. Thus, at intersection 161, as the sample fluid 120 is being compressed by the sheath or buffer fluids 163 from channels 114, 115, toward the center of the channel 164, the objects 160 (i.e., sperm cells) move toward the center of the channel 164 width.

Figure 14:
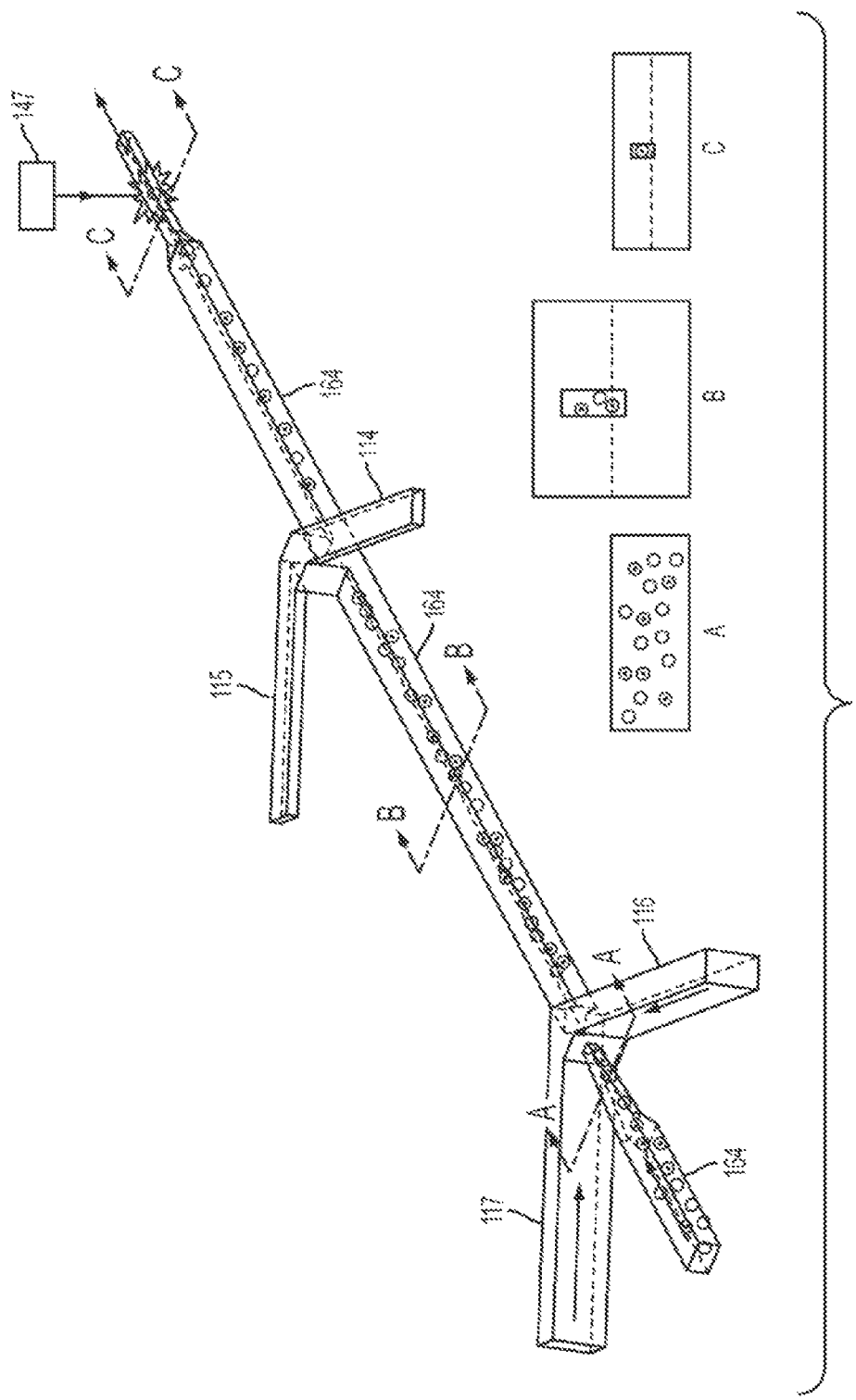
FIG. 14 shows a perspective, internal and oblique view of objects flowing through the microfluidic chip, and an illustrative operation of two-step hydrodynamic focusing, with single sheath or buffer fluids entering from an upper portion of the main channel, according to one embodiment consistent with the present invention.

In one embodiment, the present invention includes a second focusing step, where the sample mixture 120 containing objects 160, is further compressed by sheath or buffer fluids 163 from a second direction (i.e., the vertical direction, from the top and the bottom) entering from channels 114, 115 at intersection 162 (see FIG. 14). The intersection 162 leading into channel 164B is the second focusing region. Note that although the entrances into intersection 162 from channels 114, 115 are shown as rectangular, one of ordinary skill in the art would appreciate that any other suitable configuration (i.e., tapered, circular) may be used.

Figure 15:
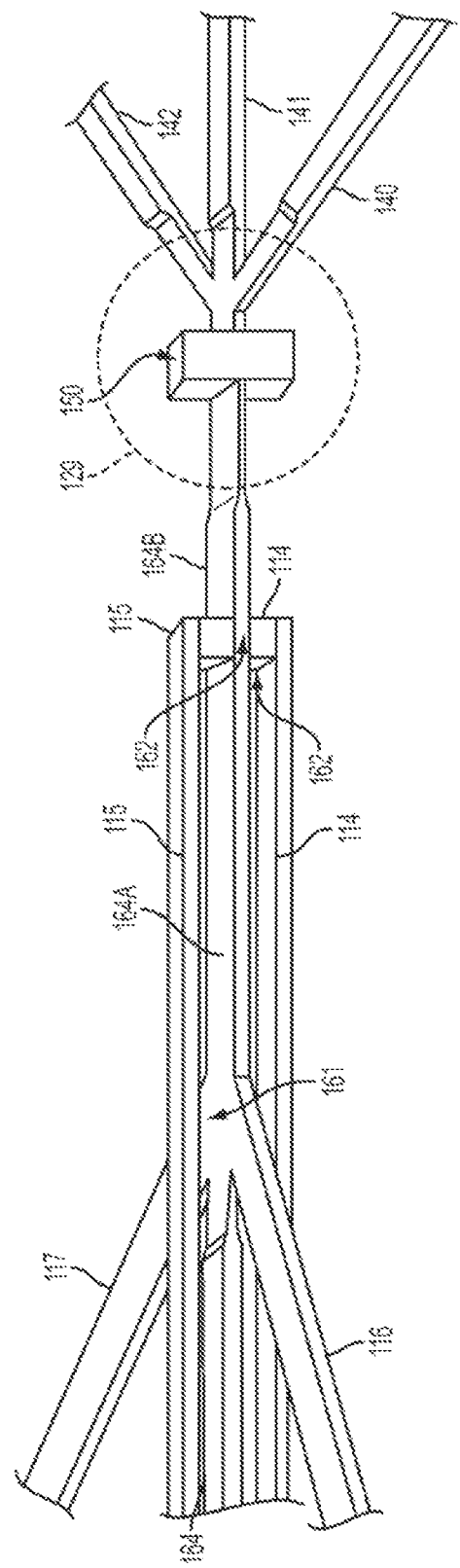
FIG. 15 shows a perspective view of the microfluidic chip, and an illustrative operation of two-step hydrodynamic focusing, with sheath or buffer fluid channels entering vertically from both an upper and a lower portion of the sample channel, according to one embodiment consistent with the present invention.

In one embodiment, the sheath or buffer fluids 163 in the channels 114, 114 enter from the same plane (see FIGS. 3A and 6A), or from different planes into the channel 164 (see FIG. 15, where channels 114, 115 are disposed above and below main channel 164, entering channel 164 vertically), to align the objects 160 in the center of the channel 164B by both width and depth (i.e., horizontally and vertically) as they flow along channel 164B. Then, the resulting flow in the main channel 164 is subsequently compressed and repositioned by the second-step sheath flow via microfluidic channels 114, 115.

Figure 8B:
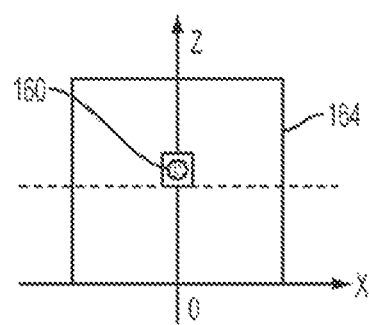
FIG. 8B shows a cross-sectional view of the main channel of a microfluidic chip, after second-step hydrodynamic focusing, with the sample fluid compressed from above and below the main channel, such that the objects are substantially centrally located in the main channel.

Thus, in the second focusing step of the present invention, the sample mixture 120 is again compressed by the vertical sheath or buffer fluids 163 entering at channels 114, 115, and the sample 120 stream is focused at the center of the channel 164 depth, as illustrated in FIG. 8B, and the objects 160 flow along the center of the channel 164 in a restricted core volume that may approximate a single file formation in a particular orientation.

Accordingly, after these two subsequent hydrodynamic focusing steps, a restricted core volume of objects 160 or cells is obtained and the position of the stream also can be adjusted to a desired location along the vertical axis (see FIG. 8B). Thus, the objects 160 introduced into sample input 106, undergo two-step hydrodynamic focusing, which allows the objects 160 to move through the channel 164B in a restricted core volume that may approximate a single file formation, in a more uniform orientation (depending on the type of objects 160), which allows for easier interrogation of the objects 160.

Three-Step Hydrodynamic Focusing

Figure 3B:
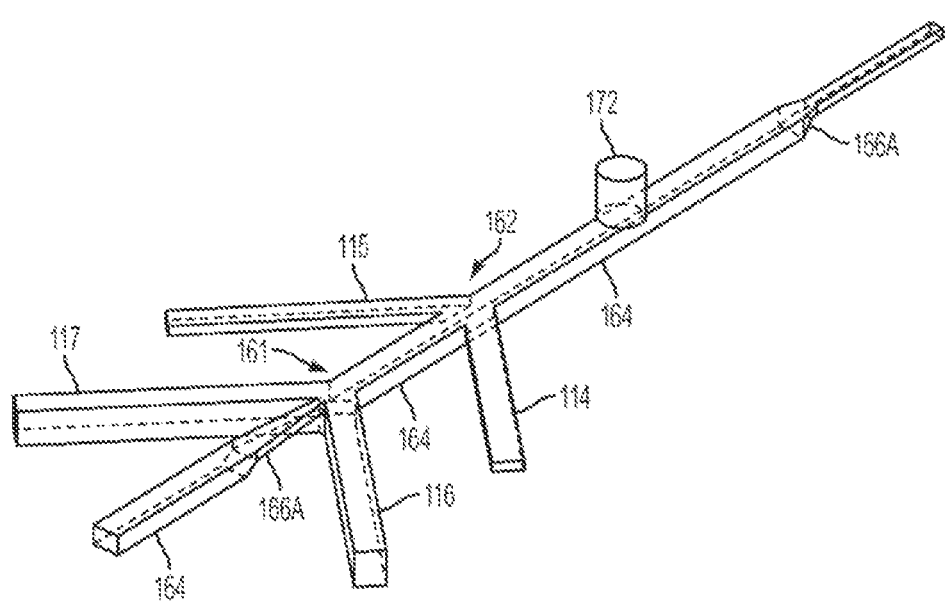
FIG. 3B shows a perspective view of the sample, and sheath or buffer channels in a single layer microfluidic chip, according to another embodiment consistent with the present invention.

In one embodiment, three-step hydrodynamic focusing is performed on the objects 160 in the chip 100. In this embodiment, as shown in FIGS. 1A and 3B, first two hydrodynamic focusing steps are accomplished by horizontally compressing the sample fluid stream 120 at intersections 161 and 162, and then in a third step, the sample fluid stream 120 is vertically compressed in the channel 164. Sheath or buffer channels 114, 115, and 116, 117 enter the channel 164 from a horizontal direction, at an angle of 45 degrees or less for each channel.

More specifically, in the first hydrodynamic focusing step, sample 120 flow enters into the first intersection 161, and the sheath or buffer fluids 163 from channels 116, 117 surround the sample 120 flow and immediately compress it into a thin sample 120 stream in channel 164. In one embodiment, the sample fluid channel 164 is tapered with an internal ramp prior to intersection 161, where sheath or buffer fluid channel 116, 117 enter the channel 164 (see FIG. 3B). Meanwhile, as the channel 164 is shallower (i.e., smaller in dimension) than the first sheath channels 116, 117, the sample 120 stream is lifted by the sheath or buffer fluid 163 from channels 116, 117, to flow to the top of the main channel 164.

In the second hydrodynamic focusing step, the sheath or buffer fluids 163 are introduced from channels 114, 115 into channel 164—the channel 114, 115 which are disposed close to the top of the main channel 164 (see FIG. 3B). In one embodiment, as shown in FIG. 3B, sheath or buffer channels 114, 115 join channel 164 horizontally, and may be of a smaller dimension from that of sheath or buffer channels 116, 117. Thus, since the depth of the channels 114, 115 are shallower than the main channel 164, the sheath or buffer fluids 163 further compress the sample 120 stream along the channel 164 width, to constrain the width of sample 120 stream. This sheath or buffer fluid 163 flow significantly improves the signal measurement sensitivity.

Without a third hydrodynamic focusing step, the lack of vertical compressing at intersections 161 and 162 may result in multiple objects 160 or cells simultaneously entering the detection region 129, thus, reducing the detection sensitivity or causing measurement errors, especially for a high throughput flow cytometry application.

However, three-dimensional hydrodynamic focusing is an effective way to align the objects 160 in a restricted core volume that may approximate a single file formation in channel 164. Further, the consistent positioning of the object 160 in the channel 164 results in minimum variability in velocity from object-to-object in the parabolic flow.

Figure 7:
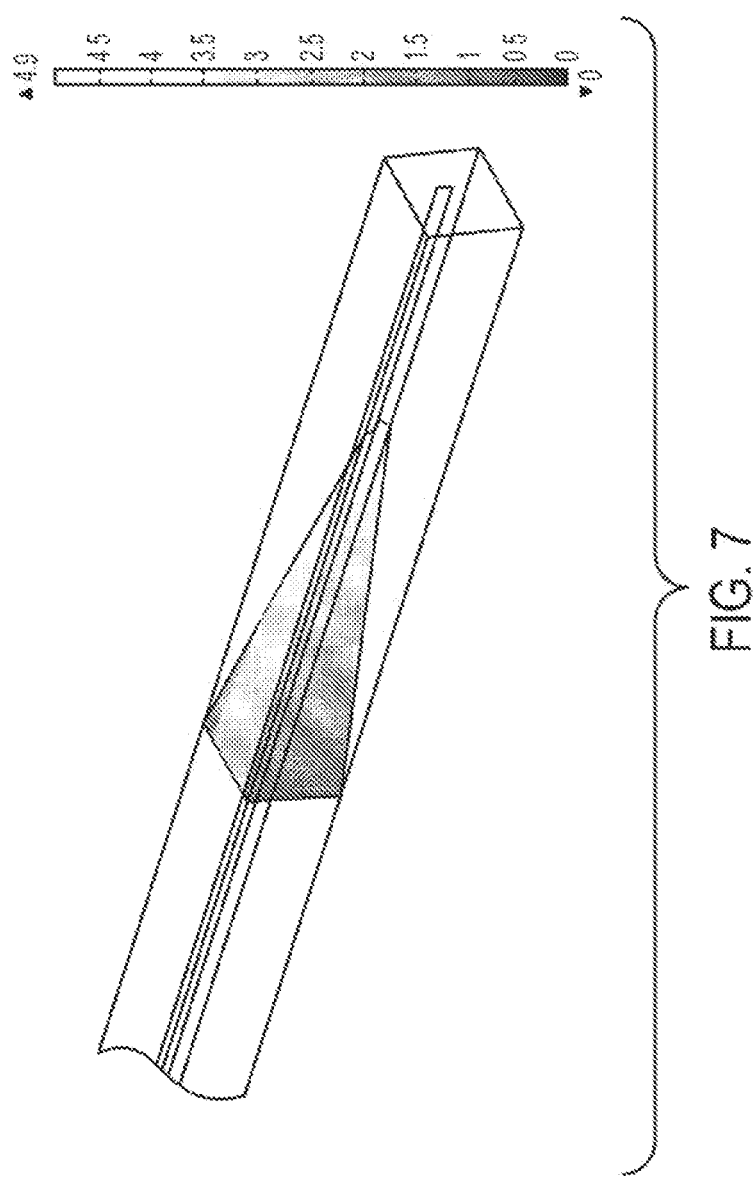
FIG. 7 shows a perspective view of the shear force gradient across the microfluidic main channel, according to one embodiment consistent with the present invention.

In microfluidic-based flow cytometry, the flow velocity profile is parabolic along the rectangular cross-section of the micro-channel. FIG. 7 illustrates the profile of shear force on the cross-section of the microfluidic channel 164. The shear force gradient shown in FIG. 7 has minimum shear force at the tapered tip and the larger region at the rear has the maximum shear value. Thus, the hydrodynamic shear force gradient is formed across the channel 164 cross-section. The large shear force close to the channel 164 wall helps to orient asymmetric objects 160.

In the present embodiment, after the first two steps of hydrodynamic focusing, the sample 120 flow shrinks into a very thin stream in both horizontal and vertical directions. The ratio of independently controlled sheath or buffer fluids 163 from channels 116, 117 and 114, 115, each determine the size of the resulting sample 120 stream in channel 164. After the compression caused by sheath or buffer fluid 163 from channels 114, 115, the objects 160 may spread a little along the channel 164 depth, but objects 160 still follow the sample 120 stream, which is very close to the top ceiling of the main channel 164 (note: with the chip described as horizontally disposed for ease of reference). Therefore, it is necessary to have a third sheath or buffer fluid 163 flow from channel 172 to further compress the sample 120 stream along the vertical direction, and confine the objects 160 well inside the thin, sample 120 stream.

Additionally, since the sheath or buffer fluid 163 flow is introduced perpendicularly to the pre-confined sample 120 stream from sheath or buffer channel 172, it helps to position the sample 120 stream to a location along the cross-section of the channel 164 (i.e., achieves an end result as shown in FIG. 8B). By fine-turning the flow rate of sheath or buffer fluid 163 from channel 172, the objects' 160 positions can be precisely controlled when they pass through the detection region 129.

In one embodiment, the sheath or buffer fluid 163 is introduced by channel 172 from external sheath tubing (see FIG. 20) instead of by micro-channels running through the microfluidic chip 100. Thus, an external flow controller is required to provide a constant and stable flow rate through the input channel 172 (see FIGS. 19-21).

The design of the present invention allows the core sample stream 120 to orient flat-shaped objects, position the objects 160 in the channel 164 in a physical arrangement approaching uniformity, all of which improves the downstream precision action of the focused energy apparatus 157.

Although three hydrodynamic focusing steps are disclosed above, one of ordinary skill in the art would know that the configuration and number of the sheath or buffer channels may change, as long as they achieve the desired features of the present invention, with respect to the orientation and focusing of the objects in the sample fluid 120.

Flow Control Methods

To realize the exemplary three-dimensional hydrodynamic focusing methods described above, both sample fluid 120 and sheath or buffer fluids 163 are required to be precisely delivered so that a constant flow can be streamed through the microfluidic chip 100. After being compressed by the sheath or buffer fluid flows 163, the objects 160 or cells have been accelerated and the average spacing between the objects 160 or cells in the sample 120 core stream is also stretched significantly therefrom. The ratio of the total sheath or buffer fluid 163 flow rate and the sample 120 flow rate can be adjusted between 100:1 and 1000:1. Preferably, the ratio of 200-400:1 is used in the microfluidic chip 100 of the present invention. The overall fluid flow rate in the microfluidic chip 100 is about 2-4 ml/min. The introduced sheath or buffer fluid flows 163 have to be constant and pulse-free to ensure a stable traveling speed of the objects 160 during interrogation and signal detection, and between the detection/interrogation position and the position of the action of the focused energy apparatus 157 (see FIG. 6A). This facilitates an accurate signal reading and action on the target object 160 by the focused energy apparatus 157. With the precise control of fluid flow through the main channel 164, the overall flow rate variation is less than 1% of set flow rate, and the travelling speed of target objects 160 for potential action by the focused energy apparatus 157 varies less than 1% from the position where interrogation and detection of objects 160 takes place, to the position where the focused energy apparatus 157 acts on the objects 160 (see FIG. 6A).

Orientation of Objects

One of the challenging issues in the detection of flat-shaped objects 160 (i.e., sperm cells) is to constrain the objects 160 in a uniform orientation when passing through the interrogation beam 148. Thus, an approximately uniform positioning of objects 160 and a corresponding orientation of objects 160 in the channel 164, helps to increase the sensitivity of the system. With the aforementioned hydrodynamic focusing strategy, the position of objects 160 along the channel 164 can be manipulated in a controlled way. Thus, by adjusting the ratio between the sheath or buffer fluid 163 flows from channels 116, 117, and 114, 115, and 172, a position of the focused sample 120 stream offset from the center of the channel 164 by about 5-20 microns (based on a channel 164 cross-section of 150 micron width, and 100 micron heights, for example), is preferred for the detection of flat-shaped objects 160. Generally, an adjustment of 0-100 microns bias position of the objects 160 can be achieved.

Specifically, in order to align objects 160 in the channel 164 to improve their orientation, the high aspect ratio of the microfluidic channel 164 is taken advantage of to induce the shear force to turn the flat surface of the object 160 (i.e., sperm cell) facing the channel 164 wall. Further, the sheath or buffer fluid 163 flow can be actively employed to compress and position the objects 160 in the channel 164. These methods are described below in more detail.

Passive Method

In one embodiment, an asymmetric geometry structure may be utilized to position the focused objects 160 in the channel 164, by one of: a) placing an asymmetric ramp 166B in the sample main channel 164 to lift the sample flow 120 (see explanation above regarding FIG. 4A); and b) placing an asymmetric ramp 166B in the main channel 164 prior to the action chamber 129 to lift up the focused sample stream 120 (see explanation above regarding FIG. 4B). The above asymmetric features can be used individually or in an appropriate combination of two or more. However, one of ordinary skill in the art would know that these features are not necessary to the achievement of the position of the objects 160 in the channel 164.

In one embodiment, as noted above, ramps may be used in the channels 114-117 to lift the sample flow 120, although they are not necessary. The placement of ramps in the channels is dependent upon the direction in which the objects 160 of the sample core stream 120 are required to be offset from the center to improve object 160 or cell orientation. However, the above passive method has less flexibility to vary the object 160 position in the main channel 164.

ii) Active Method

In an alternative method to offset the sample 120 core stream in channel 164, an asymmetric sheath flow 163 is introduced to adjust the positions of objects 160 or cells in the channel 164. There are several methods of realizing asymmetric sheath or buffer fluid flow 163, two embodiments of which are described below.

One embodiment is to introduce single sheath or buffer fluid flow 163 which forms a 90 degree angle with the main channel 164 wall, as shown in FIG. 3A (in a two-step hydrodynamic focusing method) or FIG. 3B (in a three-step hydrodynamic focusing method). In the two-step hydrodynamic focusing embodiment, the introduced sheath or buffer fluid flow 163 at the second-step hydrodynamic focusing intersection 162, further compresses the sample core stream 120 subsequent to the first-step hydrodynamic focusing at intersection 161.

In the alternative three-step hydrodynamic focusing embodiment, this compressing of the sample core stream 120 occurs at the third-step hydrodynamic focusing intersection where channel 172 joins main channel 164. Thus, the final hydrodynamic focusing step positions the objects 160 or cells to a desired location along the vertical axis. By controlling the ratio of the hydrodynamic focusing flow rates, a desired position of the objects 160 can be obtained to achieve the optimum orientation.

Figure 12A:
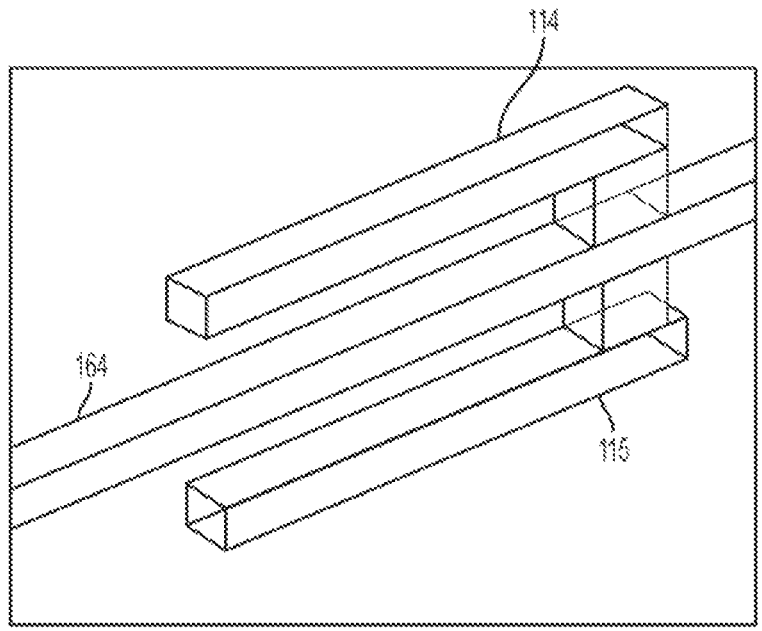
FIG. 12A shows the second hydrodynamic focusing step, where sheath or buffer channels parallel the sample channel of a microfluidic chip, from above and below, and enter the sample channel from vertical directions, according to one embodiment consistent with the present invention.
Figure 12B:
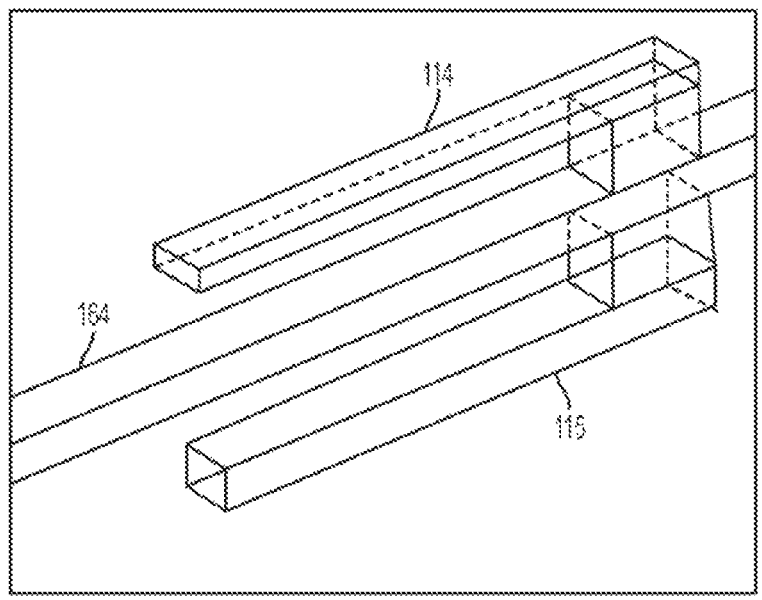
FIG. 12B shows the second hydrodynamic focusing step of FIG. 12A, with one sheath or buffer channel of a microfluidic chip, being smaller than the other channel, according to another embodiment consistent with the present invention.

In a second embodiment using the two-step hydrodynamic focusing method, two second-step sheath or buffer channels 114, 115, merge in an angle to the main channel 164 wall, and parallel main channel 164 from above and below, as shown in FIGS. 12A-12B. The angle of the second-step hydrodynamic focusing channels 114, 115 and main channel 164 may vary and is dependent upon the fabrication methods. Preferably, a 90 degree angle is selected (see FIGS. 12A-12B). Different flow rates of sheath or buffer fluids 164 may flow via the two channels 114, 115, which are capable of repositioning the sample core stream 120 in the main channel 164. After the objects 160 are offset from the central plane of the channel 164, orientation of the objects 160 are improved. In a specific embodiment such as sperm cells 160, the sperm cells 160 tend to turn their flat sides to the channel 164 wall in the vertical axis.

As can be seen from the embodiment of FIG. 12B, the dimensions of the channels 114, 115 are not necessarily identical (as shown in FIG. 12A), in order to obtain different hydraulic resistances. Thus, the same flow rate of the second-step sheath or buffer fluid flows 164 in the channels 114, 115 will also generate bias fluid flow as well.

To summarize, both of the passive and active methods above can help to optimally position the objects 160 and improve their orientation in the channel 164.

In one embodiment, pancake-shaped sperm cells 160 are taken as an example of the objects 160. Because of their pancake-type or flattened teardrop shaped heads, the sperm cells 160 will re-orient themselves in a predetermined direction as they undergo the second, or third (depending on the embodiment) focusing step—i.e., with their flat surfaces perpendicular to the direction of light beam 148 (see FIG. 6). Thus, the sperm cells 160 develop a preference on their body orientation while passing through the hydrodynamic focusing process. Specifically, the sperm cells 160 tend to be more stable with their flat bodies perpendicular to the direction of the compression. Hence, with the control of the sheath or buffer fluids 163, the sperm cells 160 which start with random orientation, now achieve uniform orientation. Thus, the sperm cells 160 are not only disposed in a restricted core volume at the center of the channel 164B, but they also achieve a uniform orientation with their flat surface normal to the direction of compression in the last hydrodynamic focusing step.

Figure 13A:
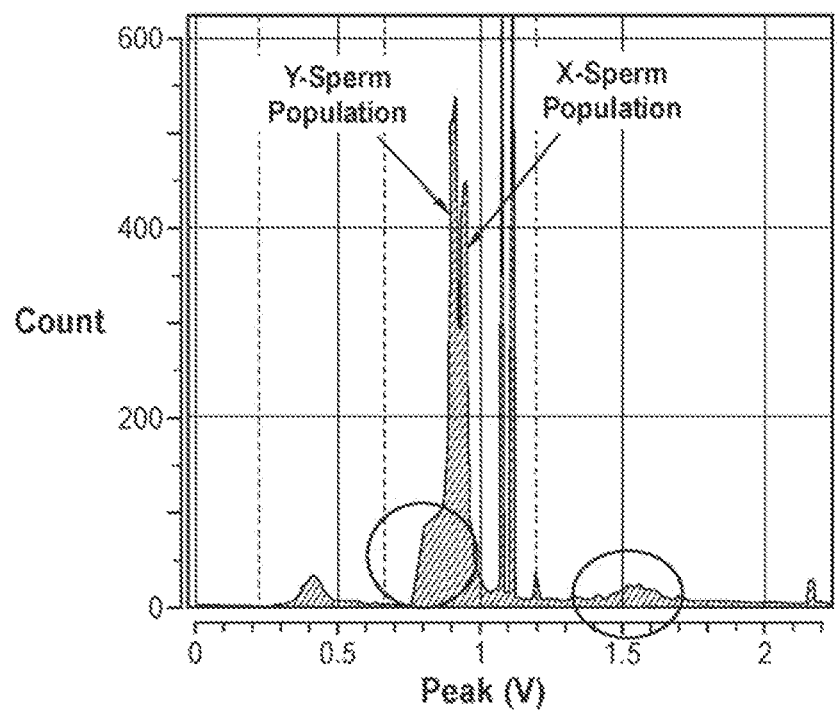
FIG. 13A shows a histogram of sperm cells in a center of the main channel of a microfluidic chip, according to one embodiment consistent with the present invention.
Figure 13B:
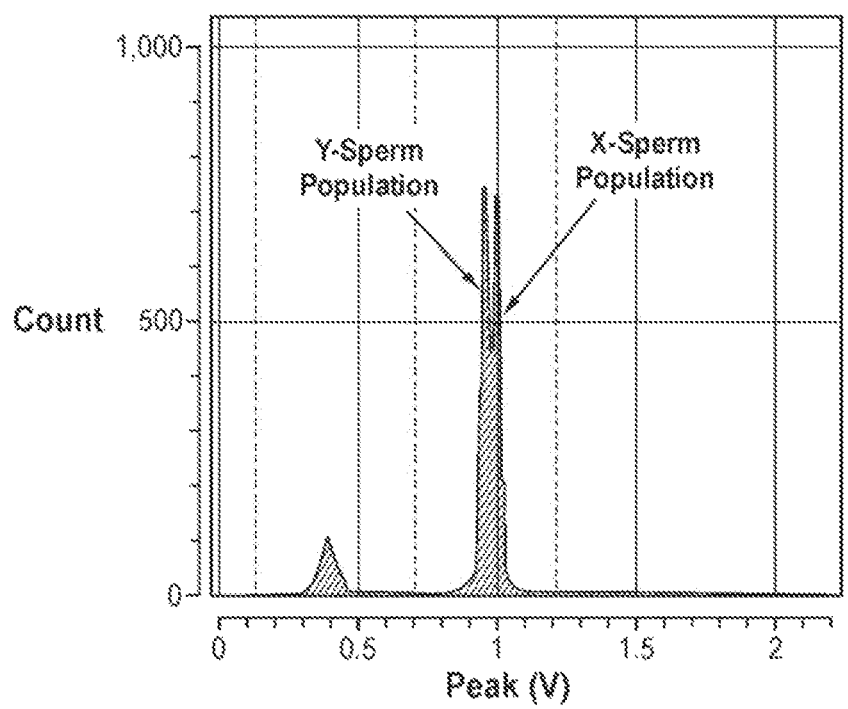
FIG. 13B shows a histogram of sperm cells offset from a center of the main channel of a microfluidic chip, according to one embodiment consistent with the present invention.

The above methods improve the sperm cells' 160 orientation and the capability to differentiate the DNA content of X- and Y-sperm chromosomes (and thereby distinguish between X and Y sperm). The histograms of FIGS. 13A and 13B show the sperm cells 160 in the center of the channel 164, and offset from the center of the channel 164, respectively. The circles on the left and right of the histogram in FIG. 13A shows the populations of mal-orientated sperm cells 160. The left hump of the major population weakens the capability to differentiate X- and Y-sperm populations and contributes to the asymmetric distribution of X- and Y-sperm populations.

Operation of Microfluidic Chip System

Interrogation of Objects

In one embodiment, the interrogation light source 147 is an excitation laser 147 (see FIG. 16), having 350 mW power, 355 nm wavelength, 12 ps pulse width.

In one embodiment, further downstream from the hydrodynamic focusing steps, in channel 164, the objects 160 are detected in the action chamber 129 at opening 150 through covering 133, using the light source 147. Light source 147 emits a light beam 148 (which may be via an optical fiber) which is focused at the center of the channel 164 at opening 150.

In one embodiment, the objects 160 are sperm cells 160, which are oriented by the hydrodynamic focusing steps, such that the flat surfaces of the sperm cells 160 are facing toward the light beam 148. In addition, all objects 160 or sperm cells 160 are moved into a restricted core volume that may approximate a single file formation, by the hydrodynamic focusing steps, as they pass under light beam 148. As the objects 160 pass under light source 147 and are acted upon by light beam 148, the objects 160 emit the fluorescence which indicates the identity of the desired objects 160.

The light source 147 provides the fluorescence excitation energy for detection of objects 160 in the action region 129. In one exemplary embodiment with respect to the objects 160 being sperm cells 160, X chromosome cells fluoresce at a different intensity from Y chromosome cells (based on DNA content, as is well known in the art) (note: 355 nm is selected for the Hoescht 33342 dye used on the DNA). Further, in other embodiments, objects 160 which are cells carrying one trait may fluoresce in a different intensity or wavelength from cells carrying a different set of traits. In addition, the objects 160 can be viewed for shape, size, or any other distinguishing indicators.

Thus, in the embodiment of sperm cells 160, the illumination to the flat surface and the edge of the cells 160 is quite different with sperm cells 160 as compared to other cells. The fluorescence signal derived from the edge of the sperm cells 160 is significantly stronger than that from the flat surface, which increases the difficulty for the digital processor 156 to deal with the stronger signal from the edge, and the normal lower signal from the X- and Y-flat surface of the cells 160. Thus, turning the flat surface of the sperm cell 160 to face the laser illumination (i.e., light beam 148) helps to reduce the orientation variability and increase the capability of the system to differentiate X- or Y-sperm cells 160.

In the embodiment of beam-induced fluorescence, the emitted light beam 151 (in FIG. 5) is then collected by the objective lens 153, and subsequently converted to an electronic signal by the optical sensor 154. The electronic signal is then digitized by an analog-digital converter (ADC) 155 and sent to an electronic controller 156 for signal processing.

As noted above, in one embodiment, the DSP-based controller 156 monitors the electronic signal, and when a particular signal is noted, a focused energy apparatus 157 may be employed to act upon a target object 160 (see FIGS. 6A-6C). However, in an alternative embodiment, the interrogation apparatus interrogates the objects 160 after they are acted upon by the focused energy device 157 (see FIG. 6D).

In one embodiment, interrogation of the sample 120 containing objects 160 (i.e., biological material), is accomplished by other methods. Thus, portions of, or outputs from, the microfluidic chip 100 may be inspected optically or visually. Overall, methods for interrogation may include direct visual imaging, such as with a camera, and may utilize direct bright-light imaging or fluorescent imaging; or, more sophisticated techniques may be used such as spectroscopy, transmission spectroscopy, spectral imaging, or scattering such as dynamic light scattering or diffusive wave spectroscopy.

In some cases, the optical interrogation region 129 may be used in conjunction with additives, such as chemicals which bind to or affect objects 160 of the sample mixture 120, or beads which are functionalized to bind and/or fluoresce in the presence of certain materials or diseases. These techniques may be used to measure cell concentrations, to detect disease, or to detect other parameters which characterize the objects 160.

However, in another embodiment, if fluorescence is not used, then polarized light back scattering methods may also be used. Using spectroscopic methods, the objects 160 are interrogated as described above. The spectrum of those objects 160 which had positive results and fluoresced (i.e., those objects 160 which reacted with a label) are identified for selection by the focused energy apparatus 157.

In one embodiment, the objects 160 may be interrogated and identified based on the reaction or binding of the objects 160 with additives or sheath or buffer fluids 163, or by using the natural fluorescence of the objects 160, or the fluorescence of a substance associated with the object 160, as an identity tag or background tag, or meet a selected size, dimension, or surface feature, etc.

In one embodiment, upon completion of an assay, selection may be made, via computer 182 (which monitors the electronic signal and employs the focused energy apparatus 157) and/or operator, of which objects 160 to discard and which to collect.

Applications for Focused Energy Apparatus

The focused energy apparatus 157 of the present invention may carry out a number of actions on the objects 160 in channel 164, or between chip 100 and container 188.

In one embodiment, the focused energy device 157 acts to photodamage or destroy the objects 160 in a number of ways.

Specifically, the focused energy apparatus 157 acts to kill objects 160 (i.e., cells). For example, the target objects 160 may be unwanted cells 160, and upon action by the focused energy apparatus 167, cellular death may be caused by overheating of the intracellular environment, which may promote, but is not limited to, protein denaturation or reduction in enzyme activity.

In another method, the action of the energy dosage 158 from the focused energy apparatus 157 is strong enough to cause rupture of the plasma membrane and leaking of the cellular contents out of the cell 160 and into the surrounding environment (i.e., sheath or buffer fluid 163).

In another method, object 160 or cell death can be caused by the formation of radical oxygen species (ROS) due to adsorption of energy from the focused energy pulses 158 from the focused energy apparatus 157, which will cause, among other things, DNA and protein damage.

In another embodiment, the focused energy apparatus 157 can temporarily or permanently disable target objects 160, such as cells 160, using focused energy pulses 158 from the focused energy apparatus 157.

For example, exposing sperm cells 160 to focused energy pulses 158 such as those produced by a laser or LED 157 generates photo-activation within the cells 160 and results in temporary or permanent disablement of cellular mechanisms responsible for sperm 160 motility. After disabling target sperm cells 160, the resulting sample 120 contains motile sperm 160 and immotile (target) sperm 160, where the immotile sperm are unable to fertilize oocytes naturally.

In another embodiment, it may be desirable to use focused energy pulses 158 to make sperm 160 infertile through the dimerization of nucleotides in the DNA. Dimerization occurs when cells 160, such as sperm cells 160, are exposed to UV light, causing bonds between pyrimidine bases, and resulting in a type of "cross-linking", which, if not repaired, inhibits replication and transcription. Thus, although the target sperm cells 160 are still alive as evidenced by their motility, the fertility of the targeted sperm cells 160 is greatly reduced.

In addition to sperm cells 160, one can use high powered focused energy sources 157 such as LEDs or lasers 157 to photobleach fluorescence in objects 160, such as cells or colloids 160, which express a predetermined level of fluorescence. For instance, in many self-assembly object formulations, a wide size range of objects 160 are formed that are difficult to separate from each other. To produce an enhanced sample 120 of objects 160 having a desired size, one can fluorescently label all objects 160 using methods known in the art, and one can use optical interrogation to determine object 160 size, and photobleach objects 160 possessing the predetermined level of fluorescence.

In a specific example, a semen sample 120 may contain contaminants such as bacterial or viral cells, which are the target of photobleaching. Another example may include sperm cells 160 containing a given trait of the cell 160 or DNA and labeled with the fluorophore for quantitative and/or qualitative measurement. Sperm cells 160 containing the trait may be targeted by the focused energy apparatus 157. In another embodiment, sperm cells 160 which do not contain the trait may be targeted for photobleaching. Specific cells 160 in other cell mixtures such as blood, are also candidates for photobleaching treatments to reduce viability. In yet another embodiment, photobleached cells/objects 160 can be undetectable downstream and therefore, are not subject to subsequent processing steps (i.e., can by-pass subsequent processing steps).

In another embodiment, in contrast to the disabling of objects 160, focused energy pulses 158 can be used to activate materials such as caged molecules or compounds within the objects 160.

In one application, the caged compounds represent, but are not limited to, fluorescent markers or cell responsive molecules. In these applications, focused energy pulses 158 are used to cause photo-activation of the caged molecules or compounds which alters cell 160 signaling kinetics for ex-vivo therapies.

In another embodiment, focused energy pulses 158 can activate photo-polymerization events which disable cells or colloids 160 by altering internal properties of the object 160.

In another embodiment, with respect to intracellular signaling pathways, focused energy pulses 158 are used to activate heat shock proteins or induce mitochondrial biogenesis or activation within objects 160 or cells, including germ cells, to enhance cellular viability and functionality. Additional intracellular pathways may also be activated to repair damage done by either the interrogation/detection device 147 or a number of other factors that are too numerous to list (i.e., environmental, heat, chemical, etc.)

In one embodiment, one skilled in the art can generate photo-polymerization through focused energy pulses 158 to temporarily encapsulate or permanently contain target cells 160, colloids, or other objects, using multi-armed PEG-acrylate/PEG-vinyl/etc., which promotes encapsulation of the target objects 160 or cells. Sperm cells 160 can be encapsulated to enhance the preservation of viability and fertility through commercial storage and delivery processes.

In another embodiment, focused energy pulses 158 are used to cause photo-polymerization events on the surface of targeted cells or objects 160 which increase the size or density of the encapsulating material in order to alter the size or density of the target object 160 or improve properties and performance of the encapsulating material.

In another embodiment, a photopolymerizable sequence in the hydrophobic portion of the vesicle may be used to permanently seal the desired molecule or object 160 by encapsulation therein.

In another method, the focused energy apparatus 157 may be used to act on externally or alter the environment around the target objects 160.

In one method, focused energy pulses 158 are used to heat the local environment around target cells or objects 160 so that the thermal enhancement is sufficient to cause toxicity to target cells 160.

In another embodiment, focused energy pulses 158 are used to promote rupturing of analyte containing delivery vehicles (such as vesicles) which are in close proximity to target cells 160. The delivery vehicles carry molecules such as sodium fluoride (NaF) which causes temporary immobility of sperm cells 160, or heparin which promotes capacitation of spermatozoa 160. When the concentration of analytes or activating agents are increased locally, target sperm cells 160 or other objects respond to the local signals without activating similar responses in non-target cells 160.

In another embodiment, when objects 160 or cells are attached to a surface, the surrounding environment is modified with focused energy pulses 158 to vary the modulus of elasticity of the surface or release cell responsive chemicals from the surface of surrounding objects 160 or cells.

In one embodiment, heat production through absorption of light/EM waves 158 causes a temperature change which kills the objects 160 or cells.

In another embodiment, focused energy pulses 158 are used to form predetermined chemical bonds or break chemical bonds in the attachment material, thus, directing the differentiation of objects 160, such as stem cells 160, into differentiated cell lines.

In one embodiment, for some applications, it is desirable to use focused energy pulses 158 to promote cellular uptake or adhesion onto target objects 160.

In one embodiment, cellular uptake of antibodies, cellular probes, or DNA is enhanced through local heating.

In one embodiment, with said local heating, when the temperature increase is optimized also to maintain object 160 or cell viability, the internalization of objects 160 into target viable cells 160 is selectively promoted.

In one embodiment, the object 160 to be delivered is attached to an object, that when targeted with a light source 147, may cause a brief microbubble. For instance, an oligonucleotide may be conjugated to a gold nanoparticle. When the gold is heated with a light source 147 at an optimized wavelength, a microbubble is briefly formed. Upon cavitation of the microbubble, the gold nanoparticles is broken apart and the pieces of the nanoparticle and the object attached to it are permeabilized through a cell membrane.

In another embodiment, the temperature increase of the target object 160 is not sufficient to cause the formation of a microbubble. The localized temperature increase is optimized to maintain cell viability and selectively promote the internalization of objects 160 into target viable cells.

Similarly, in another embodiment, by using focused energy pulses 158 to adhere materials onto colloids or objects, object 160 geometry or object 160 properties is altered, thus, enabling additional separation techniques, such as magnetic or electric fields to separate materials that are normally not susceptible to such forces.

Operation of Focused Energy Apparatus

Generally, flow cytometric analysis and action systems that use an electromagnetic radiation source such as a focused energy apparatus 157 or laser, to act on selected objects 160, typically desire to deliver a controlled energy level to individual objects 160. In one embodiment, such systems can kill, alter, damage, or destroy targeted objects 160 or cells using the focused energy apparatus 157. In other embodiments, such systems can, among other methods, activate targets in selected objects 160 or cells or in the fluid, media, or matrix surrounding selected objects 160, as described above.

In the above methods which utilize focused energy pulses 158, radiation can be applied by methods of either targeted firing or continuous elimination, such that the desired objects 160 are unaffected, and the unwanted, altered, killed, destroyed or damaged objects 160 are discriminated from the sample 120. Similar considerations as noted above, are given when selecting laser wavelength and laser power for targeted firing and continuous firing modes.

Targeted Firing

More specifically, in targeted firing, the focused energy apparatus 157 is employed for targeted objects 160. Specifically, an object 160 in a sample 120 fluid mixture, may pass through an interrogation/detection area in chamber 129, for example, where specified characteristics of the object 160 are evaluated by one or more of the above methods.

Thus, in a flow based system, for example, the focused energy apparatus 157 action area 129 is downstream from the optical interrogation area using light source 147 for interrogation. Alternatively, the focused energy apparatus 157 is utilized prior to interrogation further downstream. In one embodiment, the focused energy apparatus 157 acts on the objects in action chamber 129. The distance between the optical interrogation region and the action region may be adjusted to accommodate different timings.

Based upon predetermined criteria, a decision is made to either keep, discard, or act upon the selected object 160. Objects 160 marked for action, are hit with a triggered pulse of energy 158 from the focused energy apparatus 157 (see FIGS. 6A-6C, for example).

When the object 160 or cell is not targeted, it remains unaffected, and flows through the chamber 129, via channel 164 to output channel 141 and container 188, which collects target and non-target objects 160 as a discriminated product 165.

In one embodiment, the laser pulse 158 has a short duration and can selectively target individual objects 160 or cells while exerting no intended impact on non-target objects 160 or cells which may be nearby, thus, avoiding "overspray" to non-target objects 160 or cells. Pulse energy is selected to impart the desired effect while avoiding undesired disturbances to the surrounding media, or for example, in flow systems, does not cause unintended cavitation or bubble formation. A variety of laser wavelengths can be used; however, the flux requirement may be different depending on the characteristics of the target object 160, dye, and environment.

Laser units 157 have limited power, especially those compact models that operate at high pulse frequency (>100 kHz typically), and it may be preferable to choose a laser wavelength that minimizes the required flux. For example, matching the laser 157 wavelength to the absorbance of dyes, other targets, or objects 160 (i.e., molecules) used in the action process greatly improves efficiency and effectiveness. Additionally, pulse energy 158 is selected to impart the desired effect while avoiding undesired disturbances to the surrounding media, or for example, in flow systems, not causing unintended cavitation or bubble formation.

Figure 26:
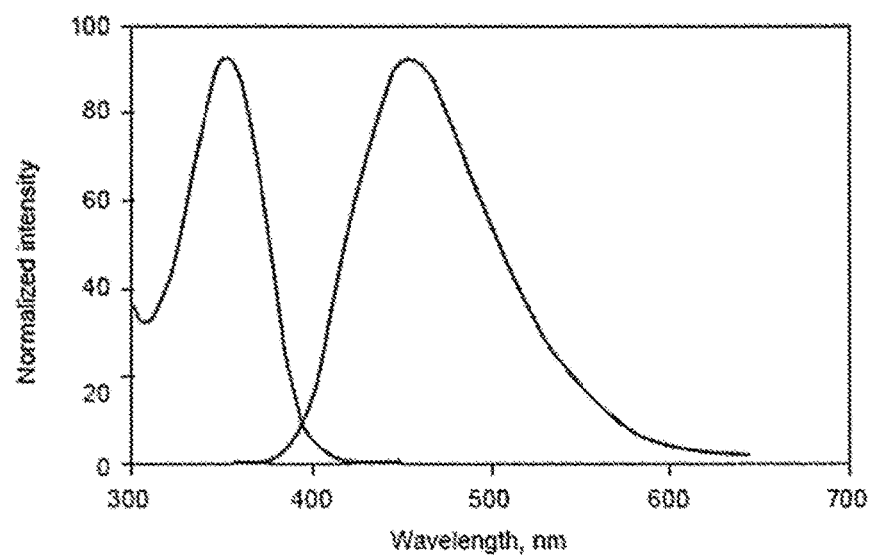
FIG. 26 shows the excitation wavelength and the emission wavelength for cells stained with Hoescht 33342.

In one specific example related to sperm cells 160 as the objects 160, a 355 nm laser 157 was used to take advantage of the dye (i.e., Hoechst 33342 dye) used for the cell staining process. In a similar example, a 349 nm laser 157 may be used. In such examples, when unwanted sperm cells 160 are photodamaged, destroyed or killed, pulse energy levels of 0.5-8.0 pJ are used. FIG. 26 shows the excitation wavelength and the emission wavelength for cells stained with Hoescht 33342.

b. Continuous Firing:

In continuous firing, such as in a flow-based system, the focused energy pulse 158 is constantly employed and only interrupted for the passage of the non-target objects 160 (i.e., wanted objects 160 that are not to be damaged, destroyed, altered or killed), or debris or contaminants which do not require action thereon.

As stated above, based upon predetermined criteria, a decision is made to either keep or discard an object 160, or act upon, including photodamage, kill, alter, disable, or destroy an object 160. The focused energy apparatus 157, such as a continuous wave (CW) or rapidly pulsed laser or LED, delivers a continuous stream of focused energy 158 to the objects 160, and is used to act upon (i.e., including, photodamage, alter, disable, destroy, or kill) every object 160 passing through a particular location in the flow stream of the sample 120 fluid flow in an exemplary flow system. When non-target objects 160 are encountered in the action region, the laser beam 158 is shut off, deflected, or otherwise interrupted for a short period of time, to allow the non-target objects 160 (in some cases, discarded items), to pass through unaffected. The objects 160—target or non-target—flow through channel 141 into container 188.

Methods for interrupting or diffusing the beam 158 include mechanical (shutters, choppers, galvanometer mirror), optical (acoustic optic deflector, acoustic optic modulator, spatial light modulator, digital micro-mirror device, polarization modification, liquid crystal display), electronic (pulse conditioning, dropping, or alteration of a Q-switch laser), or acoustic. Any other known or future suitable methods or techniques may be utilized to interrupt the focused energy beam 158.

With either targeted or continuous methods, the energy pulse 158 has a short duration and the focused energy apparatus 157 can selectively target only a single object 160 and not impact other objects 160 which are nearby in the sample 120 fluid flow (i.e., can limit "collateral damage"). The energy pulse 158 is selected to be sufficient to achieve the desired action on the object 160 (i.e., damage, alter, kill or destroy the object 160), per user requirements. The pulsed energy 158 from the focused energy apparatus 157 should fall within a range where it will not cause a disturbance to the sample 120 fluid due to cavitation, bubble formation, or method of energy absorbance.

Other technologies for reducing unintended action, damage, and destruction to non-target objects 160 include those which absorb a significant portion of the pulse energy 158, alter the direction of the beam 158, or discharge excess energy by firing pulses 158 into the flow stream 120. Specifically, these can include mechanically moving a mirror or lens so as to defocus or deflect excess laser pulses 158 into an energy absorptive device, lenses altered electronically in order to change the laser's 157 propagation angle, and sophisticated triggering technologies which coordinate pulse energy data from the laser 157 with data about the object-to-object timing of objects 160 in the immediate flow stream.

c. Pulse Timing

The timing between actions by the focused energy device 157 on the objects 160 is not uniform and follows a Poisson distribution where many short and extremely long intervals occur. Because a laser-based action system 157 includes inherent limiting factors, it is preferable to include a short "recharge time" between laser pulses 158. The latency time (inherent in the focused energy apparatus 157), plus the "charge/recharge" time, is the minimum time that the focused energy apparatus 157 can react (deliver a pulse) and still provide the required energy level to the targeted object 160.

In one embodiment, charge time should range from 0.1 μs to 1 second, and preferably should be from 0.1 μs to 4 ms. Pulse-to-pulse variability in energy levels affects the rate of producing the desired effect on target objects 160 or cells, and the potential for impacting non-target objects 160 or cells. When fired at non-uniform intervals, pulse-to-pulse stability should be high. In one example, a Q-switch laser 157 in pulse-on-demand mode was used to deliver average pulse energy of 1.8 μJ with a range for individual pulses of 1.3 μJ to 2.3 μJ.

In a flow based system, the action region 129 may be located downstream from the optical interrogation region in the chamber 129, or upstream thereof, and the distance between the optical interrogation region and the action region may be adjusted to accommodate different timings. To accommodate sufficient charge time for a pulsed laser 157, the minimum timing between interrogation of the objects 160 or cells, and action on selected objects 160 or cells, should be no less than 1 μs.

The focused energy apparatus 157 operates successfully, for substantial periods, at action rates up to 5,600 objects per second, with accuracy rates which can be selected, and range for example, from 75-95%. In systems where spacing between objects 160 in the flow stream is controlled, the system 157 can operate at action rates up to the repetition rate of the laser 157.

Selection of Objects

In one embodiment, the focused energy apparatus 157 is employed prior to interrogation of the object 160. However, in another embodiment, in order to determine which objects 160 are selected for action by the focused energy apparatus 157, as noted above, a histogram, or any graphical representation of the measured/calculated characteristics of the objects 160 after interrogation, can be used in order to make the decision for action thereof on the population of objects 160. In one embodiment, after interrogation is accomplished, the plot of the span (i.e., transit time through the interrogation region of the chamber 129) can reflect the relative size of the sample 120 core stream under different flow conditions, object 160 or cell distribution across the main channel 164, and object 160 traveling velocity, as well as the variation of object 160 velocity within a particular chip 100 design.

As noted above, the high aspect ratio of the main channel 164 is important to object 160 or cell hydrodynamic focusing, migration, and orientation. In one embodiment, less than one for the high aspect ratio for the microfluidic channel 164 is used in the present invention. Preferably, 2/3 high aspect ratio is used for the main channel 164. The value of the span itself roughly indicates the object 160 velocity. Large span value indicates that objects 160 pass the interrogation light beam 148 slowly. The tight size of the span indicates that the sample 120 core stream is closer to the channel 164 central plane and there is less object 160 velocity variation.

In one embodiment, to precisely act on the selected objects 160 whether flowing through chip 100 or departing from output 112, less velocity variation of objects 160 is allowed to ensure that the focused energy apparatus 157 can precisely target the selected objects 160 or cells. Thus, based on the above-described positioning and orientation methods (i.e., active, passive methods), the objects 160 are positioned close to the center of the cross-section of the channel 164 to reduce the velocity variation of the objects 160.

Figure 9:
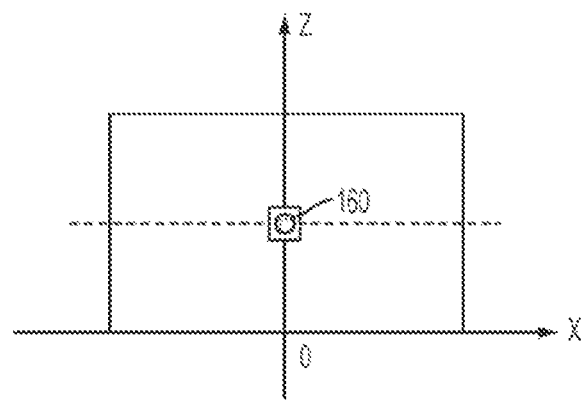
FIG. 9 shows a cross-section of the main channel of the microfluidic chip, with an object in the center thereof, according to one embodiment consistent with the present invention.
Figure 10:
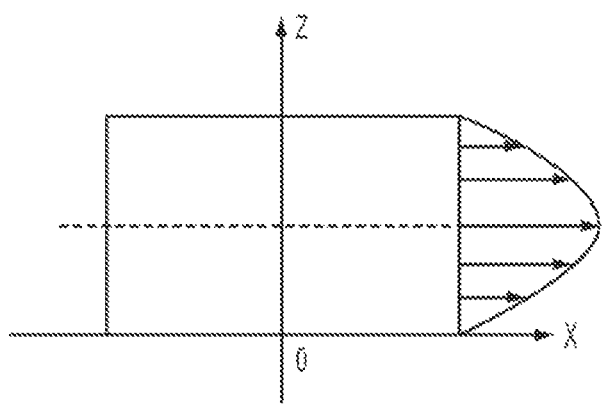
FIG. 10 is a diagram showing a flow velocity profile across the main channel of a microfluidic chip, according to one embodiment consistent with the present invention.
Figure 11:
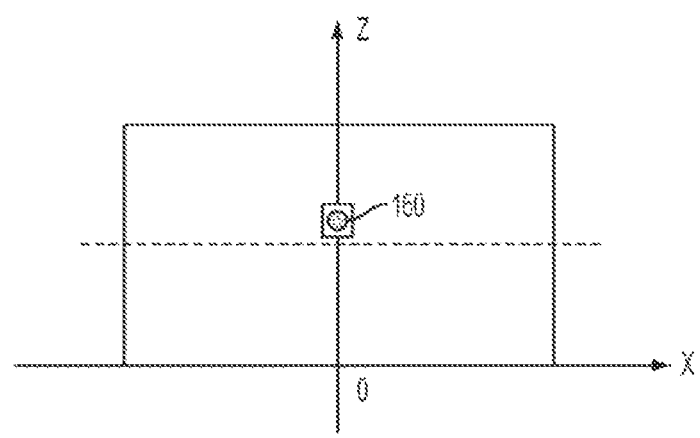
FIG. 11 shows a cross-section of the main channel of a microfluidic chip, with an object offset from the center, according to one embodiment consistent with the present invention.

In one embodiment, for flat-shaped object 160 or cells, such as live sperm cells 160, both orientation and velocity variation need to be taken into consideration. Thus, sperm cells 160 pushed offset from the central plane of the channel 164 along the vertical axis (see FIG. 9B), tend to obtain a better resolution (e.g., the differentiation of X- and Y-sperm cells 160 is more than 50% separated on the histogram obtained after interrogation), and a less mal-oriented cell 160 population. Thus, resolution and target (i.e., photodamage, killing) efficiency are balanced, with, in one exemplary embodiment, the sample 120 core stream being preferably shaped into about 10 microns in width, and 5-10 microns in height of the main channel 164 across the cross-section of the main channel 164 in the interrogation/detection region of chamber 129, and offset by about 2-10 microns from the central plane of the main channel 164, preferably by controlling the hydrodynamic focusing steps.

In one embodiment, where the objects 160 are sperm cells, a target sperm cell 160 may be a male-bearing sperm cell (i.e., a Y chromosome-bearing sperm cell) and a non-target sperm cell 160 may be a female-bearing sperm cell (i.e., an X chromosome-bearing sperm cell). In another embodiment, a target sperm cell 160 may be a female-bearing sperm cell (i.e., an X chromosome-bearing sperm cell) and a non-target sperm cell 160 may be a male-bearing sperm cell (i.e., a Y chromosome-bearing sperm cell).

Figure 6D:
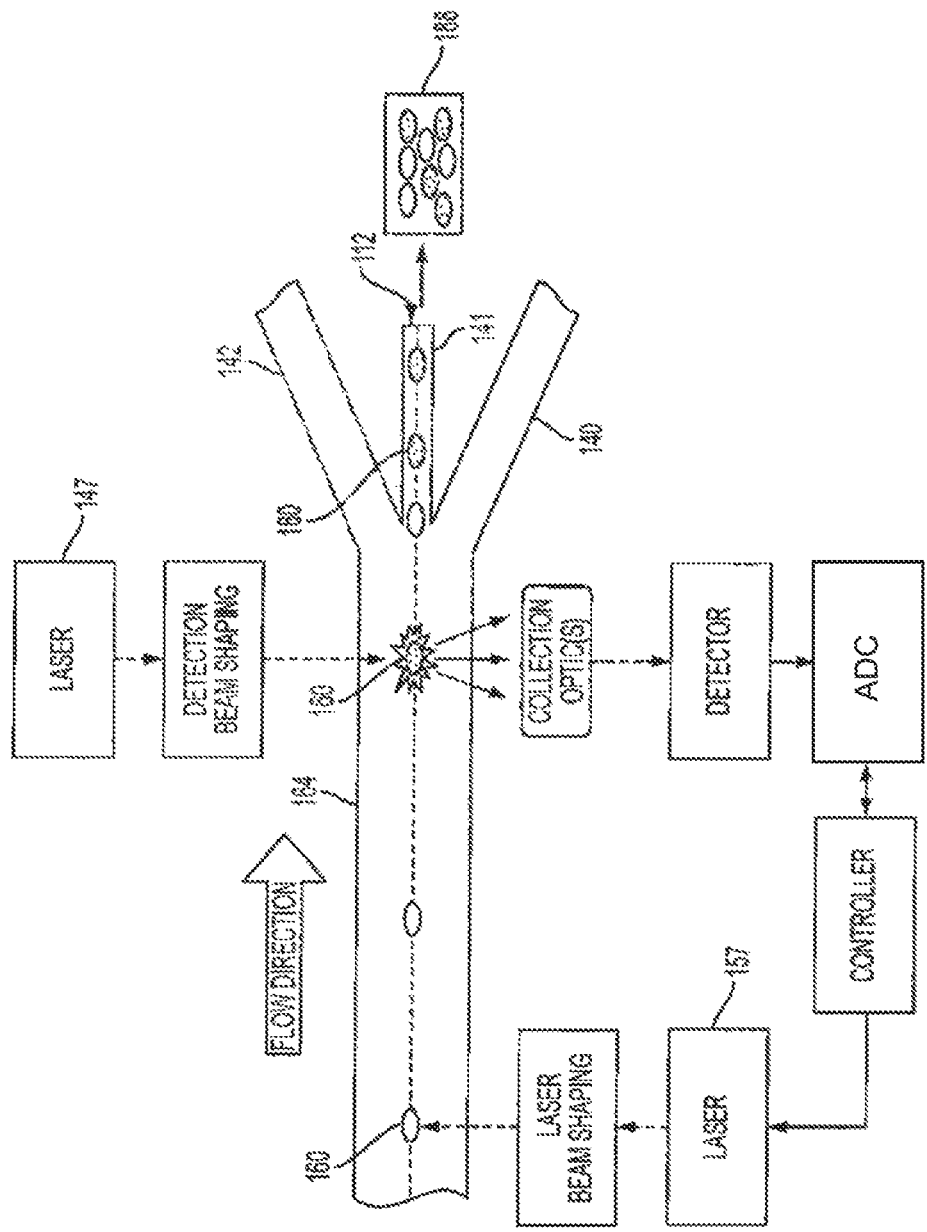
FIG. 6D shows a slanted, schematic side view of the flow of objects in the main channel of a microfluidic chip system, from interrogation to discrimination, with activation of the focused energy device prior to interrogation, according to another embodiment consistent with the present invention.

In one embodiment, the objects 160 are acted upon prior to interrogation, by utilizing localized heat shock to incorporate molecules such as DNA or other probes through protective outer layers and into objects—i.e., through protective membranes and into cells (see FIG. 6D). Traditional methods for incorporating molecules using the high voltages requires for successful electroporation to permeabolize membranes may be desirable, as evidenced by the high cell mortality rates. Localized heat shock represents a more gentle procedure and therefore, may be more desirable for maintaining viability of the cells. The focused energy apparatus 157, is used to generate a localized rise in temperature, thus achieving heat shock. The localized heat shock results in permeabolizing the objects 160, thus, facilitating incorporation of the desired molecules. An interrogation apparatus 147 is used thereafter, to detect and interrogate the objects 160 from which the interrogation apparatus 147 determines the number or proporation of objects 160 for which incorporation of the molecules has been attained. This method may be particularly desirable in biodetection, cellular engineering, targeted therapeutics, and drug/gene delivery.

e. Action Zone

In one embodiment, after interrogation is performed, and after an acceptable histogram is obtained (i.e., with acceptable resolution and relatively small span distribution), then the decision is made to employ the focused energy apparatus 157 to act on the selected objects 160 or cells. One of the more important parameters is the timing setting for the pulse from the focused energy apparatus 157 (i.e., delay or time interval for the object 160 between the interrogation/detection beam 148 and the focused energy beam 158).

The focused energy apparatus 157 action zone is the area in the cross-section of the main channel 164 where the selected objects 160 or cells can be effectively acted upon (i.e., photodamaged, altered, disabled, killed, destroyed etc.), as shown in FIG. 16. Based on a predetermined energy level and beam shape of the focused energy apparatus 157, and on the microfluidic channel 164 design and flow conditions, the action zone can be estimated by an action percentage (e.g., <97%). The energy level of the focused energy apparatus 157 is dependent upon the current and charging time of the focused energy apparatus 157. The larger overall flow rate in the main channel 164 means that the objects 160 are traveling faster. Thus, the transit time of the objects 160 through the focused energy beam 158 is shorter. For example, for an energy level of the focused energy apparatus 157 of 2.3 tJ with a certain beam shape (e.g., 2.5 microns×15 microns), and object 160 traveling velocity around 7.5 m/s, the focused energy apparatus 157 action zone is estimated to be about 20 microns in the Y-axis direction, and about 16 microns in the vertical direction.

Within the action zone, the percentage of affected (i.e., damaged, altered, or killed) target objects 160 also relies on the shape and the position of the sample 120 core stream. By adjusting the flow rates of the sheath or buffer hydrodynamic focusing flows, the size and position of the sample 120 core stream can be tailored to accommodate the action zone in the horizontal and vertical directions. Eventually, at the desired energy level of the focused energy apparatus 157, flow conditions for the present microfluidic chip 100 can be determined. Thus, the shape of the sample 120 stream can be preferably constrained to around an exemplary 10 microns in width and 5-10 microns in height.

In other embodiments, the action zone as substantially described above, is disposed prior to interrogation, or after the sample fluid 120 leaves the chip 100 for container 188 (see FIGS.

Operation on Sperm Cells

As discussed above, in one exemplary embodiment using sperm cells 160 as the objects 160, the live sperm cells 160 (i.e., bovine sperm cells, with approximately 50-50 X-chromosome and Y-chromosome cells) are introduced into sample input 106, and pass through hydrodynamic focusing steps, to reach the interrogation region 129. In the interrogation region 129, the dye (i.e., Hoechst 33342 dye) is excited by an interrogation beam 148 from a light source 147, such as a laser 147, which generates fluorescence in the cells 160 which is captured by an optical signal detector 154 after passing through an objective lens 153.

Based on characteristics of the fluorescence signal, for example, a difference in reflective properties, the controller 156 can individually identify and distinguish target sperm cells 160 from non-target sperm cells 160. If the sperm cell 160 is a wanted sperm cell (i.e., one of X- or Y-chromosome sperm cell), a determination is made to allow the wanted or non-target sperm cell 160 to pass through the microfluidic channel 164 to collection apparatus 188 unaffected. However, if the sperm cell is an unwanted sperm cell (i.e., the other of X- or Y-chromosome sperm cell), the focused energy apparatus 157 will be employed to act upon the target sperm cell 160 after a pre-determined delay time, to allow for the unwanted/target sperm cell to reach the action zone (which may be in the chamber 129, or between output 112 and collection apparatus.

The present invention allows for jitter in the system of the present invention, in order to have the most effective operation of the focused energy device 157 in the action zone, after the predetermined delay time. Depending on the travelling velocity of the target sperm cell 160, the target sperm cell 160 will be in the action zone for about 2 .ts and the focused energy beam 148 is most effective when aimed at the center of the target sperm cell 160. Thus, it is preferable to limit jitter to within 1 is or less.

As noted above, the target sperm cells 160 may be altered, photodamaged, killed, altered, disabled, or destroyed by either: 1) targeted or "pulse-on-demand" mode, or 2) a "continuous firing" mode, of the focused energy apparatus 157. As noted above, it is preferable to choose a laser wavelength for the focused energy device 157 that minimizes the required flux. For example, matching the laser wavelength to the absorbance of the dye used in the sperm cell staining can improve efficiency and effectiveness. For example, if Hoechst 33342 dye is used for the staining process, a 355 nm laser wavelength for focused energy apparatus 157, is optimal.

In one embodiment, the target sperm cells are killed, or destroyed. In another embodiment, the target sperm cells 160 are sufficiently disabled such that they are no longer capable of performing a defined function. For example, a tail of the target sperm cell 160 may be disabled such that it no longer exhibits progressive motility. Thus, the target, disabled sperm cell 160 will be prevented from fertilizing an egg.

In one embodiment, sophisticated software for the controller 156 can be designed for a high power laser 157 meeting the requirements described above that allows single laser pulses 158 to be fired. Thus, the targeted firing or "pulse-on-demand" mode delivers consistent laser pulses 158 whenever requested by the focused energy apparatus 157. The targeted firing mode is preferably used for samples 120 that contain mostly non-target sperm cells 160, and only a relatively small number of target sperm cells 160 that need to be eliminated. However, with high speed pulse-on-demand systems commercially available, the targeted firing mode can be implemented for samples having other ratios of non-target to target sperm cells.

In an alternative embodiment, when target sperm cells 160 largely outnumber the non-target sperm cells 160, the focused energy apparatus 157 may not be able to generate laser pulses 158 fast enough to act upon (i.e., kill or disable) all of the target sperm cells 160. Thus, the targeted firing mode becomes less effective. In this case, the "continuous firing" mode becomes more favorable.

In the continuous firing mode, as discussed above, the focused energy apparatus 157 is a continuous wave (CW) or quasi-CW, or rapidly pulsed laser 157, used to act on (i.e., kill or disable) every sperm cell 160 passing through a certain location in the microfluidic channel 164 without discriminating between target and non-target sperm cells 160. The focused energy beam 158 is shut off, deflected, or otherwise interrupted for a short period of time to allow non-target sperm cells (i.e., one of X-chromosome or Y-chromosome cells) to pass through unaffected when a group of non-target sperm cells 160 is identified. The group can be any pre-determined number of non-target sperm cells 160. After the non-target sperm cells 160 pass the action zone, the continuous firing mode is re-started.

In both the targeted and continuous firing modes of operation, sperm cells 160 that are too close to each other or that overlap one another in the sample fluid 120 stream are both killed, or both disabled, even if one of the sperm cells 160 is a non-target sperm cell 160 instead of a target sperm cell 160. As used herein, the term "too close" refers to the presence of two or more sperm cells within range of the focused energy beam 158 such that both objects 160 are sufficiently acted upon by the focused energy beam 158 that the desired action occurs in both cells. In addition, sperm cells 160 that are unable to be effectively identified as either a non-target or target sperm cell 160, are killed or disabled by the focused energy beam 158, to ensure overall sample purity for the discriminated product 165. Reasons that the discriminating system of the present invention may be unable to effectively identify a non-target sperm cell 160, may be due to flow issues within the microfluidic channel 164, staining problems, doublets, etc. Because the system of the present invention errs on the side of killing or disabling target sperm cells 160, or any sperm cells 160 that cannot be effectively identified as either target or non-target, more pulses 158 may be used than the total number of actual target sperm cells 160 present in the sample 129.

In one embodiment, as noted above, it is preferable to include a short "recharge/charge time" between laser pulses 158 of the focused energy apparatus 157. First, the spacing between two consecutive sperm cells 160 is not uniform, but instead, follows a Poisson distribution. In the sample fluid flow 120, there is a percentage of sperm cells 160 that are relatively close to each other. To employ the focused energy apparatus 157 at the events that have closer spacing (i.e., shorter elapse time), less focused energy beam 158 "recharge/charge time" would be allowed. Further, if two sperm cells 160 are too close to each other such that their fluorescence signals interfere with each other, and no clear identification of whether the sperm cell 160 is a target or non-target cell, the focused energy apparatus 157 will have to fire multiple laser pulses 158 in a short period of time to kill or disable all of the unidentifiable sperm cells 160 in order to maximize sample purity. Thus, to achieve a higher throughput, generally a shorter average elapsed time between pulses 158 is required.

As noted above, the discriminated sample 120, after being acted upon by the focused energy apparatus 157, is collected in a collection device 188. Thus, in one embodiment, the collected product 165 contains both the non-target sperm cells 160, and the target (i.e., killed, altered, destroyed, disabled) sperm cells 160, still in the same gender ratio as the original sample 120. The collection in a single container 188 does not affect an overall sample 120 quality. Thus, in one embodiment, the final product 165 that is used for eventual fertilization includes both the non-target and target sperm cells 160. Alternatively, subsequent product 165 separation techniques (i.e., flow cytometry, electrostatic plates, holographic optical trapping etc.) may be used to, for example, separate the sperm cells 160 of the product 165 into live or dead/disabled sperm cells 160, or centrifugation may be used for removing unwanted debris such as the remains of the killed or disabled target sperm cells 160.

In one embodiment, the microfluidic chip system of the present invention is used in concert with a separation or isolation mechanism, such as the exemplary piezoelectric actuator assembly device described in pending U.S. patent application Ser. No. 13/943,322, filed Jul. 16, 2013, or an optical trapping system as described in U.S. Pat. Nos. 7,241,988, 7,402,131, 7,482,577, 7,545,491, 7,699,767, 8,158,927 and 8,653,442, for example, the contents of all of which are herein incorporated by reference in their entirety.

In one embodiment, as shown in FIGS. 6B-C, the main channel 164 is shortened past the action chamber 129, such that the discriminated objects 160 leave the output channel 141 and output 112 in droplet 187 form, before falling toward a collection apparatus 188. The operation of the focused energy apparatus 157 is the same, except that the objects 160 are acted upon as they leave the exit of output channel 112 (see FIG. 6B), or as the disconnected droplets 187 fall (see FIG. 6C), and before they enter the collection apparatus 188.

Post-Collection of the Discriminated Product

In one embodiment, the discriminated objects 160 are collected in a container 188 having 20% Tris (note: commercially available, such as sold by Chata Biosystems), which is disposed below the chip 100 output 112. In one embodiment, the contents of the container 188 are circulated at predetermined intervals, to ensure mixing of the product 165 therein. In one embodiment, when the container 188 reaches a predetermined volume (i.e., 18 ml), the container 188 may be replaced with a new container 188.

In one embodiment, antibiotics are added to a filled container 188 (i.e., 0.5 ml CSS antibiotics to 30 ml of product 165), the time recorded, and a plurality of containers 188 with product 165 are collected in a large container and cooled. In one example, three containers 188 with antibiotic-containing product 165, at a time, are disposed in a 400 ml plastic container and placed in a cold room.

In one embodiment, after a predetermined amount of time in cooling (i.e., 2 hours), Tris B extender (14% glycerol Tris) is added in two aliquots, a predetermined time apart (i.e., 15 minutes), to each tube. After the last sample 120 has cooled for a predetermined time (i.e., 2 hours), and B extender is added, the samples 120 are centrifuged for 20 minutes at 850×G in a refrigerated centrifuge at 5° C. Supernatant is aspirated from each tube, leaving −0.2 ml with the pellet. All the pellets are combined into a single, pre-weighed container (i.e., tube), and a concentration of combined pellet using commercially available counting protocols (i.e., SpermVision) is determined, and the final concentration calculated to 11.35×106 cells/ml. The final volume is adjusted with a complete Tris A+B+CSS antibiotics extender (i.e., 50:50 ratio of 20% egg yolk Tris+14% glycerol Tris).

In the exemplary embodiment of sperm cells 160, the printed semen straws are filled and sealed, and the straws frozen using liquid nitrogen vapor.

In one embodiment, quality control measures post-freeze include bacterial contamination steps, where a frozen straw is thawed in a water bath, and the thawed straw is wiped with alcohol to disinfect it. The straw contents are plated onto blood agar plate (5% sheep's blood), and incubated at 37° C. for 24 hours to determine the bacterial content.

In one embodiment, quality control measures for progressive motility include thawing one frozen straw in a water bath, and expelling the straw contents into a small tube placed in the tube warming stage. Commercial methods such as Motility Analysis or SpermVision are used to determine the number of motile cells per straw.

In one embodiment, quality control measures for sample purity include thawing one frozen straw in a water bath, and isolating the live cells by processing them through glass wool. Then FISH analysis is performed on the live cell population to determine the sex chromosome ratio.

Multiple Systems

In one embodiment, a plurality of microfluidic chips 100, optical interrogation apparatuses and focused energy apparatuses, are set up in parallel to increase throughput.

Figure 18:
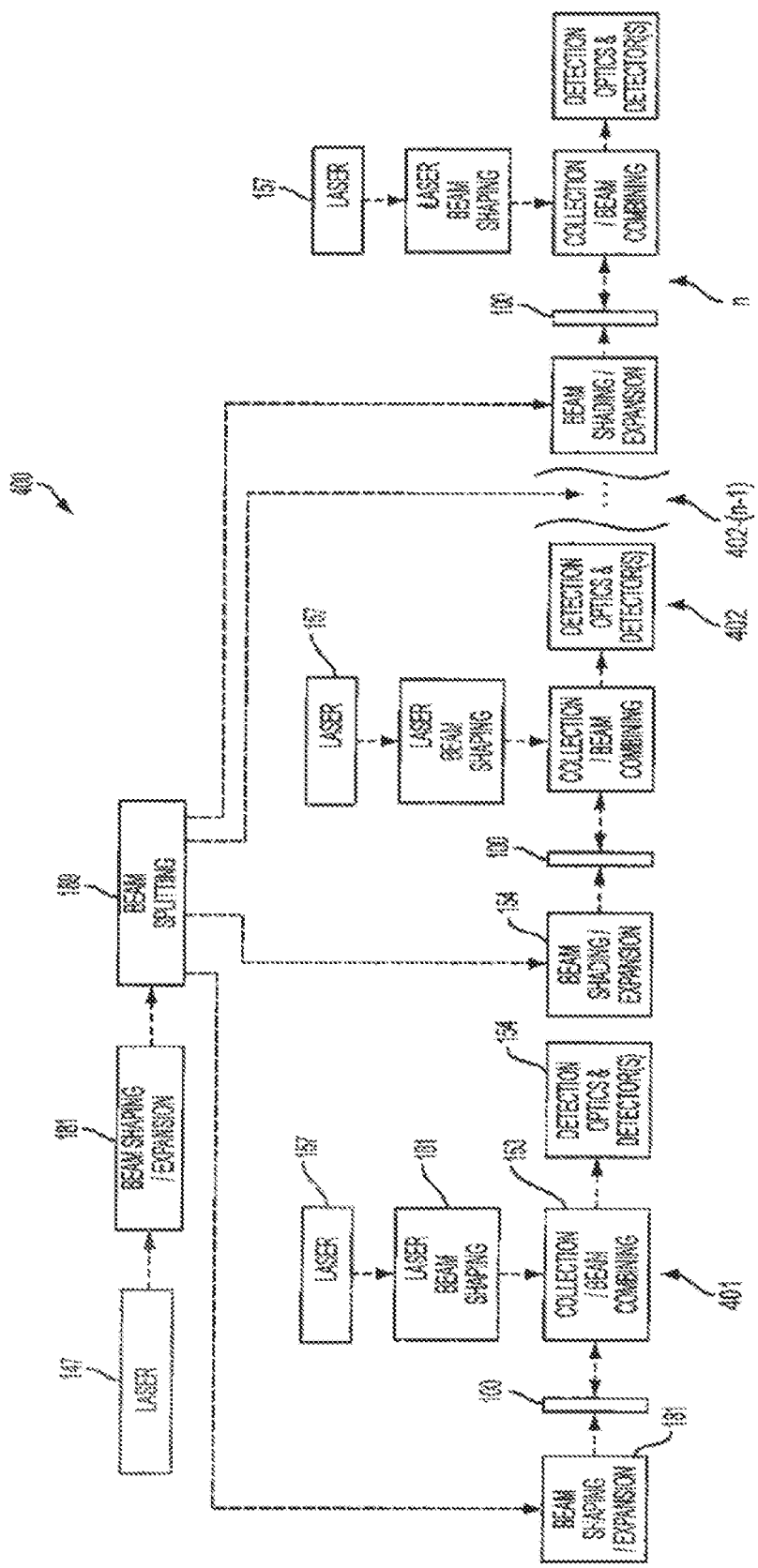
FIG. 18 shows a schematic view of multiple microfluidic chip systems disposed in parallel, using a single interrogation apparatus, according to one embodiment consistent with the present invention.

Referring now to FIG. 18, in one embodiment, a multiple systems layout 400 with, for example, "n" systems 401, 402, etc., each equipped with a focused energy apparatus 157 is illustrated. In one embodiment, the multiple systems layout 400 includes a single interrogation apparatus 147, and a single interrogation beam 148 which is configured to provide a fluorescence excitation energy for the detection of objects 160—for example, sperm DNA content.

In one embodiment, the multiple systems layout 400 further includes beam shaping optics 181, with a series of beam splitters 189, each beam splitter providing a 50/50 split of the incoming power. This results in nearly equal power beams 158 for each of the multiple systems 401, 402, etc.

External Devices

Separation Apparatus

In one embodiment, after the focused energy apparatus 157 acts on the objects 160 flowing through the microfluidic chip 100, instead of flowing into output channel 141, a separation mechanism (i.e., piezoelectric actuator assembly device (external or internal), optical trapping assembly, electrostatic plates, or other separation mechanism well known to one of ordinary skill in the art, may separate the targeted and non-targeted objects 160. (See U.S. patent application Ser. No. 13/943,322, filed Jul. 16, 2013, or U.S. Pat. Nos. 7,241,988, 7,402,131, 7,482,577, 7,545,491, 7,699,767, 8,158,927 and 8,653,442, for example, the contents of all of which are herein incorporated by reference in their entirety).

Thus, in one exemplary embodiment, targeted objects 160 that have been damaged, killed, disabled, destroyed or altered by the focused energy apparatus 157, can be separated from non-targeted objects 160, with the separation mechanism separating the targeted objects into one of the output channels 140-142, and the non-targeted objects 160 into another of the output channels 140-142.

In another embodiment, the targeted objects are separated using a separation mechanism after exiting from output 112, by use of electrostatic plates—well known in the art—for example.

In yet another embodiment, the focused energy apparatus 157 acts on the objects 160 as they exit or drop from output 112, and the separation mechanism also separates the targeted objects 160 from the non-target objects 160 thereafter, or from product 165.

Pumping Mechanisms

Figure 19:
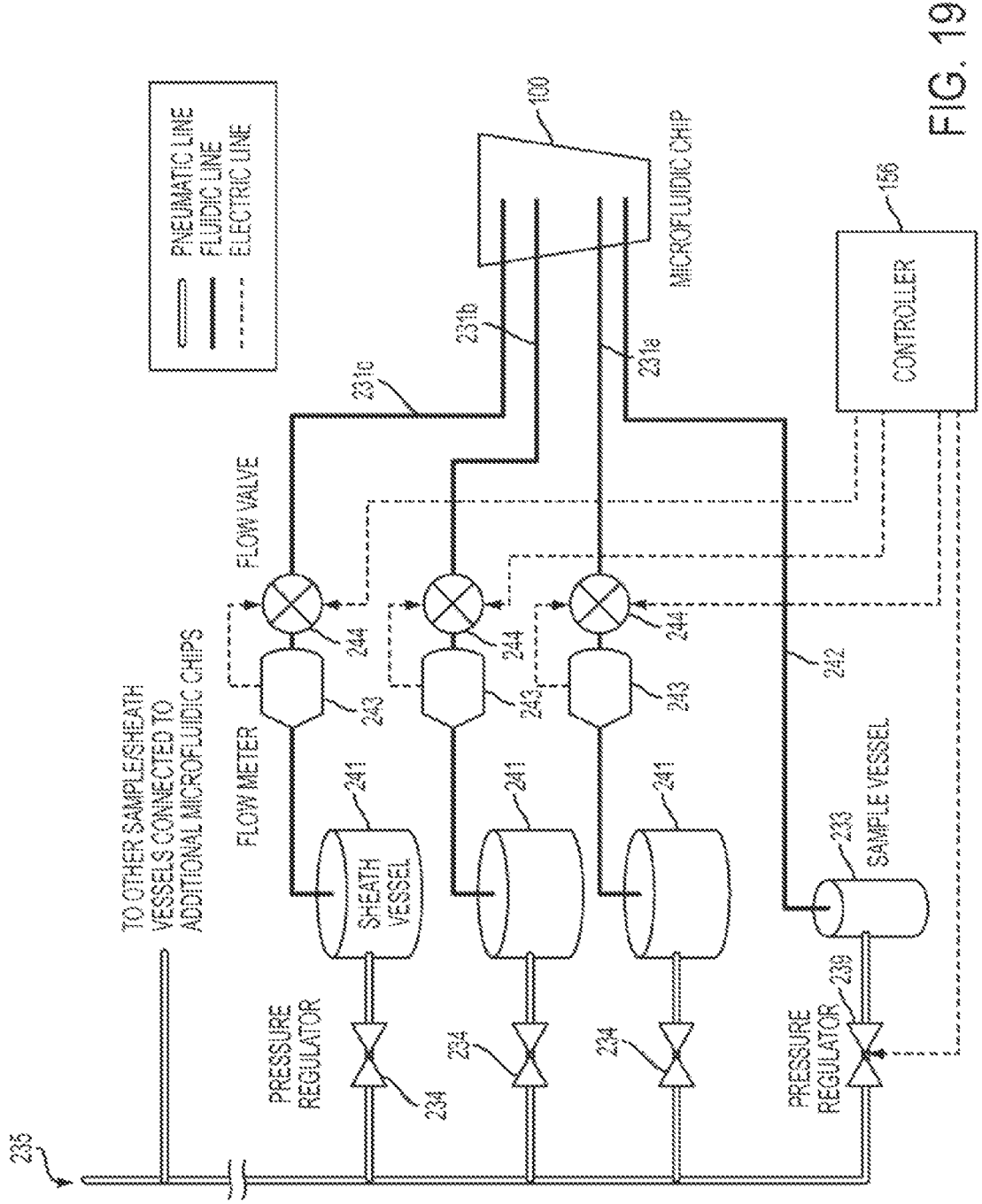
FIG. 19 shows a schematic view of the flow control network of the microfluidic chip system, with external individual reservoirs for sample and sheath or buffer fluids, according to one embodiment consistent with the present invention.

As shown in FIGS. 19-21, in one embodiment, a pumping mechanism includes a system having a pressurized gas 235 which provides pressure for pumping sample fluid mixture 120 from reservoir 233 (or sample tube 233), via tubing 242, into sample input 106 of the microfluidic chip 100.

A central reservoir 240 (see FIGS. 20-21), or individual reservoirs 241 (see FIG. 19), contain sheath or buffer fluids 163, and are connected to each sheath or buffer input 107, 108, 172 of the microfluidic chip 100 via tubing, in order to introduce sheath or buffer fluids 163 therein. In one embodiment, the reservoirs are collapsible containers 237 (see FIGS. 20-21), which are disposed in pressurized vessels 240, and the pressurized gas 235 pushes sheath or buffer fluids 163 to the microfluidic chip 100. In one embodiment, the pressurized vessel 240 pushes sheath or buffer fluids 163 to a manifold 238 (see FIG. 21) having a plurality of different outputs, such that the sheath or buffer fluids 163 are delivered via tubing 231a, 231b, or 231c to the sheath or buffer inputs 107, 108, or 172 respectively, of the chip 100. Although a three input sheath or buffer fluid arrangement is shown (i.e., FIG. 1D), one of ordinary skill in the art would know that less or more tubing delivering sheath or buffer fluids to the microfluidic chip 100 is possible. In addition, although the tubing is shown as entering microfluidic chip 100 in FIGS. 18-21, the disposition of the tubing with respect to the inputs on the chip 100 are not shown in exact order. Further, one of ordinary skill in the art would know that the tubing enters the chip 100 via chip holder 200 (discussed below).

In one embodiment, each individual reservoir 241, or central reservoir 240, includes a pressure regulator 234 which regulates the pressure of the gas 235 within the reservoir 241, 240 (see FIGS. 19-21). In one embodiment, a pressure regulator 239 regulates the pressure of gas 235 within the sample vessel 233. Flow meters 243 and flow valves 244 control the sheath or buffer fluids 163 pumped via tubing 231a, 231b, or 231c, respectively, into the sheath or buffer inputs 107, 108, or 172, respectively (via holder 200). Thus, tubing 230, 231a, 231b, 231c, is used in the initial loading of the sheath or buffer fluids 120 into the chip 100, and may be used throughout chip 100 operation to load sample fluid 120 into sample input 106, or sheath or buffer inputs 107, 108 (and 172).

In one embodiment, the flow meters 243 are used to provide the feedback to flow valves 244 (see FIGS. 19-20) placed in the sheath flow routes to achieve a stable flow with constant flow rate in the microfluidic channels. With the precise control of the flow, the overall flow rate variation is less than 1% of set flow rate, and the travelling speed to target objects 160 varies less than 1% during the detection and between interrogation/detection spot and action spot.

In one embodiment, sheath or buffer fluid 163 is pumped through a vacuum chamber (not shown) that is disposed in between the pressure canister and the manifold, so as to remove dissolved gas in the sheath or buffer fluid. Inside the vacuum chamber, a segment of gas permeable tubing is disposed between the input port and output port. While the sheath or buffer fluid travels inside the vacuum chamber via the gas permeable tubing, the dissolved gas passes through the wall of the tubing, while the liquid remains inside the tubing. The applied vacuum helps gas permeate through the tubing wall. In one embodiment, the gas permeable tubing is made of a hydrophobic porous material, for example expanded polytetrafluoroethylene (EPTFE), which has a high water entry pressure for liquid but is permeable for gas.

Computer Control

In one embodiment, the user interface of the computer system 156 includes a computer screen which displays the objects 160 in a field of view acquired by a CCD camera 182 over the microfluidic chip 100.

In one embodiment, the computer 156 or a controller 156 controls any external devices such as pumps (i.e., pumping mechanisms of FIGS. 19-20), if used, to pump any sample fluids 120, sheath or buffer fluids 163 into the microfluidic chip 100, and also controls any heating devices which set the temperature of the fluids 120, 163 being inputted into the microfluidic chip 100.

In accordance with an illustrative embodiment, any of the operations, steps, control options, etc. may be implemented by instructions that are stored on a computer-readable medium such as a computer memory, database, etc. Upon execution of the instructions stored on the computer-readable medium, the instructions can cause a computing device 156 to perform any of the operations, steps, control options, etc. described herein.

The operations described in this specification may be implemented as operations performed by a data processing apparatus or processing circuit on data stored on one or more computer-readable storage devices or received from other sources. A computer program (also known as a program, software, software application, script, or code) can be written in any form of programming language, including compiled or interpreted languages, declarative or procedural languages, and it can be deployed in any form, including as a stand-alone program or as a module, object, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network. Processing circuits suitable for the execution of a computer program include, by way of example, both general and special purpose microprocessors, and any one or more processors of any kind of digital computer.

Microfluidic Chip Holder

In one embodiment, the microfluidic chip 100 is loaded on a chip holder 200 (see FIGS. 22A-23B). The chip holder 200 is mounted to a translation stage (not shown) to allow positioning of the holder 200 with respect to the interrogation apparatus and focused energy apparatus. The microfluidic chip holder 200 is configured to hold the microfluidic chip 100 in a position such that the light beam 148 from the interrogation apparatus may intercept the objects 160 in the above described manner, at opening 150, and the focused energy apparatus 157 may act upon the objects 160.

The mechanisms for attachment of the chip 100 to the holder 200 are described below along with their method of operation, but one of ordinary skill in the art would know that these devices may be of any configuration to accommodate the microfluidic chip 100, as long as the objectives of the present invention are met.

As illustrated in FIGS. 22A-23B, in one embodiment, a microfluidic chip holder 200 is made of a suitable material, such as aluminum alloy, or other suitable metallic/polymer material, and includes main plate 201 and fitting plate 202. The main plate 201 and fitting plate 202 may be of any suitable shape, but their configuration depends on the layout of the chip 100 and the requirements for access thereto.

In one embodiment, the main plate 201 has a substantial L-shape, but the shape of the holder 200 depends on the layout of the chip 100 (see FIGS. 22A-23B). One leg of the L-shaped main plate 201 includes a plurality of slots which are configured to receive mounting screws 219, which are used to mount the holder 200 on the translation stage. Any number of slots of any suitable shape and size, may be included in the main plate 201. In one embodiment, four screws 219 are used to mount the holder 200 on the translation stage and adjust the position of the holder 200. However, one of ordinary skill in the art would know that any number of any size slots and mounting screws may be used.

In one embodiment, a switch valve 220 is attached to the main plate 201 above the mounting screws 219 on the one leg of the L-shaped main plate 201 (see FIGS. 22A-23B). In addition, in the other leg of the L-shaped main plate 201, a pair of linear actuators, such as pneumatic cylinder actuators 207A and 207B, are disposed on the same side of the main plate 201 as the switch valve 220 (see FIGS. 22A-23B).

In one embodiment, a fitting plate 202 is attached to the main plate 201, on the other side and along the other leg of the L-shaped main plate 201 (see FIGS. 22A-23B). The fitting plate 202 includes a plurality of apertures which accommodate a plurality of fittings 204-206 (see FIGS. 22A-22B, for example) configured to receive and engage with external tubing (see FIGS. 19-23B) for communicating fluids/samples to the microfluidic chip 100. In one embodiment, the fitting plate 202 includes three fittings 204-206, which are used to align with the sheath or buffer inputs 107, 108, and sample input 106, respectively (see FIGS. 1B and 22A-22B). In another embodiment, four fittings 204-206 and 216, are used to align with the sheath or buffer inputs 107, 108, sample input 106, and sheath or buffer input 172, respectively (see FIGS. 1A and 23A-23B). However, one of ordinary skill in the art would know that the fittings would be arranged in any way by number and position, so as to align with the number of inputs in the microfluidic chip 100 and allow transmission of fluids from one or more reservoirs via tubing (see FIGS. 19-21).

In one embodiment, a pair of slot washers 203A, 203B affix the fitting plate 202 and pneumatic cylinder actuators 207A, 207B to the main plate 201 (see FIGS. 22A-23B). Thus, the fitting plate 202 is easily removed from the main plate 201 without disassembling the switch valve 220 and pneumatic cylinder actuators 207A, 207B from the main plate 202.

In one embodiment, the pneumatic cylinder actuators 207A, 207B each include a piston (not shown) having a piston rod coupled thereto and extendable and retractable relative to the cylindrical body portion. In one embodiment, air is supplied through port 209 into the switch valve 208, and exits through ports 210, 211 to ports 212, 213, respectively, in pneumatic cylinder actuator 207A. The air is further supplied from ports 214A, 214B in pneumatic cylinder actuator 207A, to ports 215A, 215B, respectively, in pneumatic cylinder actuator 208A.

The toggle switch 220 of switch valve 208 opens and closes, to allow or prevent, respectively, the air from the air supply entering through port 209 and to pneumatic cylinder actuators 207A, 207B. When the air is provided to the pneumatic cylinder actuators 207A, 207B, the piston rods of the pneumatic cylinder actuators 207A, 207B are extended outwardly to an open position (not illustrated), and fitting plate 202 is pushed outwardly away from the microfluidic chip 100 to an open position to allow a user to load (or unload) the microfluidic chip 100 (see FIGS. 22A-23B). When the air supply is closed, the piston rods of the pneumatic cylinder actuators 207A, 207B are retracted inwardly to a closed position (as illustrated in FIGS. 22A-23B), and the fitting plate 202 is drawn towards the chip 100 and pressed against the chip 100 forming a liquid seal between the chip 100 and the connections to the tubing for the sheath or buffer and sample fluids.

In one embodiment, when the microfluidic chip 100 is in the closed position, O-rings, which are disposed on the surface of the fitting plate 202, between the fitting plate 202 and the chip 110, form a substantially leak-free seal to protect the microfluidic chip 100 from damage. However, one of ordinary skill in the art would know that any number and configuration of O-rings or gaskets may be used.

In one embodiment, the holder 200 is positioned such that the chip 100 is at a sufficient height to accommodate at least one collection vessel 188 disposed underneath the chip 100. In another embodiment, collection vessels are disposed between each output 111-113.

In another embodiment, the present invention discloses a method of inseminating an animal comprising flowing a stream of a population of sperm cells through a channel, differentiating the sperm cells into at least two subpopulations with one subpopulation comprising X-chromosome containing sperm cells and another subpopulation comprising Y-chromosome containing sperm cells, selecting a desired subpopulation, ablating an undesired subpopulation, and collecting both the desired subpopulation and the ablated undesired subpopulation together, wherein the collected population of sperm cells is used to fertilize an egg. Insemination is the deliberate introduction of sperm into a female animal for the purpose of impregnating or fertilizing the female for sexual reproduction. Insemination is inclusive of introduction of a fertilized egg into a female animal. X chromosome and Y chromosome are both sex chromosome, and generally, two X chromosomes are present in female cells and generally only one X chromosome and one Y chromosome are present in male cells. Fertilization is defined as the fusion of male and female gametes to form a zygote, a fertilized egg. Specifically, a sperm cell unites with an egg. Differentiating sperm cells includes identifying a physical or a genetic characteristic of a sperm cell including, but not limited to, whether a sperm cell has an X-chromosome or a Y-chromosome. Selecting a desired subpopulation includes targeting a subpopulation of cells for a certain action, for instance, ablating the subpopulation of cells while not ablating a different subpopulation of cells. Ablating an undesired subpopulation is defined as rendering sperm cells deficient in fertilizing an egg. It could be further defined as rendering sperm cells incapable of fertilizing an egg. Collecting subpopulations of sperm cells includes gathering both the selected and the unselected subpopulations together, usually in a container, a tube or a straw. It could be further defined as the stream of population of sperm cells are not physically subdivided prior to and subsequent to ablation of a subpopulation of sperm cells and that both subpopulations exit together and are gathered.

In a further embodiment, the present invention includes inserting the collected population of sperm cells into the mammal (human or animal) to fertilize an egg. Given that sperm cells outside the body are generally subject to conditions that are unfavorable for their survivability, fertilization should occur as soon as possible following collection. In some embodiments, the insertion occurs within forty-eight hours following the collection.

In a further embodiment, the present invention includes fertilizing the egg in vitro with the collected population of sperm cells to create a fertilized egg, and implanting the fertilized egg within the animal wherein the implantation occurs within forty-eight hours following fertilization. In vitro fertilization is a process of creating embryos from oocytes (unfertilized egg cells) by fertilizing them with semen outside the uterus. Implantation of the fertilized egg within the mammal (human or animal) include, at least, the placement of the fertilized egg in any part of the female mammal (human or animal), such as the uterus to allow for the development of the fertilized egg into an embryo according to the genetics of the fertilized egg.

In a further embodiment, the present invention includes obtaining genetic information of the sperm cells or the fertilized egg prior to implantation. In some embodiments, at least one, alternatively at least two cells of the fertilized egg for analysis. In other embodiments, a portion of a DNA molecule or an RNA molecule of the fertilized egg is sequenced. In some embodiments, yj DNA or RNA sequencing occurs within forty-eight hours following removal of at least one, alternatively at least two cells of the fertilized egg for analysis. Alternatively, the DNA or RNA sequencing occurs within twenty-four hours following removal of at least one, alternatively at least two cells of the fertilized egg for analysis. Obtaining genetic information, i.e., DNA or RNA sequencing, of the sperm cells or the fertilized eggs includes assessing the genetic profile or a gene or a set of genes to determine the quality of the cells and/or the phenotypic trait(s) of the grown animal. Alternatively, probes, including oligonucleotides could be used to ascertain the genetic sequence or profile of certain genes. DNA or RNA arrays could be used to assess the genetic profile of a cell. All known molecular biological and cellular techniques could be employed to assess the characteristics and the identities of the cells and their likely phenotypic outcome as an animal. Such analyses typically occur within a short period such as within forty-eight hours, alternatively within twenty-four hours to lessen any damage to lessen any damage to the sperm cells or the fertilized eggs.

In a further embodiment, implanting the fertilized egg within the mammal (human or animal) occurs within forty-eight hours following obtaining the genetic information of the fertilized egg. The sooner a fertilized egg is implanted within a mammal (human or animal), the better to ensure survivability.

With respect to flowing the stream of the population of sperm cells through the channel, a further embodiment includes orienting the sperm cells in the population in a particular position with respect to the channel, aligning the sperm cells wherein the sperm cells are flowing singularly through the channel, and exiting all the sperm cells through an output portion of the channel. With respect to orienting the sperm cells and aligning the sperm cells, some embodiments include compressing the stream by sheath fluid flowing along at least one side of the stream, and wherein the compressing further comprises intersecting at a substantially 90 degree vertical plane by the sheath fluid from above the stream. In other embodiments, the sheath fluid is in laminar flow with the stream of the population of sperm cells during the differentiating and the ablating steps. In an alternative embodiment, orienting the sperm cells and aligning the sperm cells includes compressing the sperm cells by an inertial force directed by a designed structure of the channel. Orienting includes placing the cell in a proper three dimensional space within the channel to allow for proper determination of characteristics of the cells. Aligning includes placing the cells in proper order within the channel, and in most cases, the proper order is cells in a single file line with consistent orientation. Exiting all the sperm cells through an output portion of the channel includes that the selected and unselected sperms are not separated from each other or their path diverged to a separate path or channel during collection.

Figure 27:
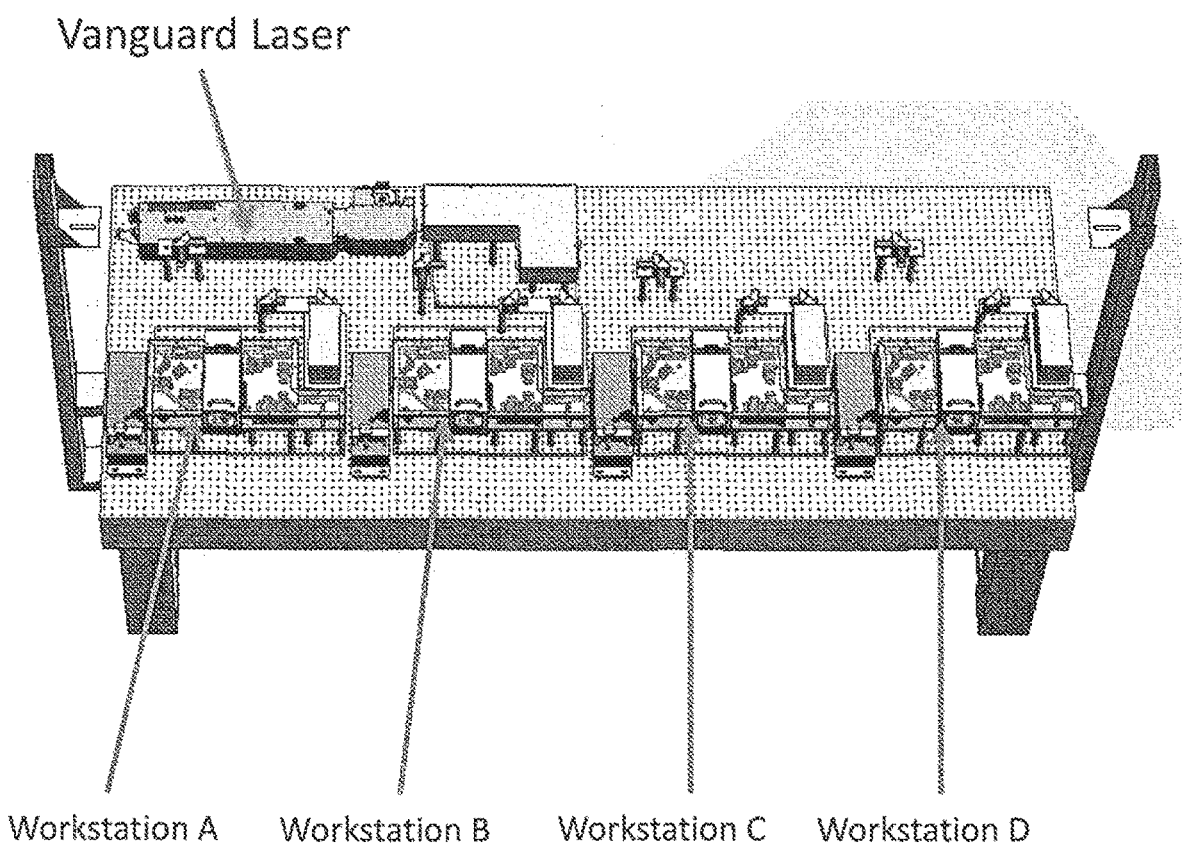
FIG. 27 shows a multiple station setup to analyze cells with a vanguard laser.
Figure 28:
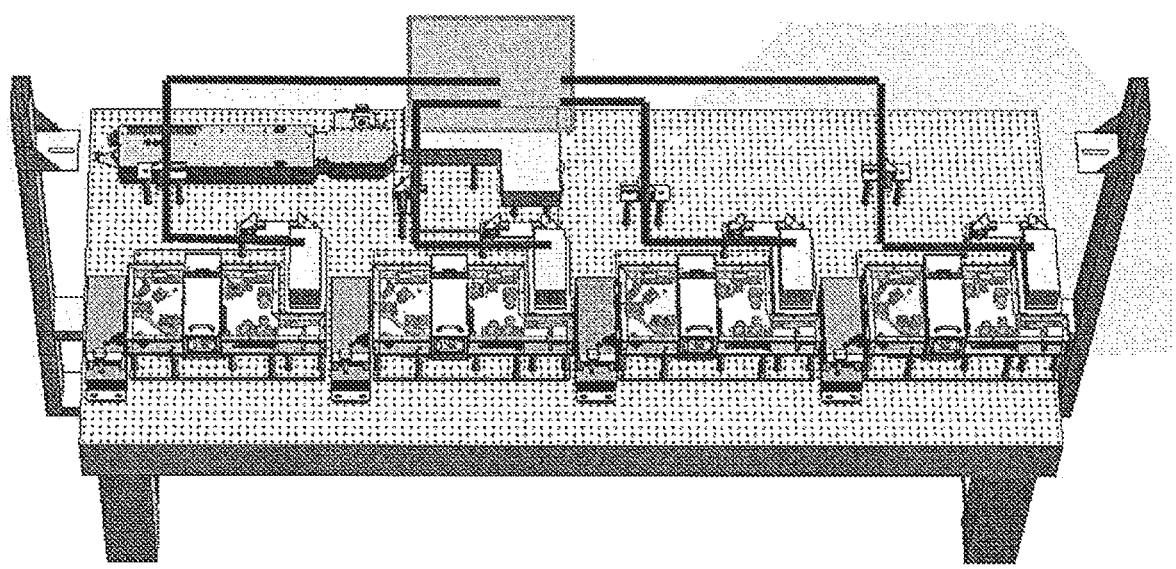
FIG. 28 shows beam splitting occurring for multiple stations.

In another embodiment, differentiating the sperm cells into two subpopulations of X-chromosome containing sperm cells and Y-chromosome containing sperm cells includes illuminating the sperm cells with a beam of light, and detecting a difference between the two subpopulations of sperm cells. In a further embodiment, the beam of light is from a detection laser. FIG. 27 shows a multiple station setup to analyze cells with a vanguard laser. In another embodiment, the beam from the laser is split into multiple beams, and each beam of the multiple beams is configured to illuminate a different sperm cell. In another embodiment, the beam from the laser is not split into multiple beams and the beam illuminates one sperm cell at a time. FIG. 28 shows beam splitting occurring for multiple stations. The beam from the laser is emitted as a continuous wave, or it is emitted in pulses. In an alternative embodiment, the beam of light is from an LED light source.

Figure 24:
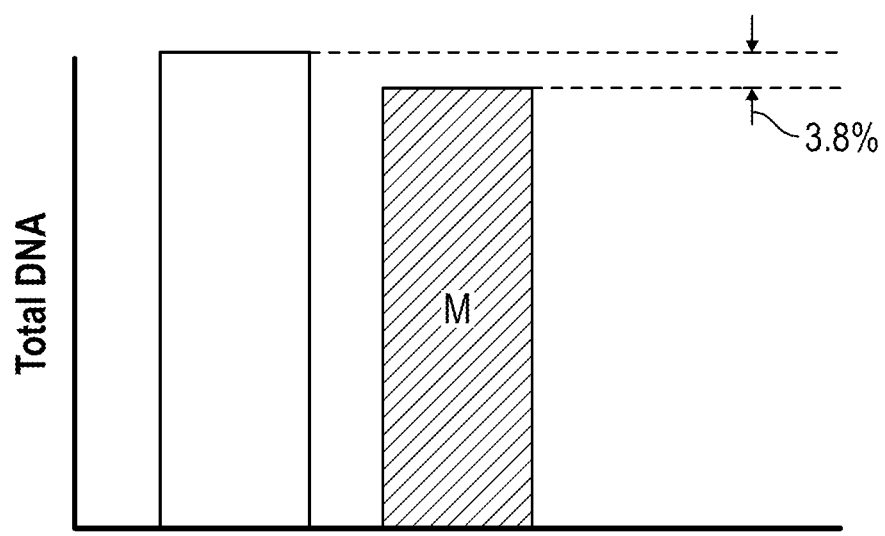
FIG. 24 shows that total DNA comparison between female sperm cell and male sperm cell.
Figure 25:
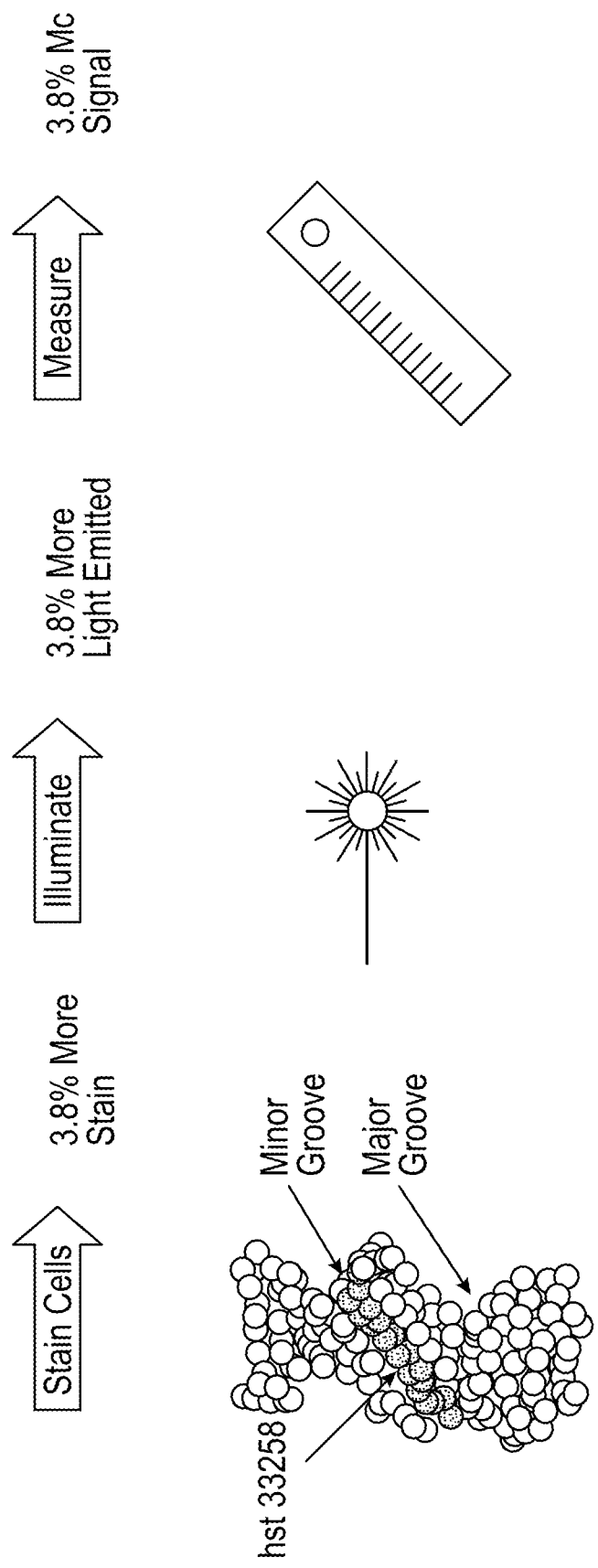
FIG. 25 shows staining of DNA in cells to determine the intensity of emitted light which correlates with the amount of DNA in a cells, wherein 3.8% more light emitted correlates to 3.8% more DNA in female sperm cells.
Figure 29:
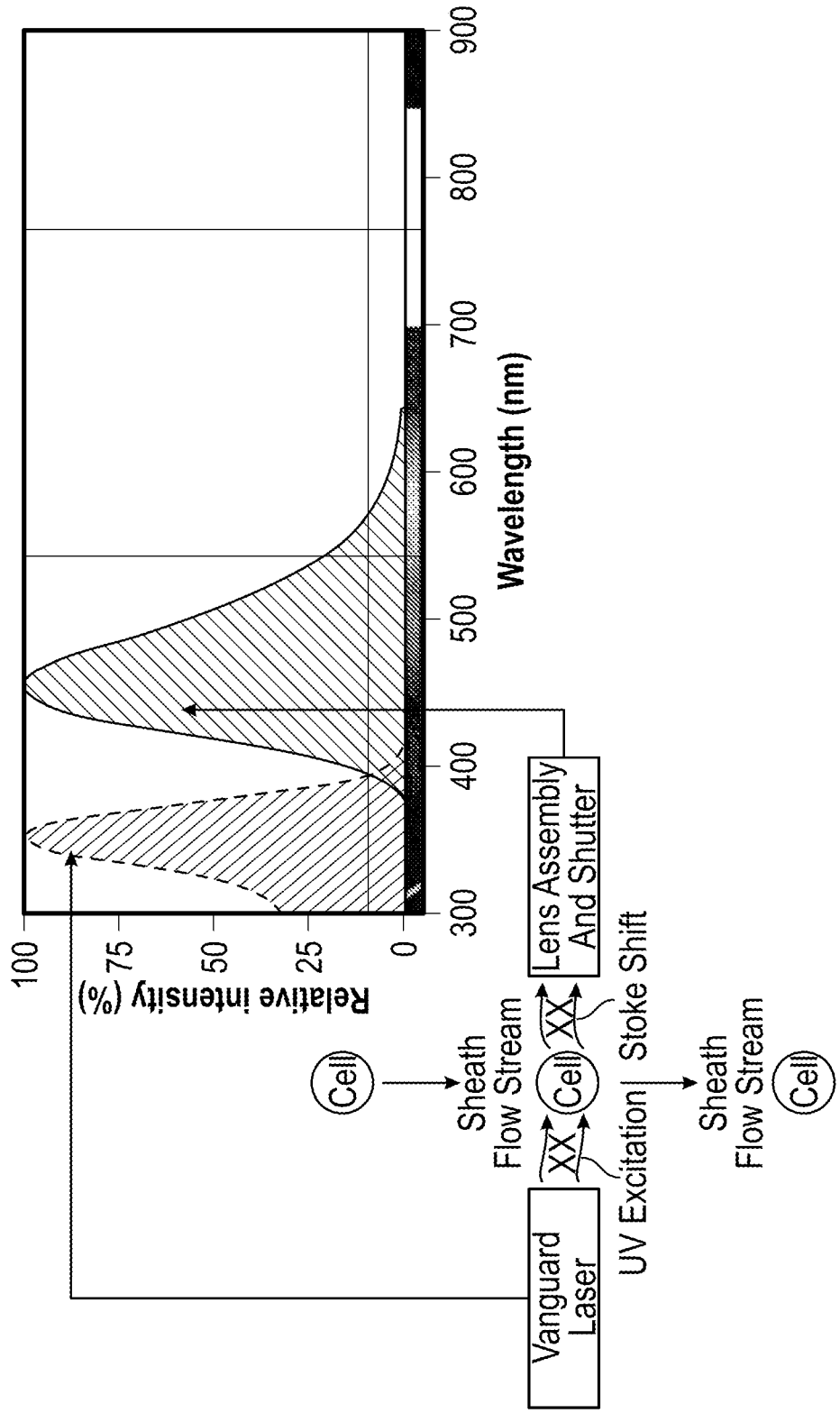
FIG. 29 shows that Stoke shift and optical filter creates peak at 450 nm wavelength—therefore setting our detection wavelength.

In another embodiment, the difference comprises how the sperm cells reflect, refract, diffract, absorb, and/or emit the light. In some instances, a molecule of the sperm cell or a molecule associated with the sperm cell is excited by the beam and the molecule emits a second beam in a Stoke shift. FIG. 29 shows that the Stoke shift creates peak at 450 nm wavelength therefore creating the detection wavelength. The difference reflects a difference in DNA concentration per cell. As seen in FIG. 24, the difference between the subpopulations is at least about 3.8% difference in DNA content. The approximate 3.8% difference reflects the difference sperm cells with the X-chromosome compared with sperm cells with the Y-chromosome. For bovines, female sperm cell has the X-chromosome and 29 autosomes and male sperm cell has the Y-chromosome and 29 autosomes. FIG. 25 shows staining of DNA in cells to determine the intensity of emitted light which correlates with the amount of DNA in a cells, wherein 3.8% more light emitted correlates to 3.8% more DNA in female sperm cells.

In another embodiment, selecting the desired subpopulation of particles includes gating each subpopulation based on a physical difference for each subpopulation, and identifying the desired subpopulation. Gating each subpopulation and identifying the desired subpopulation includes correlating a graphic representation for each subpopulation and choosing or marking the desired subpopulation. As the cells travel through the channel, they are graphically captured and their particular characteristic(s) are plotted on a graph. With each cell plotted on a graph, a gating of any particular population is possible wherein a particular subpopulation is selected or designated for certain action, such as laser ablation rendering certain sperm cells incapable of fertilizing an egg.

Figure 30A:
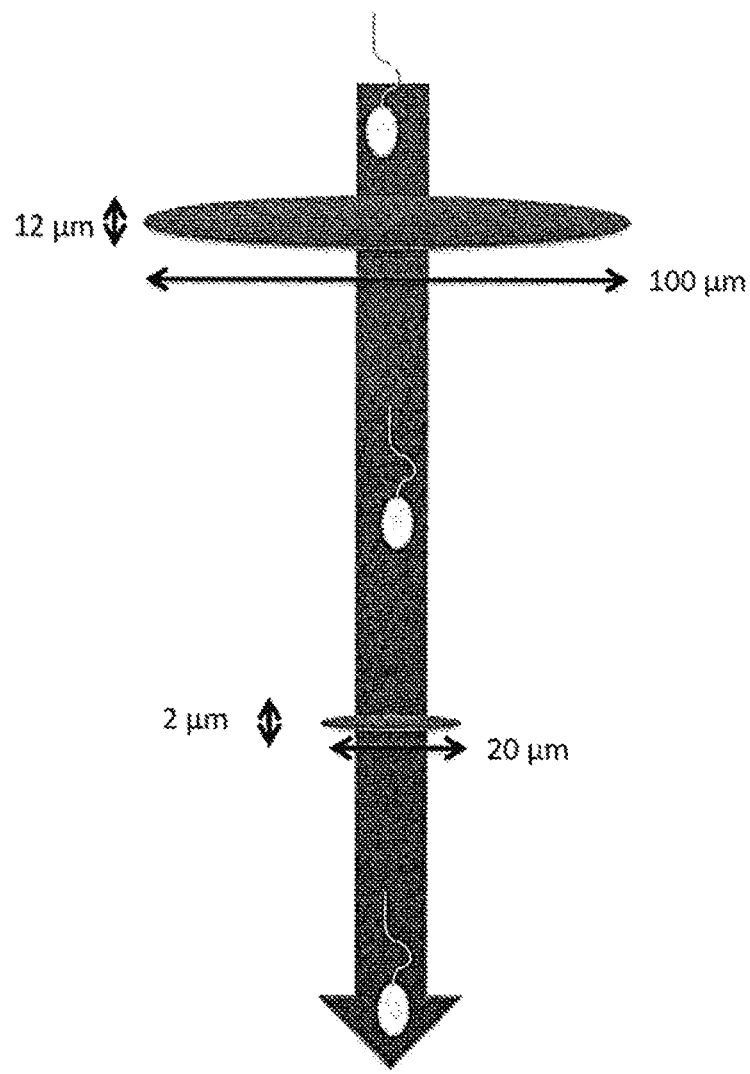
FIG. 30A shows the knife blade shape, which requires tight focusing of cell stream.
Figure 30B:
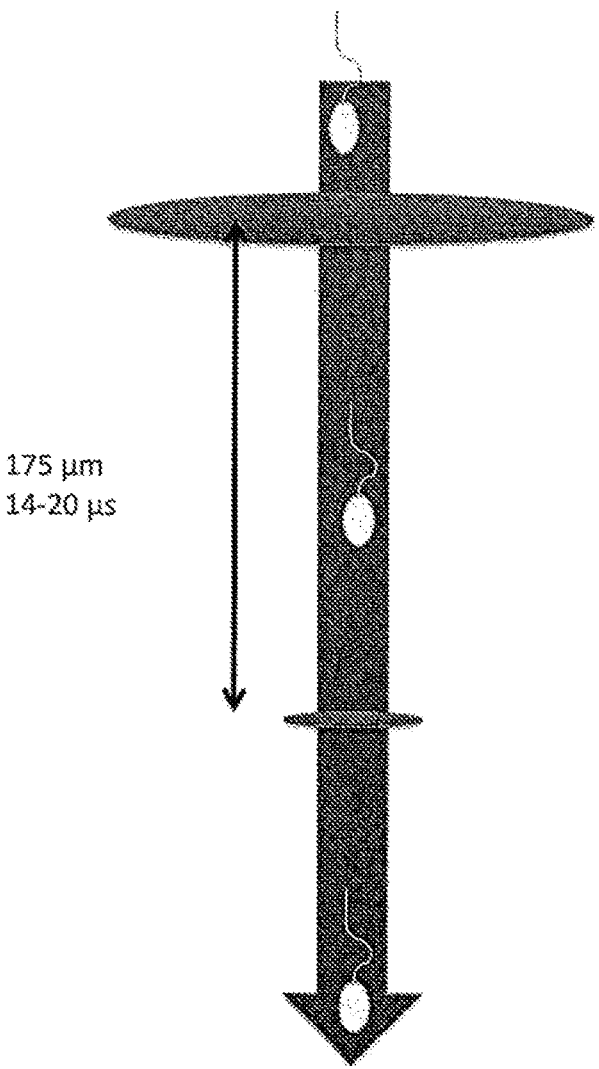
FIG. 30B shows that a kill pulse is triggered based on a timer is when a cell is detected

In another embodiment, the ablating the undesired subpopulation further includes damaging or killing the undesired subpopulation of sperm cells with a second beam of light in an area of the channel, wherein a damaged or killed sperm cell is rendered unable to fertilize an egg. In some embodiments, the second beam of light is from a laser. In a further embodiment, the laser is configured to provide a pulse of beam. In yet another embodiment, the laser is configured to recharge to damage or kill the next sperm cell that enters the area of the channel. As seen in FIGS. 30A and 30B in some embodiments, the beam of light is tightly focused with a blade-shape configured to cut across approximately 2 microns in length of the channel to damage or kill the cell. As seen in FIG. 30B, there is an initial detection of the cell, which triggers a pulse laser based on a timer, and knowing the distance of travel (e.g., 175 micron), the pulse laser damages or kills the cell. In other embodiments, the damaging or killing is coordinated with the travel time of the sperm cells and wherein the sperm cells are travelling at a known velocity. The damaging or killing is coordinated so that the laser hits any particular cell as it travels through the channel. The coordination is timed so that only certain cells are hit with laser beam.

In another embodiment, the animal is a cow or a heifer. A heifer is a young female cow that has not borne a calf. A cow is one that has previously borne a calf. In a further embodiment, the success rate for insemination of the heifer is at least about 60% on average. In an alternative embodiment, the success rate for insemination of the cow is at least about 37% on average. The success rate for insemination of the heifer is better compared with insemination comprising a sexing process that comprises a physical separation of selected sperm cells from unselected sperm cells. Table 2 depicts conception rates (CR) of cattle herds that have received different kinds of insemination technology: sexing technology of the present invention (IntelliGen Sexed Technology), conventional insemination without sexing, and competitors' sexing technology. Different types of heifers (Holstein and Jersey) were inseminated. Over 6000 recorded insemination were analyzed. IntelliGen Sexed Technology achieved 63.8% conception rate for Holstein heifers and 61.9% conception rate for Jersey heifers. For Holstein (HO) heifers, the CR (61.9%) of insemination using IntelliGen Sexed Technology is comparable to the CR (64.6%) for heifer's that received insemination of unsexed sperms (conventional) and much better to the CR (54.7%) of insemination from competitors' sexing technology, suggesting that IntelliGen Sexed Technology is less detrimental compared with competitors' sexing processes. Competitors' sexing processes comprise a physical separation of selected sperm cells from unselected sperm cells. In contrast, IntelliGen Sexed Technology does not require physical separation. Both selected and unselected sperm cells are collected together—only that the undesired subpopulation of sperm cells has been rendered incapable of fertilization. For Jersey (JE) heifers, the CR (61.9%) of insemination from IntelliGen Sexed Technology was surprisingly much better compared with the CR (38%) of conventional insemination as well as the CR (54.7%) of insemination from competitors' sexing technology. Table 3 depicts a comparison of three types of insemination of cows are analyzed with respect to CR: IntelliGen Sexed Technology (42.6% for HO; 37.5% for JE); unsexed conventional insemination (40.3% for HO; 44.0% for JE), and competitors' sexing technology (36.3% for HO; 34.2% for JE) wherein the desired sperm cells are physically separated from the undesired sperm cells. Consistently, the CR using the IntelliGen Sexed Technology was comparable to the CR using conventional insemination technique while they were both better compared to the CR using competitors' sexing technology.

TABLE 2

Heifer Insemination Records on Farms that used all 3 technology types (conventional, Genus Sexed Semen (IntelliGen), Other Sexed Technology).

| Heifers | IntelliGen Sexed Tech (N) CR % | Conventional (N) CR % | Other Sexed Tech. (N) CR % | Farms (N) |
|---|---|---|---|---|
| HO | (1109) 63.8% | (398) 64.6 | (1785) 54.7% | 14 |
| JE | (155) 61.9% | (50) 38% | (245) 47.8% | 1 |

TABLE 3

Cow Insemination records on farms that used all 3 technology types. The inseminations were from September 1 and only on $1^{st}$ and $2^{nd}$ service on cow.

| Cows | IntelliGen Sexed Tech (N) CR % | Conventional (N) CR % | Other Sexed Tech. (N) CR % | Farms (N) |
|---|---|---|---|---|
| HO | (665) 42.6% | (3510) 40.3% | (259) 36.3% | 7 |
| JE | (2762) 37.5% | (1037) 44.0% | (2794) 34.2% | 5 |

In another embodiment, the current invention discloses a collection of a population of sperm cells with both a desired subpopulation and an ablated undesired subpopulation according to the a method of inseminating an animal that comprises flowing a stream of a population of sperm cells through a channel, differentiating the sperm cells into two subpopulations of X-chromosome containing sperm cells and Y-chromosome containing sperm cells, selecting a desired subpopulation, ablating an undesired subpopulation, and collecting both the subpopulations of sperm cells including the desired subpopulation and the ablated undesired subpopulation together, wherein the collected population of sperm cells is used to fertilize an egg.

In another embodiment, the current invention discloses an embryo, wherein the embryo is made from the step of inserting the collected population of sperm cells into the animal to fertilize an egg. In an alternative embodiment, the embryo is made from fertilizing the egg in vitro with the collected population of sperm cells creating a fertilized egg, and implanting the fertilized egg within the mammal (human or animal), and wherein the implantation occurs within forty-eight hours following fertilization.

Further aspects and embodiments of the present technology are described in the following paragraphs.

A method of producing a sperm cell composition the steps of: flowing a stream of a population of sperm cells through a channel; differentiating the sperm cells into two subpopulations of X-chromosome containing sperm cells and Y-chromosome containing sperm cells; selecting a desired subpopulation; ablating an undesired subpopulation; and collecting both the subpopulations of sperm cells including the desired subpopulation and the ablated undesired subpopulation together.

A method of fertilizing one or more eggs comprising the steps of providing at least one egg obtained from a female mammal, providing the sperm cell composition from a male mammal of the same species produced using the method described above as the female mammal, and mixing the one or more eggs with the sperm cell composition. An aspect of the methods described above, wherein the female mammal is a cow or a heifer. An aspect of the methods described above, wherein the male mammal is a bull or boar. An aspect of the methods described above, further comprising implanting the at least one fertilized egg within the female animal within forty-eight hours following fertilization. An aspect of the methods described above, further comprising obtaining genetic information of the sperm cells or the fertilized egg prior to implantation. An aspect of the methods described above, wherein the implanting the fertilized egg within the female animal occurs within forty-eight hours following obtaining the genetic information of the fertilized egg. An aspect of the methods described above, wherein obtaining the genetic information of the fertilized egg comprises removing at least one cell of the fertilized egg for analysis. An aspect of the methods described above, wherein obtaining the genetic information of the fertilized egg comprises sequencing a portion of a DNA molecule or an RNA molecule of the fertilized egg. An aspect of the methods described above, wherein obtaining the genetic information of the fertilized egg occurs within forty-eight hours following removing at least one cell of the fertilized egg for analysis. An aspect of the methods described above, wherein obtaining the genetic information of the fertilized egg occurs within twenty-four hours following removing at least one cell of the fertilized egg for analysis.

A method of producing an embryo comprising using the sperm cell composition produced using the method described above and an assisted reproductive technique. An aspect of the methods described above, wherein the assisted reproductive technique is selected from the group consisting of in vitro fertilization (IVF), artificial insemination (AI), intracytoplasmic sperm injection (ICSI), multiple ovulation and embryo transfer (MOET), and other embryo transfer techniques. An aspect of the methods described above, wherein a heifer or cow is inseminated using artificial insemination. An aspect of the methods described above, wherein success rate for insemination is better than insemination comprising a physical separation of selected sperm cells from unselected sperm cells. An aspect of the methods described above, wherein success rate for insemination of a heifer is at least about 60% on average. An aspect of the methods described above, wherein success rate for insemination of the cow is at least about 37% on average.

An aspect of the methods described above, wherein flowing the stream of the population of sperm cells through the channel comprises orienting the sperm cells in the population in a particular position with respect to the channel; aligning the sperm cells wherein the sperm cells are flowing singularly through the channel; and exiting all the sperm cells through an output portion of the channel. An aspect of the methods described above, wherein orienting the sperm cells and aligning the sperm cells comprise compressing the stream by sheath fluid flowing along at least one side of the stream wherein the compressing further comprises intersecting at a substantially 90 degree vertical plane by the sheath fluid from above the stream. An aspect of the methods described above, wherein the sheath fluid is in laminar flow with the stream of the population of sperm cells during the differentiating and the ablating steps. An aspect of the methods described above, wherein orienting the sperm cells and aligning the sperm cells comprises compressing the sperm cells by an inertial force directed by a designed structure of the channel. An aspect of the methods described above, wherein differentiating the sperm cells into two subpopulations of X-chromosome containing sperm cells and Y-chromosome containing sperm cells is accomplished via the steps of: illuminating the sperm cells with a beam of light; and detecting a difference between the desired subpopulation and the ablated undesired subpopulation. An aspect of the methods described above, wherein the beam of light is from an LED light source. An aspect of the methods described above, wherein the beam of light is from a detection laser. An aspect of the methods described above, wherein the beam of light is split into multiple beams of light; and wherein each beam of light of the multiple beams of light is configured to illuminate a different sperm cell. An aspect of the methods described above, wherein the beam of light is not split into multiple beams and the beam illuminates one sperm cell at a time. An aspect of the methods described above, wherein the beam of light is emitted as a continuous wave. An aspect of the methods described above, wherein the beam of light is emitted in pulses. An aspect of the methods described above, wherein the difference comprises how the sperm cells reflect, refract, diffract, absorb, and/or emit the light. An aspect of the methods described above, wherein a molecule of the sperm cell or a molecule associated with the sperm cell is excited by the beam of light and the molecule emits a second beam of light in a Stoke shift. An aspect of the methods described above, wherein the difference reflects a difference in DNA concentration per cell. An aspect of the methods described above, wherein the difference between the subpopulations is at least about 3.8% difference in DNA content.

An aspect of the methods described above, wherein selecting the desired subpopulation comprises gating each subpopulation based on a physical difference for each subpopulation; and identifying the desired subpopulation. An aspect of the methods described above, wherein gating each subpopulation and identifying the desired subpopulation comprises correlating a graphic representation for each subpopulation; and choosing or marking the desired subpopulation. An aspect of the methods described above, wherein ablating the undesired subpopulation further comprises damaging or killing the undesired subpopulation of sperm cells with a second beam of light in an area of the channel, wherein a damaged or killed sperm cell is rendered unable to fertilize an egg. An aspect of the methods described above, wherein the second beam of light is from a laser. An aspect of the methods described above, wherein the laser is configured to provide a pulse of beam of light and wherein the laser is configured to recharge to damage or kill the next sperm cell that enters the area of the channel. An aspect of the methods described above, wherein the beam of light is tightly focused with a blade-shape configured to cut across at least approximately 2 microns in length of the channel. An aspect of the methods described above, wherein the damaging or killing is coordinated with travel time of the sperm cells and wherein the sperm cells are travelling at a known velocity.

A process for the production of at least one fertilized egg from a female mammal, the process comprising the steps of a) flowing a stream of a population of sperm cells through a channel; b) differentiating the sperm cells into two subpopulations of X-chromosome containing sperm cells and Y-chromosome containing sperm cells; c) selecting a desired subpopulation;

d) ablating an undesired subpopulation; e) collecting both the subpopulations of sperm cells including the desired subpopulation and the ablated undesired subpopulation together; and f) mixing at least a portion of the collected sperm cells with at least one egg from a female mammal to produce a fertilized egg. An aspect of the process described above, further comprising implanting the at least one fertilized egg within the female animal within forty-eight hours following fertilization. An aspect of the process described above, further comprising obtaining genetic information of the sperm cells or the fertilized egg prior to implantation.

A process for the production of at least one embryo from a female mammal, the process comprising the steps of a) flowing a stream of a population of sperm cells through a channel; b) differentiating the sperm cells into two subpopulations of X-chromosome containing sperm cells and Y-chromosome containing sperm cells; c) selecting a desired subpopulation; d) ablating an undesired subpopulation; e) collecting both the subpopulations of sperm cells including the desired subpopulation and the ablated undesired subpopulation together; f) inserting at least a portion of the collected sperm cells into a female mammal; and g) fertilizing at least one egg from said female mammal to produce at least one embryo from said female mammal.

The construction and arrangements of the microfluidic chip system with focused energy device, as shown in the various illustrative embodiments, are illustrative only. It should be noted that the orientation of various elements may differ according to other illustrative embodiments, and that such variations are intended to be encompassed by the present disclosure. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes and omissions may also be made in the design, operating conditions and arrangement of the various illustrative embodiments without departing from the scope of the present disclosure. All such modifications and variations are intended to be included herein within the scope of the invention and protected by the following claims.

What is claimed is:

1. A method of producing a sperm cell composition, comprising the steps of
   flowing a stream of a population of sperm cells through a channel;
   differentiating the sperm cells into two subpopulations of X-chromosome containing sperm cells and Y-chromosome containing sperm cells;
   selecting a desired subpopulation;
   ablating an undesired subpopulation at a predetermined delay time from selecting the desired subpopulation, wherein the predetermined delay time is 1 µs or longer; and
   collecting both the subpopulations of sperm cells including the desired subpopulation and the ablated undesired subpopulation together.

2. A method of fertilizing one or more eggs comprising the steps of providing at least one egg obtained from a female mammal, providing the sperm cell composition of claim 1 from a male mammal of the same species as the female mammal, and mixing the one or more eggs with the sperm cell composition.

3. The method of claim 2, wherein the female mammal is a cow or a heifer.

4. The method of claim 2, wherein the male mammal is a bull or boar.

5. The method of claim 2, further comprising implanting the at least one fertilized egg within the female animal within forty-eight hours following fertilization.

6. The method of claim 2, further comprising obtaining genetic information of the sperm cells or the fertilized egg prior to implantation.

7. The method of claim 6, wherein the implanting the fertilized egg within the female animal occurs within forty-eight hours following obtaining the genetic information of the fertilized egg.

8. The method of claim 6, wherein obtaining the genetic information of the fertilized egg comprises removing at least one cell of the fertilized egg for analysis.

9. The method of claim 6, wherein obtaining the genetic information of the fertilized egg comprises sequencing a portion of a DNA molecule or an RNA molecule of the fertilized egg.

10. The method of claim 6, wherein obtaining the genetic information of the fertilized egg occurs within forty-eight hours following removing at least one cell of the fertilized egg for analysis.

11. The method of claim 10, wherein obtaining the genetic information of the fertilized egg occurs within twenty-four hours following removing at least one cell of the fertilized egg for analysis.

12. A method of producing an embryo comprising using the sperm cell composition of claim 1 and an assisted reproductive technique.

13. The method of claim 12, wherein the assisted reproductive technique is selected from the group consisting of in vitro fertilization (IVF), artificial insemination (AI), intracytoplasmic sperm injection (ICSI), multiple ovulation and embryo transfer (MOET), and other embryo transfer techniques.

14. The method of claim 13, wherein a heifer or cow is inseminated using artificial insemination.

15. The method of claim 14, wherein success rate for insemination is better than insemination comprising a physical separation of selected sperm cells from unselected sperm cells.

16. The method of claim 15, wherein success rate for insemination of a heifer is at least about 60% on average.

17. The method of claim 15, wherein success rate for insemination of the cow is at least about 37% on average.

18. The method of claim 1 wherein flowing the stream of the population of sperm cells through the channel comprises
   orienting the sperm cells in the population in a particular position with respect to the channel;
   aligning the sperm cells wherein the sperm cells are flowing singularly through the channel; and
   exiting all the sperm cells through an output portion of the channel.

19. The method of claim 18, wherein orienting the sperm cells and aligning the sperm cells comprise
   compressing the stream by sheath fluid flowing along at least one side of the stream wherein the compressing further comprises intersecting at a substantially 90 degree vertical plane by the sheath fluid from above the stream.

20. The method of claim 19, wherein the sheath fluid is in laminar flow with the stream of the population of sperm cells during the differentiating and the ablating steps.

21. The method of claim 18, wherein orienting the sperm cells and aligning the sperm cells comprises compressing the sperm cells by an inertial force directed by a designed structure of the channel.

22. The method of claim 1, wherein differentiating the sperm cells into two subpopulations of X-chromosome containing sperm cells and Y-chromosome containing sperm cells is accomplished via the steps of:
  illuminating the sperm cells with a beam of light; and
  detecting a difference between the desired subpopulation and the ablated undesired subpopulation.

23. The method of claim 22, wherein the beam of light is from an LED light source.

24. The method of claim 22, wherein the beam of light is from a detection laser.

25. The method of claim 22, wherein the beam of light is split into multiple beams of light; and wherein each beam of light of the multiple beams of light is configured to illuminate a different sperm cell.

26. The method of claim 22, wherein the beam of light is not split into multiple beams and the beam illuminates one sperm cell at a time.

27. The method of claim 22, wherein the beam of light is emitted as a continuous wave.

28. The method of claim 22, wherein the beam of light is emitted in pulses.

29. The method of claim 22, wherein the difference comprises how the sperm cells reflect, refract, diffract, absorb, and/or emit the light.

30. The method of claim 22, wherein a molecule of the sperm cell or a molecule associated with the sperm cell is excited by the beam of light and the molecule emits a second beam of light in a Stoke shift.

31. The method of claim 22, wherein the difference reflects a difference in DNA concentration per cell.

32. The method of claim 31, wherein the difference between the subpopulations is at least about 3.8% difference in DNA content.

33. The method of claim 1, wherein selecting the desired subpopulation comprises gating each subpopulation based on a physical difference for each subpopulation; and
  identifying the desired subpopulation.

34. The method of claim 33, wherein gating each subpopulation and identifying the desired subpopulation comprises
  correlating a graphic representation for each subpopulation; and
  choosing or marking the desired subpopulation.

35. The method of claim 1, wherein ablating the undesired subpopulation further comprises
  damaging or killing the undesired subpopulation of sperm cells with a second beam of light in an area of the channel,
  wherein a damaged or killed sperm cell is rendered unable to fertilize an egg.

36. The method of claim 35, wherein the second beam of light is from a laser.

37. The method of claim 36, wherein the laser is configured to provide a pulse of beam of light and wherein the laser is configured to recharge to damage or kill the next sperm cell that enters the area of the channel.

38. The method of claim 35, wherein the beam of light is tightly focused with a blade-shape configured to cut across at least approximately 2 microns in length of the channel.

39. The method of claim 35, wherein the damaging or killing is coordinated with travel time of the sperm cells and wherein the sperm cells are travelling at a known velocity.

40. A process for the production of at least one fertilized egg from a female mammal, the process comprising the steps of
  a) flowing a stream of a population of sperm cells through a channel;
  b) differentiating the sperm cells into two subpopulations of X-chromosome containing sperm cells and Y-chromosome containing sperm cells;
  c) selecting a desired subpopulation;
  d) ablating an undesired subpopulation at a predetermined delay time from selecting the desired subpopulation, wherein the predetermined delay time is 1 µs or longer;
  e) collecting both the subpopulations of sperm cells including the desired subpopulation and the ablated undesired subpopulation together; and
  f) mixing at least a portion of the collected sperm cells with at least one egg from a female mammal to produce a fertilized egg.

41. The process of claim 40, further comprising implanting the at least one fertilized egg within the female animal within forty-eight hours following fertilization.

42. The process of claim 40, further comprising obtaining genetic information of the sperm cells or the fertilized egg prior to implantation.

43. A process for the production of at least one embryo from a female mammal, the process comprising the steps of
  a) flowing a stream of a population of sperm cells through a channel;
  b) differentiating the sperm cells into two subpopulations of X-chromosome containing sperm cells and Y-chromosome containing sperm cells;
  c) selecting a desired subpopulation;
  d) ablating an undesired subpopulation at a predetermined delay time from selecting the desired subpopulation, wherein the predetermined delay time is 1 µs or longer;
  e) collecting both the subpopulations of sperm cells including the desired subpopulation and the ablated undesired subpopulation together;
  f) inserting at least a portion of the collected sperm cells into a female mammal; and
  g) fertilizing at least one egg from said female mammal to produce at least one embryo from said female mammal.

* * * * *